(12) United States Patent
Reid et al.

(10) Patent No.: US 11,898,984 B2
(45) Date of Patent: Feb. 13, 2024

(54) NANOPORE ARRAYS FOR SEQUENCING NUCLEIC ACIDS

(71) Applicant: Oxford Nanopore Technologies plc., Oxford (GB)

(72) Inventors: Stuart William Reid, Oxford (GB); Terence Alan Reid, Kidlington (GB); James Anthony Clarke, Kidlington (GB); Steven Paul White, Oxford (GB); Gurdial Singh Sanghera, Oxford (GB)

(73) Assignee: Oxford Nanopore Technologies PLC

(*) Notice: Subject to any disclaimer, the term of this patent is extended or adjusted under 35 U.S.C. 154(b) by 0 days.

(21) Appl. No.: 16/692,977

(22) Filed: Nov. 22, 2019

(65) Prior Publication Data

US 2020/0080966 A1    Mar. 12, 2020

Related U.S. Application Data

(63) Continuation of application No. 16/294,670, filed on Mar. 6, 2019, now abandoned, which is a
(Continued)

(30) Foreign Application Priority Data

Dec. 19, 2007 (GB) ..................................... 0724736

(51) Int. Cl.
*G01N 27/447* (2006.01)
*G01N 33/487* (2006.01)
(Continued)

(52) U.S. Cl.
CPC .... *G01N 27/44791* (2013.01); *B01L 3/50273* (2013.01); *B01L 3/502707* (2013.01);
(Continued)

(58) Field of Classification Search
CPC .......... G01N 27/44791; G01N 27/453; G01N 33/48721; C12Q 1/6869
See application file for complete search history.

(56) References Cited

U.S. PATENT DOCUMENTS 3,799,743 A    3/1974  Alexander et al.
4,154,795 A    5/1979  Thorne
(Continued)

FOREIGN PATENT DOCUMENTS

CN    1303147 A    7/2001
CN    1434461      8/2003
(Continued)

OTHER PUBLICATIONS

X. Han, Nanopore Arrays for stable and functional free-standing lipid bilayers, Advanced Materials, vol. 19, p. 4466-70, published on Nov. 28, 2007. (Year: 2007).*
(Continued)

*Primary Examiner* — Caitlyn Mingyun Sun
(74) *Attorney, Agent, or Firm* — Baker Botts L.L.P.

(57) ABSTRACT

To form a layer separating two volumes of aqueous solution, there is used an apparatus comprising elements defining a chamber, the elements including a body of non-conductive material having formed therein at least one recess opening into the chamber, the recess containing an electrode. A pre-treatment coating of a hydrophobic fluid is applied to the body across the recess. Aqueous solution, having amphiphilic molecules added thereto, is flowed across the body to cover the recess so that aqueous solution is introduced into the recess from the chamber and a layer of the amphiphilic molecules forms across the recess separating a volume of aqueous solution introduced into the recess from the remaining volume of aqueous solution.

18 Claims, 27 Drawing Sheets

Specification includes a Sequence Listing.

Related U.S. Application Data continuation of application No. 15/434,574, filed on Feb. 16, 2017, now Pat. No. 10,416,117, which is a continuation of application No. 14/302,287, filed on Jun. 11, 2014, now abandoned, which is a continuation of application No. 12/339,956, filed on Dec. 19, 2008, now abandoned.

(60) Provisional application No. 61/080,492, filed on Jul. 14, 2008.

(51) Int. Cl.
| | |
|---|---|
| C12Q 1/6869 | (2018.01) |
| G01N 27/453 | (2006.01) |
| G01N 27/327 | (2006.01) |
| B01L 3/00 | (2006.01) |

(52) U.S. Cl.
CPC ....... *C12Q 1/6869* (2013.01); *G01N 27/3278* (2013.01); *G01N 27/453* (2013.01); *G01N 33/48721* (2013.01); *B01L 2300/0645* (2013.01); *B01L 2300/161* (2013.01); *B01L 2400/0421* (2013.01); *B01L 2400/0427* (2013.01)

(56) References Cited

U.S. PATENT DOCUMENTS

| | | | |
|---|---|---|---|
| 5,234,566 | A | 8/1993 | Osman et al. |
| 5,403,451 | A | 4/1995 | Riviello et al. |
| 5,795,782 | A * | 8/1998 | Church ............... C07K 14/705 |
| | | | 435/4 |
| 6,056,922 | A | 5/2000 | Ikematsu |
| 6,300,141 | B1 | 10/2001 | Segal et al. |
| 6,479,288 | B1 | 11/2002 | Laffafian et al. |
| 6,503,452 | B1 | 1/2003 | Boxer et al. |
| 6,699,697 | B2 | 3/2004 | Klemic et al. |
| 6,863,833 | B1 | 3/2005 | Bloom et al. |
| 6,913,697 | B2 | 7/2005 | Lopez et al. |
| 6,916,488 | B1 | 7/2005 | Meier et al. |
| 6,936,433 | B2 | 8/2005 | Akeson et al. |
| 7,077,939 | B1 | 7/2006 | Crooks et al. |
| 7,144,486 | B1 | 12/2006 | Fritsch et al. |
| 7,169,272 | B2 | 1/2007 | Fritsch et al. |
| 7,745,116 | B2 | 6/2010 | Williams |
| 7,939,270 | B2 | 5/2011 | Holden et al. |
| 8,124,191 | B2 | 2/2012 | Ervin et al. |
| 8,461,854 | B2 | 6/2013 | Chen et al. |
| 10,481,144 | B2 | 11/2019 | Turner et al. |
| 2002/0123048 | A1 | 9/2002 | Gau |
| 2003/0015422 | A1 | 1/2003 | Fritsch et al. |
| 2003/0098248 | A1 | 5/2003 | Vogel et al. |
| 2003/0099951 | A1 * | 5/2003 | Akeson ............... C12Q 1/6827 |
| | | | 204/461 |
| 2003/0111340 | A1 | 6/2003 | Cheng et al. |
| 2005/0014162 | A1 | 1/2005 | Barth et al. |
| 2005/0022895 | A1 * | 2/2005 | Barth ............... B01L 3/502723 |
| | | | 141/5 |
| 2005/0230272 | A1 | 10/2005 | Lee et al. |
| 2006/0163063 | A1 | 7/2006 | Picollet-Dahan et al. |
| 2007/0035308 | A1 | 2/2007 | Ide |
| 2008/0254995 | A1 | 10/2008 | Kim et al. |
| 2008/0257859 | A1 * | 10/2008 | Golovchenko .. G01N 33/48721 |
| | | | 216/19 |
| 2009/0167288 | A1 | 7/2009 | Reid et al. |
| 2010/0147450 | A1 | 6/2010 | Takeuchi et al. |
| 2010/0327874 | A1 * | 12/2010 | Liu .................. G01N 33/48721 |
| | | | 324/464 |
| 2011/0120871 | A1 | 5/2011 | Reid et al. |
| 2011/0121840 | A1 | 5/2011 | Sanghera et al. |
| 2011/0214991 | A1 | 9/2011 | Kim et al. |
| 2011/0287414 | A1 * | 11/2011 | Chen .................... C12Q 1/6869 |
| | | | 435/6.11 |
| 2012/0010085 | A1 | 1/2012 | Rava et al. |
| 2013/0140192 | A1 | 6/2013 | Behrends et al. |
| 2014/0034497 | A1 * | 2/2014 | Davis ............... G01N 27/44791 |
| | | | 204/451 |
| 2014/0255921 | A1 | 9/2014 | Moysey et al. |
| 2014/0296083 | A1 | 10/2014 | Brown et al. |
| 2014/0329693 | A1 | 11/2014 | Reid et al. |
| 2014/0335512 | A1 | 11/2014 | Moysey et al. |
| 2014/0346059 | A1 | 11/2014 | Akeson |
| 2015/0014160 | A1 | 1/2015 | Hyde et al. |
| 2015/0065354 | A1 | 3/2015 | Moysey et al. |
| 2015/0191709 | A1 | 7/2015 | Heron et al. |
| 2015/0218629 | A1 | 8/2015 | Heron et al. |
| 2015/0265994 | A1 | 9/2015 | Hyde et al. |
| 2015/0268256 | A1 | 9/2015 | Sanghera et al. |
| 2015/0308986 | A1 | 10/2015 | Reid et al. |
| 2016/0040230 | A1 | 2/2016 | Akeson |
| 2016/0257942 | A1 | 9/2016 | Bruce et al. |

FOREIGN PATENT DOCUMENTS

| | | |
|---|---|---|
| CN | 101078704 | 11/2007 |
| CN | 101490277 A | 7/2009 |
| CN | 203466320 U | 9/2013 |
| DE | 102010022929 A1 | 12/2011 |
| EP | 0532215 A2 | 3/1993 |
| EP | 1120469 A2 | 8/2001 |
| EP | 1645628 | 4/2006 |
| EP | 1669746 A1 | 6/2006 |
| EP | 1677102 | 7/2006 |
| EP | 1688742 | 8/2006 |
| EP | 1710578 | 10/2006 |
| EP | 1712909 A1 | 10/2006 |
| EP | 1279921 A1 | 5/2007 |
| EP | 08160644.4 | 7/2008 |
| EP | 2219032 A1 | 8/2010 |
| GB | 2237390 | 5/1991 |
| GB | 2446823 | 8/2008 |
| JP | S5-274882 A | 6/1977 |
| JP | 4127066 A2 | 9/1990 |
| JP | 4014773 A2 | 1/1992 |
| JP | 4-215052 | 8/1992 |
| JP | 7307172 A2 | 11/1995 |
| JP | 2004-158330 A2 | 6/2004 |
| JP | 2005-98718 | 4/2005 |
| JP | 2005-539242 | 12/2005 |
| JP | 2006-312141 | 11/2006 |
| JP | 2008-194573 | 8/2008 |
| JP | 2010186677 A2 | 8/2010 |
| WO | WO 1994/025862 A1 | 11/1994 |
| WO | WO 1997/016545 A1 | 5/1997 |
| WO | WO 1998/058248 | 12/1998 |
| WO | WO 2000/025121 A1 | 5/2000 |
| WO | WO 2000/028312 | 5/2000 |
| WO | WO 2002/024862 A2 | 3/2002 |
| WO | WO 2002/029402 A2 | 4/2002 |
| WO | WO 2002/035221 A1 | 5/2002 |
| WO | WO 2002/082046 A2 | 10/2002 |
| WO | WO 2003/052420 A2 | 6/2003 |
| WO | WO 2004/085609 | * 10/2004 |
| WO | WO-2004085609 A2 * | 10/2004 ............. B82Y 15/00 |
| WO | WO 2005/040783 A1 | 5/2005 |
| WO | WO 2006/012571 A1 | 2/2006 |
| WO | WO 2006/076703 A2 | 7/2006 |
| WO | WO 2006/100484 | 9/2006 |
| WO | WO 2006/104639 | 10/2006 |
| WO | WO 2006/113550 | 10/2006 |
| WO | WO 2006/138160 A2 | 12/2006 |
| WO | WO 2007/028003 A2 | 3/2007 |
| WO | WO 2007/116978 A1 | 10/2007 |
| WO | WO 2007/127327 | 11/2007 |
| WO | WO 2007/132002 A1 | 11/2007 |
| WO | WO 2007/145748 | * 12/2007 ........... G01R 29/027 |
| WO | WO-2007145748 A2 * | 12/2007 ........ G01N 33/48721 |
| WO | WO 2008/012552 A1 | 1/2008 |
| WO | WO 2008/054611 A2 | 5/2008 |
| WO | WO 2008/102120 | 8/2008 |
| WO | WO 2008/102121 | 8/2008 |
| WO | 2008124107 | 10/2008 |

(56) References Cited

FOREIGN PATENT DOCUMENTS

| WO | WO 2008/124107 A1 | 10/2008 | |
|----|----|----|----|
| WO | WO-2008124107 A1 * | 10/2008 | ............... C12Q 1/25 |
| WO | 2009/020682 | 2/2009 | |
| WO | WO 2009/024775 A1 | 2/2009 | |
| WO | WO 2009/035647 A1 | 3/2009 | |
| WO | WO 2009/077734 A2 | 6/2009 | |
| WO | WO 2010/122293 | 10/2010 | |
| WO | WO 2011/154114 A2 | 12/2011 | |
| WO | WO 2012/033524 A2 | 3/2012 | |
| WO | WO 2013/041878 A1 | 3/2013 | |
| WO | WO 2013/057495 A2 | 4/2013 | |
| WO | WO 2013/121224 A1 | 8/2013 | |
| WO | WO 2013/153359 A1 | 10/2013 | |
| WO | WO 2014/064443 A2 | 5/2014 | |
| WO | WO 2014/064444 A1 | 5/2014 | |

OTHER PUBLICATIONS

E.K. Schmitt, Channel Activity of OmpF Monitored in Nano-BLMs, Biophysical Journal, 2006(91), p. 2163-71. (Year: 2006).*
R. Peters, The Nanopore Connection to Cell Membrane Unitary Permeability, Traffic 2005 (6), p. 199-204. (Year: 2005).*
Cheng, Y., et al. "Discrete membrane arrays." *Reviews in Molecular Biotechnology* 74.3 (2000): 159-174.
Bouaidat, Salim, et al. "Surface-directed capillary system; theory, experiments and applications." *Lab on a Chip* 5.8 (2005): 827-836.
Bull, Randy A., Fu-Ren F. Fan, and Allen J. Bard. "Polymer Films on Electrodes VII. Electrochemical Behavior at Polypyrrole-Coated Platinum and Tantalum Electrodes." *Journal of the Electrochemical Society* 129.5 (1982): 1009-1015.
Ikariyama, Yoshihito, and William R. Heineman. "Polypyrrole electrode as a detector for electroinactive anions by flow injection analysis." *Analytical Chemistry* 58.8 (1986): 1803-1806.
Malmstadt, Noah, et al. "Automated formation of lipid-bilayer membranes in a microfluidic device." *Nano letters* 6.9 (2006): 1961-1965.
Third Party Submission Under 37 CPR 1.290 for U.S. Appl. No. 14/302,287 dated May 19, 2016.
http://www.cnki.net, China Academic Journal Electronic Publishing House, pp. 275-278 (1986).
[No Author Listed] Avanti Polar Lipids, Inc. Avanti Polar Lipids-Preparations of Liposomes. Www.avantilipids.com 5 pages. Jul. 1, 2014.
Aghdaei et al., Formation of artificial lipid bilayers using droplet dielectrophoresis. Lab Chip. Oct. 2008;8(10):1617-20. doi: 10.1039/b807374k. Epub Aug. 13, 2008.
Altschul et al., Basic local alignment search tool. J Mol Biol. Oct. 5, 1990;215(3):403-10.
Altschul, A protein alignment scoring system sensitive at all evolutionary distances. J Mol Evol. Mar. 1993;36(3):290-300.
Anrather et al., Supported membrane nanodevices. J Nanosci Nanotechnol. Jan.-Feb. 2004;4(1-2):1-22.
Astier et al., Toward single molecule DNA sequencing: direct identification of ribonucleoside and deoxyribonucleoside 5'-monophosphates by using an engineered protein nanopore equipped with a molecular adapter. J Am Chem Soc. Feb. 8, 2006;128(5):1705-10.
Baaken et al., Planar microelectrode-cavity array for high-resolution and parallel electrical recording of membrane ionic currents. Lab Chip. Jun. 2008;8(6):938-44. doi: 10.1039/b800431e. Epub Apr. 16, 2008.
Bezrukov et al., Counting polymers moving through a single ion channel. Nature. Jul. 28, 1994;370(6487):279-81.
Bruggemann et al., Microchip technology for automated and parallel patch-clamp recording. Small. Jul. 2006;2(7):840-6.
Cheng et al., Discrete membrane arrays. J Biotechnol. Sep. 2000;74(3):159-74.
Cheng et al., Single Ion Channel Sensitivity in Suspended Bilayers on Micromachined Supports. Langmuir. 2001;17(4):1240-1242.

Danelon et al., Cell membranes suspended across nanoaperture arrays. Langmuir. Jan. 3, 2006;22(1):22-5.
Devereux et al., A comprehensive set of sequence analysis programs for the VAX. Nucleic Acids Res. Jan. 11, 1984;12(1 Pt 1):387-95.
Estes et al., Electroformation of giant liposomes from spin-coated films of lipids. Colloids Surf B Biointerfaces. May 10, 2005;42(2):115-23.
Funakoshi et al., Lipid bilayer formation by contacting monolayers in a microfluidic device for membrane protein analysis. Anal Chem. Dec. 15, 2006;78(24):8169-74.
Garstecki et al., Formation of droplets and bubbles in a microfluidic T-junction-scaling and mechanism of break-up. Lab Chip. Mar. 2006;6(3):437-46. Epub Jan. 25, 2006. Erratum in: Lab Chip. May 2006;6(5):693.
Hasanzadeh et al., Room-temperature ionic liquid-based electrochemical nanobiosensors. Trends Anal Chem. Dec. 2012;41:58-74.
Heron et al., Simultaneous measurement of ionic current and fluorescence from single protein pores. J Am Chem Soc. Feb. 11, 2009;131(5):1652-3. doi: 10.1021/ja808128s.
Hirano et al., Lipid Bilayers at Gel/Gel Interface for Ion Channel Recordings. Surf. Sci. Nanotech. 2008;6:130-133.
Holden et al., Functional bionetworks from nanoliter water droplets. J Am Chem Soc. Jul. 11, 2007;129(27):8650-5. Epub Jun. 16, 2007.
Hovis et al., Patterning and Composition Arrays of Supported Lipid Bilayers by Microcontact Printing. Langmuir. 2001;17:3400-3405.
Hromada et al., Single molecule measurements within individual membrane-bound ion channels using a polymer-based bilayer lipid membrane chip. Lab Chip. Apr. 2008;8(4):602-8. doi:10.1039/b716388f. Epub Feb. 29, 2008.
Ide et al., A novel method for artificial lipid-bilayer formation. Biosens Bioelectron. Oct. 15, 2005;21(4):672-7. Epub Jan. 26, 2005.
Jeon et al., Long-term storable and shippable lipid bilayer membrane platform. Lab Chip. Oct. 2008;8(10):1742-4. doi: 10.1039/b807932c. Epub Aug. 22, 2008.
Jung et al., Detecting protein-ligand binding on supported bilayers by local pH modulation. J Am Chem Soc. Jan. 28, 2009;131(3):1006-14. doi: 10.1021/ja804542p.
Kam et al., Spatially Selective Manipulation of Supported Lipid Bilayers by Laminar Flow: Steps Toward Biomembrane Microfluidic. Langmuir. 2003;19(5):1624-1631.
Kasianowicz et al., Protonation dynamics of the alpha-toxin ion channel from spectral analysis of pH-dependent current fluctuations. Biophys J. Jul. 1995;69(1):94-105.
Khafizov, Single Molecole Force Spectroscopy of Single Stranded Dna Binding Protein and Rep Helicase. University of Illinois at Urbana-Champaign Dissertation. 2012.
Kim et al., Liquid-slate field-effect transistors using electrowetting. Applied Physics Letters. 90:043507-1-043507-3.
Korolev et al., Major domain swiveling revealed by the crystal structures of complexes of E. coli Rep helicase bound to single-stranded DNA and ADP. Cell. Aug. 22, 1997;90(4):635-47.
Krantz Lab. Planar Lipid Bilayer Electrophysiology Equipment. Department of Molecular & Cell Biology, University of California, Berkeley. Oct. 6, 2007. Last accessed at mcb.berkeley.edu/labs/krantz/equipment/blm.html on Nov. 26, 2014.
Kung et al., Printing via Photolithography on Micropartitioned Fluid Lipid Membranes. Adv. Materials. 2000;12(10):731-734.
Langecker et al., Synthetic lipid membrane channels formed by designed DNA nanostructures. Science. Nov. 16, 2012;338(6109):932-6. doi: 10.1126/science.1225624.
Le Pioufle et al., Lipid bilayer microarray for parallel recording of transmembrane ion currents. Anal Chem. Jan. 1, 2008;80(1):328-32. Epub Nov. 15, 2007.
Lee et al., Ion channel switch array:A biosensor for detecting multiple pathogens. Industrial Biotechnology. May 2005;1(1):26-31. doi:10.1089/ind.2005.1.26.
Lee et al., Nanoarrays of tethered lipid bilayer rafts on poly(vinyl alcohol) hydrogels. Lab Chip. Jan. 7, 2009;9(1):132-9. doi: 10.1039/b809732a. Epub Oct. 22, 2008.
Lee et al., Polyelectrolyte Micropatterning Using Agarose Plane Stamp and a Substrate Having Microscale Features on Its Surface. Bull. Korean Chem. Soc., vol. 26(10):1539-1542 (2005).

(56) References Cited

OTHER PUBLICATIONS

Lewis et al., The Mesomorphic Phase Behavior of Lipid Bilayers. Structure Biological Membranes. 3rd Ed. Ed: Yeagle. CRC Press 2011. 19-89.

Li et al., Microfluidic system for planar patch clamp electrode arrays. Nano Lett. Apr. 2006;6(4):815-9.

Lieberman et al., Processive replication of single DNA molecules in a nanopore catalyzed by phi29 DNA polymerase. J Am Chem Soc. Dec. 22, 2010;132(50):17961-72. doi:10.1021/ja1087612. Epub Dec. 1, 2010.

Luan et al., Base-by-base ratcheting of single stranded DNA through a solid-state nanopore.Phys Rev Lett. Jun. 11, 2010;104(23):238103. Epub Jun. 10, 2010.

Mach et al., Miniaturized planar lipid bilayer: increased stability, low electric noise and fast fluid perfusion. Anal Bioanal Chem. Feb. 2008;390(3):841-6. Epub Oct. 31, 2007.

Majd et al., Hydrogel stamping of arrays of supported lipid bilayers with various lipid compositions for the screening of drug-membrane and protein-membrane interactions. Angew Chem Int Ed Engl. Oct. 21, 2005;44(41):6697-700.

Malmstadt et al., Automated formation of lipid-bilayer membranes in a microfluidic device. Nano Lett. Sep. 2006;6(9):1961-5.

Mangold et al., Reference electrodes based on conducting polymers. Fresenius J Anal Chem. Jun. 2000;367(4):340-2.

Mastrangeli et al., Challenges for Capillary Self-Assembly of Microsystems. IEEE Transactions. Jan. 2011;1(1):133-149.

Mastrangeli et al., Self-assembly from milli- to nanoscales: methods and applications. J Micro Microeng. 2009;19:083001.

Maurer et al., Reconstitution of ion channels in agarose-supported silicon orifices. Biosens Bioelectron. May 15, 2007;22(11):2577-84. Epub Nov. 13, 2006.

McAlduff et al., Freestanding lipid bilayers as substrates for electron cryomicroscopy of integral membrane proteins. J Microsc. Feb. 2002;205(Pt 2):113-7.

Montal et al., Formation of bimolecular membranes from lipid monolayers and a study of their electrical properties. Proc Natl Acad Sci U S A. Dec. 1972;69(12):3561-6.

Moran-Mirabal et al., Micrometer-sized supported lipid bilayer arrays for bacterial toxin binding studies through total internal reflection fluorescence microscopy. Biophys J. Jul. 2005;89(1):296-305. Epub Apr. 15, 2005.

Ogier et al., "Suspended Planar Phospholipid Bilayers on Micromachined Supports," Langmuir, vol. 16:5696-5701 (2000).

Onoe et al., Three-Dimensional Micro-Self-Assembly Using Hydrophobic Interaction Controlled by Self-Assembled Monolayers. J Micro Systems. Aug. 2004;13(4):603-611.

Parthasarathy et al., Protein patterns at lipid bilayer junctions. Proc Natl Acad Sci U S A. Aug. 31, 2004;101(35):12798-803. Epub Aug. 20, 2004.

Peterman et al., "Ion Channels and Lipid Bilayer Membranes Under High Potentials Using Microfabricaled Apertures," Biomedical Microdevices, vol. 4(3):231-236 (2002).

Polk et al., "Ag/AgCl microelectrodes with improved stability for microfluidics," Sensors and Actuators B., vol. 114:239-247 (2006).

Rauf et al., Studies on sildenafil citrate (Viagra) interaction with DNA using electrochemical DNA biosensor. Biosens Bioelectron. May 15, 2007;22(11):2471-7. Epub Nov. 7, 2006.

Romer et al., Impedance analysis and single-channel recordings on nano-black lipid membranes based on porous alumina. Biophys J. Feb. 2004;86(2):955-65.

Sackmann, Supported membranes: scientific and practical applications. Science. Jan. 5, 1996;271(5245):43-8.

Sandison et al., "Rapid fabrication of polymer microfluidic systems for the production of artificial lipid bilayers," J. Micromech. Microeng., vol. 15:S139-S144 (2005).

Sandison et al., Air-exposure technique for the formation of artificial lipid bilayers in microsystems. Langmuir. Jul. 17, 2007;23(15):8277-84. Epub Jun. 22, 2007.

Sapra et al., Lipid-coated hydrogel shapes as components of electrical circuits and mechanical devices. Sci Rep. 2012;2:848. doi: 10.1038/srep00848. Epub Nov. 14, 2012.

Sarles et al., Bilayer formation between lipid-encased hydrogels contained in solid substrates. ACS Appl Mater Interfaces. Dec. 2010;2(12):3654-63. doi: 10.1021/am100826s. Epub Nov. 10, 2010.

Schindler et al., Branched bimolecular lipid membranes. Biophys J. Sep. 1976;16(9):1109-13.

Schmidt et al., A Chip-Based Biosensor for the Functional Analysis of Single Ion Channels. Angew Chem Int Ed Engl. Sep. 1, 2000;39(17):3137-3140.

Shim et al., Stochastic sensing on a modular chip containing a single-ion channel. Anal Chem. Mar. 15, 2007;79(6):2207-13. Epub Feb. 9, 2007.

Soni et al., Synchronous optical and electrical detection of biomolecules traversing through solid-state nanopores. Rev Sci Instrum. Jan. 2010;81(1):014301. doi: 10.1063/1.3277116.

Stoddart et al., Single-nucleotide discrimination in immobilized DNA oligonucleotides with a biological nanopore. Proc Natl Acad Sci U S A. May 12, 2009;106(19):7702-7. doi: 10.1073/pnas.0901054106. Epub Apr. 20, 2009.

Sun et al., Microfluidic static droplet arrays with tuneable gradients in material composition. Lab Chip. Dec. 7, 2011;11(23):3949-52. doi: 10.1039/c1lc20709a. Epub Oct. 12, 2011.

Suzuki et al., Highly reproducible method of planar lipid bilayer reconstitution in polymethyl methacrylate microfluidic chip. Langmuir. Feb. 14, 2006;22(4):1937-42.

Suzuki et al., Planar lipid bilayer reconstitution with a micro-fluidic system. Lab Chip. Oct. 2004;4(5):502-5. Epub Sep. 2, 2004.

Suzuki et al., Planar Lipid Membrane Array for Membrane Protein Chip. 17th IEEE International Conference on Micro Electro Mechanical Systems (MEMS), pp. 272-275 (2004).

Syms et al., Surface Tension-Powered Self-Assembly of Microstructures—The State of the Art. J Micro Systems. Aug. 2003;12(4):387-417.

Thorsen et al., Dynamic pattern formation in a vesicle-generating microfluidic device. Phys Rev Lett. Apr. 30, 2001;86(18):4163-6.

Urisu et al., Formation of high-resistance supported lipid bilayer on the surface of a silicon substrate with microelectrodes. Nanomedicine. Dec. 2005; 1(4):317-22.

Vidinha et al., Ion jelly: a tailor-made conducting material for smart electrochemical devices. Chem Commun (Camb). Nov. 30, 2008;(44):5842-4. doi: 10.1039/b811647d. Epub Oct. 3, 2008.

Vulto et al., Microfluidic channel fabrication in dry film resist for production and prototyping of hybrid chips. Lab Chip. Feb. 2005;5(2):158-62. Epub Dec. 3, 2004.

Wagterveld et al., Ultralow hysteresis superhydrophobic surfaces by excimer laser modification of SU-8. Langmuir. Dec. 19, 2006;22(26):10904-8.

Zagnoni et al., Bilayer lipid membranes from falling droplets. Anal Bioanal Chem. Mar. 2009;393(6-7):1601-5. doi:10.1007/s00216-008-2588-5. Epub Jan. 19, 2009.

Zagnoni et al., Controlled delivery of proteins into bilayer lipid membranes on chip. Lab Chip. Sep. 2007;7(9):1176-83. Epub Jun. 27, 2007.

Zagnoni et al., Microfluidic array platform for simultaneous lipid bilayer membrane formation. Biosens Bioelectron. Jan. 1, 2009;24(5):1235-40. doi: 10.1016/j.bios.2008.07.022. Epub Jul. 23, 2008.

Hui Wang et al., "Nanopores with a spark for single-molecule detection", at 2001 Nature Publishing Group, nature biotechnology vol. 19, Jul. 2001 pp. 622-623.

William L. Hwang et al., "Electrical Behavior of Droplet Interface Bilayer Networks: Experimental Analysis and Modeling", JACS Articles, J. Am. Chem. SOC. 2007, 129, pp. 11854-11864, Sep. 1, 2007.

Michael Goryll et al., "Integrated sensor design using ion channels inserted into lipid bilayer membranes", 2004 4th IEEE Conference on Nanotechnology, pp. 302-304.

Hagan Bayley et al., "Stochastic sensors inspired by biology", Nature, vol. 413, Sep. 13, 2001, pp. 226-230.

Jacob Schmidt, "Stochastic sensors", J. Mater. Chem., 2005, 15, 831-840, DOI: 10.1039/b414551h, Dec. 20, 2004.

(56) References Cited

OTHER PUBLICATIONS

S.J. Wilk et al., "Integrated electrodes on a silicon based ion channel measurement platform", Biosensors and Bioelectronics 23 (2007) 183-190, Apr. 8, 2007.

Stefan HOWORKA et al., "Sequence-specific detection of individual DNA strands using engineered nanopores", Nature Biotechnology vol. Jul. 19, 2001 pp. 636-639.

* cited by examiner

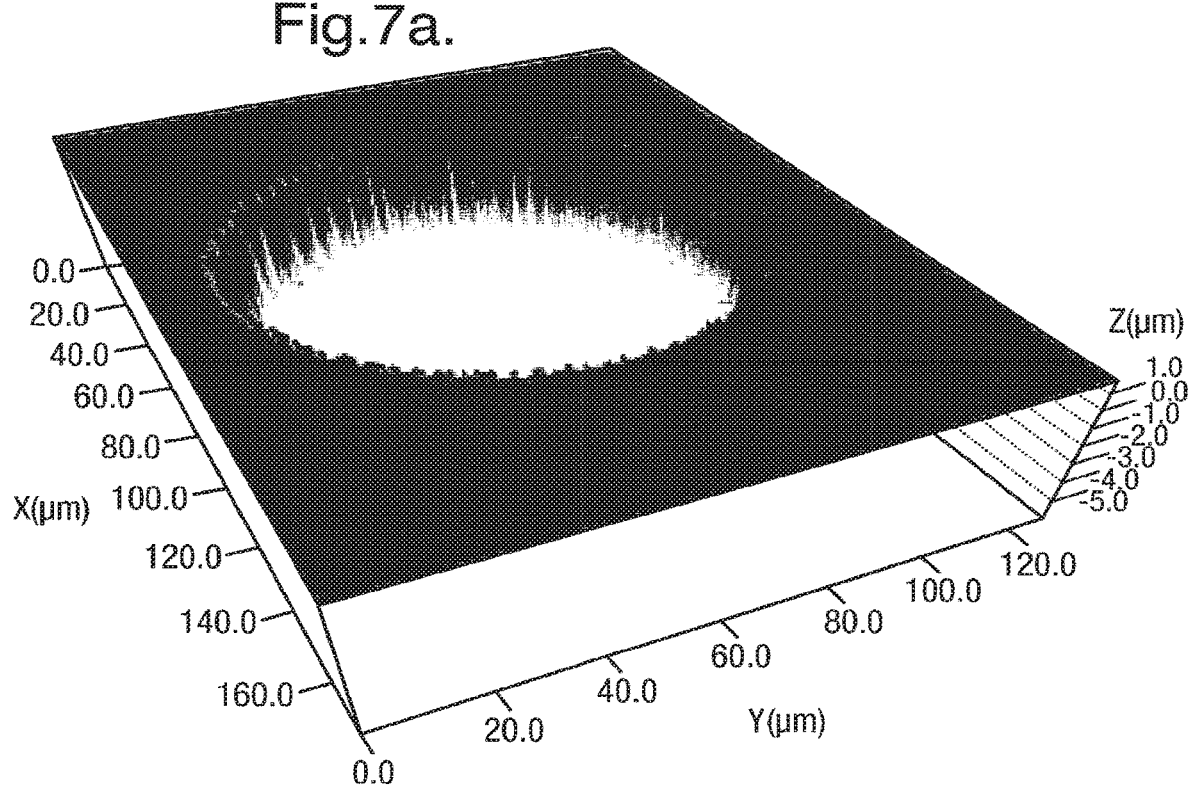
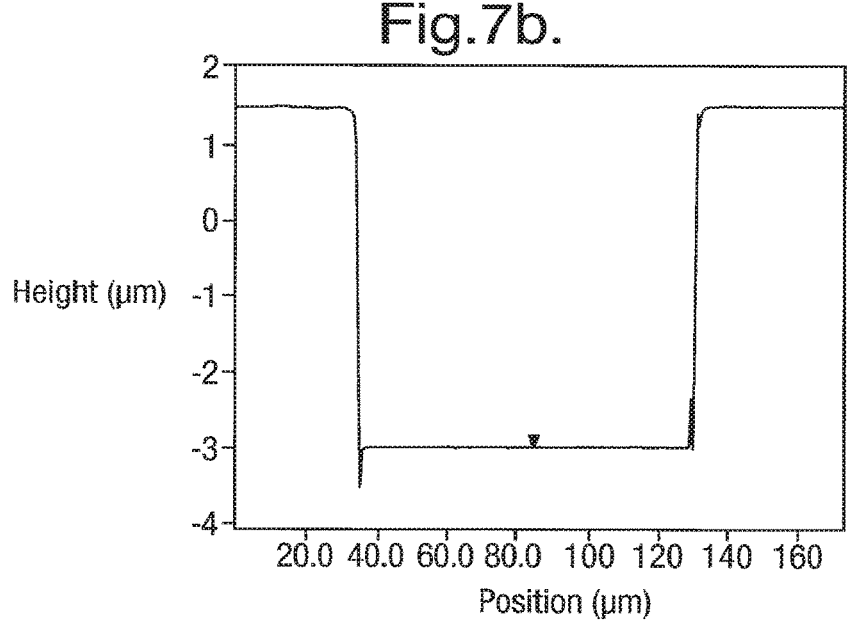

NANOPORE ARRAYS FOR SEQUENCING NUCLEIC ACIDS

RELATED APPLICATIONS

This application is a continuation of U.S. patent application Ser. No. 16/294,670 filed Mar. 6, 2019; which is a continuation of U.S. patent application Ser. No. 15/434,574 filed Feb. 16, 2017, now U.S. Pat. No. 10,416,117 issued Sep. 17, 2019; which is a continuation of U.S. patent application Ser. No. 14/302,287 filed Jun. 11, 2014, now abandoned; which is a continuation of U.S. patent application Ser. No. 12/339,956 filed Dec. 19, 2008, now abandoned; which claims the benefit of priority from U.S. Provisional Application No. 61/080,492 filed on Jul. 14, 2008; and claims priority to United Kingdom Patent Application No. 0724736.4 filed on Dec. 19, 2007, having the same title, and having the same inventors, and which are incorporated herein by reference in their entirety.

SEQUENCE LISTING

The instant application contains a Sequence Listing which has been submitted electronically in ASCII format and is hereby incorporated by reference in its entirety. Said ASCII copy, created on or about Dec. 19, 2008, is named 0157_Sequence.txt and is 1250 bytes in size.

FIELD OF THE DISCLOSURE

In one aspect, the present disclosure relates to the formation of layers of amphiphilic molecules such as lipid bilayers. It is particularly concerned with the formation of high quality layers suitable for applications requiring measurement of electrical signals with a high degree of sensitivity, for example single channel recordings and stochastic sensing for biosensor or drug screening applications. In some aspects, it is concerned with applications employing arrays of layers of amphiphilic molecules, for example lipid bilayers. In another aspect, the present disclosure relates to the performance of an electrode provided in a recess, for example for conducting electro-physiological measurements.

BACKGROUND OF THE DISCLOSURE

The potential for using cellular proteins for biosensing and drug discovery applications has long been appreciated. However there are many technical challenges to overcome in developing this technology to fully realise the potential. There is a wealth of literature on using fluorescent and optical approaches, but the focus of this document is on the measurement of electrical signals to recognise analytes in biosensing.

In one type of technique, a layer of amphiphilic molecules may be used as the layer separating two volumes of aqueous solution. The layer resists the flow of current between the volumes. A membrane protein is inserted into the layer to selectively allow the passage of ions across the layer, which is recorded as an electrical signal detected by electrodes in the two volumes of aqueous solution. The presence of a target analyte modulates the flow of ions and is detected by observing the resultant variations in the electrical signal. Such techniques therefore allow the layer to be used as a biosensor to detect the analyte. The layer is an essential component of the single molecule biosensor presented and its purpose is two-fold. Firstly the layer provides a platform for the protein which acts as a sensing element. Secondly the layer isolates the flow of ions between the volumes, the electrical resistance of the layer ensuring that the dominant contribution of ionic flow in the system is through the membrane protein of interest, with negligible flow through the bilayer, thus allowing detection of single protein channels.

A specific application is stochastic sensing, where the number of membrane proteins is kept small, typically between 1 and 100, so that the behaviour of a single protein molecule can be monitored. This method gives information on each specific molecular interaction and hence gives richer information than a bulk measurement. However, due to the small currents involved, typically a few pA, requirements of this approach are a very high resistance seal, typically at least 1 GΩ and for some applications one or two orders of magnitude higher, and sufficient electrical sensitivity to measure the currents. While the requirements for stochastic sensing have been met in the laboratory, the conditions and expertise required limit its use. In addition, the laboratory methods are laborious and time-consuming and are not easily scalable to high-density arrays, which are desirable for any commercial biosensor. Furthermore, the fragility of single bilayer membranes means that anti-vibration tables are often employed in the laboratory.

By way of background, existing techniques for forming layers of amphiphilic molecules such as lipid bilayers will be reviewed.

Several methods for forming planar artificial lipid bilayers are known in the art, most notably including folded bilayer formation (e.g. Montal & Mueller method), tip-dipping, painting, patch clamping, and water-in-oil droplet interfaces.

At present, the bulk of routine single ion channel characterisation in research labs is performed using folded bilayers, painted bilayers or tip-dip methods. These methods are used either for the ease of bilayer formation, or for the high resistive seals that can be formed (e.g. 10-100 GΩ). Tip-dip bilayers and bilayers from patch-clamping of giant unilamellar liposomes are also studied as they can be formed in a solvent free manner, which is thought to be important for the activity of some protein channels. The method of Montal & Mueller (Proc. Natl. Acad, Sci. USA. (1972), 69, 3561-3566) is popular as a cost-effective and relatively straightforward method of forming good quality folded lipid bilayers suitable for protein pore insertion, in which a lipid monolayer is carried on the water/air interface past either side of an aperture in a membrane which is perpendicular to that interface. Typically, the lipid is added to the surface of the aqueous electrolyte solution by first dissolving it in an organic solvent, a drop of which is then allowed to evaporate on the surface of the aqueous solution on either side of the aperture. Once the organic solvent has been evaporated, the solution/air interfaces are physically moved up and down past either side of the aperture until a bilayer is formed. The technique requires the presence of a hydrophobic oil applied as a pre-treatment coating to the aperture surface. The primary function of the hydrophobic oil is to form an annulus region between the bilayer and the aperture film where the lipid monolayers must come together over a distance typically between 1 and 25 μm.

Tip-dipping bilayer formation entails touching the aperture surface (e.g. a pipette tip) onto the surface of a test solution that is carrying a monolayer of lipid. Again the lipid monolayer is first generated at the solution/air interface by evaporating a drop of lipid dissolved in organic solvent applied to the solution surface. The bilayer is then formed by mechanical actuation to move the aperture into/out of the solution surface.

For painted bilayers, the drop of lipid dissolved in organic solvent is applied directly to the aperture, which is submerged in the aqueous test solution. The lipid solution is spread thinly over the aperture using a paint brush or equivalent. Thinning of the solvent results in formation of a lipid bilayer, however, complete removal of the solvent from the bilayer is difficult and consequently the bilayer formed is less stable and more noise prone during measurement.

Patch-clamping is commonly used in the study of biological cell membranes, whereby the cell membrane is clamped to the end of a pipette by suction and a patch of the membrane becomes attached over the aperture. The method has been adapted for artificial bilayer studies by clamping liposomes which then burst to leave a lipid bilayer sealing over the aperture of the pipette. This requires stable giant unilamellar liposomes and the fabrication of small apertures in glass surfaced materials.

Water-in-oil droplet interfaces are a more recent disclosure in which two aqueous samples are submerged in a reservoir of hydrocarbon oil containing lipid. The lipid accumulates in a monolayer at the oil/water interface such that when the two samples are brought into contact a bilayer is formed at the interface between them.

In any of these techniques, once the bilayer has been formed, the protein is then introduced to the bilayer either by random collision from the aqueous solution, by fusion of vehicles containing the protein, or by mechanically transporting it to the bilayer, for example on the end of a probe device such as an agar tipped rod.

There have been great efforts recently to increase the case of bilayer formation using micro fabrication. Some techniques have attempted essentially to miniaturize standard systems for folded lipid bilayers. Other techniques include bilayer formation on solid substrates or directly on electrode surfaces, through either covalent attachment or physical adsorption.

A large proportion of the devices that are capable of performing stochastic sensing form a bilayer by using a variant of the folded lipid bilayers technique or the painted bilayer technique. To date most have concentrated either on novel methods of aperture formation or on utilising the emerging technologies in micro fabrication to miniaturize the device or to create a plurality of addressable sensors.

An example is Suzuki et al., "Planar lipid bilayer reconstitution with a micro-fluidic system", Lab Chip, (4), 502-505, 2004. Herein, an aperture array is created by etching a silicon substrate, followed by a surface treatment to encourage the bilayer formation process, although the disclosed rate of successful bilayer formation is very low (two out of ten).

A more recent example is disclosed in Sandison, et al., "Air exposure technique for the formation of artificial lipid bilayers in microsystems", Langmuir, (23), 8277-8284, 2007. Herein the device fabricated from poly(methylmethacrylate) contains two distinct aqueous chambers. Problems with the reproducibility of bilayer formation are attributed to the difficulty in removing the excess hydrophobic material from the aperture, and tackled by using a period of air exposure to aid the bilayer formation process to thin the pre-treatment.

The devices of both Sandison et al. and Suzuki et al. are both miniaturised versions of a standard painted bilayer technique with two distinct fluidic chambers separated by a septum containing an aperture across which the bilayer is formed, one chamber being filled before the other. This presents a number of difficulties for scaling up the system to a large number of individually addressable bilayers, as at least one of the aqueous chambers must be a distinct chamber with no electrical or ionic connectivity to any other chamber. Sandison et al. created a device with three fluid chambers, each with separate fluidics, an approach which would be difficult to scale to large numbers of bilayers. Suzuki et al. tried to address this problem by using a hydrophobic photoresist layer to create small aqueous chambers on top of the aperture containing substrate. In this case, it is difficult to control the flow of solution across the aperture containing interface and the use of small volumes exposed to air makes the apparatus susceptible to evaporation effects. In both cited examples, the need for the individual aqueous chambers for each bilayer means that a large sample volume must be used to fill all the chambers.

An example of biosensor device using a supported lipid bilayer is disclosed in U.S. Pat. No. 5,234,566. The device is capacitive. A gated ion channel responds to an analyte, the binding of this analyte causes a change in the gating behavior of the ion channel, and this is measured via the electrical response of the membrane capacitance. To support the lipid bilayer, there is used a monolayer of alkane-thiol molecules on a gold electrode, which provides a scaffold for a lipid monolayer to self-assemble onto. This monolayer can incorporate ion channels such as gramicidin which are used as the sensing element of the device. Variations on this method have been used to create a tethered lipid bilayer onto an electrode surface to incorporate other membrane proteins. However, the approach has a number of drawbacks, the first is that the small aqueous volume present under the lipid bilayer, typically of the order of 1 nm to 10 nm thick, does not contain enough ions to perform a direct current measurement for any useful period of time. This is an effect common to nearly all tethered bilayer systems on solid supports. For recordings of any meaningful duration, an alternating current measurement must be used to overcome the ionic depletion at the electrode, but that limits the sensitivity of the device.

An example of a biosensor device using a supported lipid bilayer is disclosed in Urisu et al., "Formation of high-resistance supported lipid bilayer on the surface of a silicon substrate with micro electrodes", Nanomedicine, 2005, (1), 317-322. This device exploits the strong surface adhesion between phospholipid molecules and a $SiO_2$ surface to form a supported bilayer. A silicon oxide surface is modified, using etching techniques common in silicon chip production, to expose small channels to an electrode surface. A bilayer is then formed on the silicon oxide surface, resulting in an electrical resistance of a few MCI. In this system, the wells created by this process could not be individually addressed.

In both of the cited examples using a supported lipid bilayer, it is very difficult to form a high resistive seal using these methods. Although the resistance may be sufficient to observe a change arising from a large number of ion channels, single channel or stochastic measurements, which are inherently more sensitive, are incredibly challenging using this methodology.

There are a number of problems with the supported bilayer approach in these documents and in general, which makes this system unsuitable. The first problem lies with the resistance of the bilayer membrane which is typically about 100MA. While this may be suitable for examining protein behaviour at large protein concentrations, it is not sufficient for a high-fidelity assay based on single molecule sensing, typically requiring a resistance of at least 1 GΩ and for some applications one or two orders of magnitude higher. The second problem is the small volume of solution trapped in the short distance between the bilayer and the solid support, typically of the order of 1nm. This small volume does not contain many ions, affecting the stability of the potential across the bilayer and limiting the duration of the recording.

A number of methods have been proposed to overcome the problems with solid supported bilayers. One option is to incorporate a chemical linkage between the bilayer and the surface, either a small polyethylene glycol layer is introduced (polymer cushioned bilayers), or the lipid is chemically modified to contain a small hydrophilic linkage and reacted with the surface providing a scaffold for vehicle deposition (tethered bilayers). While these methods have increased the ionic reservoir beneath the lipid bilayer, they are inconvenient to implement and have done little to decrease the current leakage across the bilayer.

The techniques used in the silicon chip industry provide an attractive technology for creating a large number of electrodes that could be used in biosensor applications. This approach is disclosed in the related applications U.S. Pat. Nos. 7,144,486 and 7,169,272, 7,144,486 discloses a method of fabricating a microelectrode device containing microcavities etched into layers of insulator material. The devices are said to have a wide range of electrochemical applications in which electrodes in the cavities measure electrical signals. It is stated that thin films may be suspended across the cavities. Several types of film are mentioned, including being a lipid bilayer. However this is merely a proposal and there is no disclosure of any technique for forming the lipid bilayer, nor any experimental report of this. Indeed the related application U.S. Pat. No. 7,169,272, which does report experimental formation of lipid bilayers in the same type of device, discloses the supported lipid bilayers being chemically attached directly on the electrodes. This uses similar techniques to those presented in Osman et al. cited above and suffers from the same drawbacks relating to the lack of a sufficiently high resistive seal for stochastic measurements and the lack of an ionic reservoir for recording ionic flow across the bilayer system.

To summarize, the technologies described above either present methods of bilayer formation which can not reproducibly achieve high resistance, or suffer from low ionic reservoirs and are not capable of high duration direct current measurements, or require a separate fluidic chamber for each array element, limiting the scale up of that device to a high-density array. It would be desirable to reduce these problems.

BRIEF SUMMARY OF THE DISCLOSURE

According to a first aspect of the present disclosure, there is provided a method of forming a layer separating two volumes of aqueous solution, the method comprising:
 (a) providing an apparatus comprising elements defining a chamber, the elements including a body of non-conductive material having formed therein at least one recess opening into the chamber, the recess containing an electrode;
 (b) applying a pre-treatment coating of a hydrophobic fluid to the body across the recess;
 (c) flowing aqueous solution, having amphiphilic molecules added thereto, across the body to cover the recess so that aqueous solution is introduced into the recess from the chamber and so that a layer of the amphiphilic molecules forms across the recess separating a volume of aqueous solution introduced into the recess from the remaining volume of aqueous solution.

Such a method allows the formation of layers of amphiphilic molecules which are of sufficiently high quality for sensitive techniques such as stochastic sensing whilst using apparatus and techniques which are straightforward to implement.

The apparatus used is relatively simple, and comprises a body of ionically non-conductive material having formed therein at least one recess. It has been demonstrated, surprisingly, that it is possible to form a layer of the amphiphilic molecules across such a recess simply by flowing the aqueous solution across the body to cover the recess. To achieve this, a pre-treatment coating of a hydrophobic fluid is applied to the body across the recess. The pre-treatment coating assists formation of the layer. The layer is formed without any need for a complicated apparatus involving two chambers separated by a septum and requiring a complicated fluidics arrangement to achieve separate filling. This is because the method does not require the recess to be pre-filled prior to introducing aqueous solution into the chamber above. Instead, the aqueous solution is introduced into the recess from the chamber. Despite this, it is still possible to form the layer by mem control of the aqueous solution flowing into the chamber. Such flow control is a straightforward practical technique.

In some embodiments, the method may allow the formation of layers of amphiphilic molecules which are suitable for high sensitivity biosensor applications such as stochastic sensing and single channel recording. It has been demonstrated possible to form layers of high resistance providing highly resistive electrical seals, having an electrical resistance of 1 GΩ or more, typically at least 100 GΩ, which, for example, enable high-fidelity stochastic recordings from single protein pores. In some embodiments, this maybe achieved whilst trapping a volume of aqueous solution in the recess between the layer and the electrode. This maintains a significant supply of electrolyte. For example, the volume of aqueous solution is sufficient to allow stable continuous do current measurement through membrane proteins inserted in the layer.

This contrasts significantly with the known techniques described above using supported lipid bilayers.

Furthermore, the simple construction of the apparatus allows the formation of a miniaturized apparatus having an array of plural recesses and allowing the layer across each recess to be electrically isolated and individually addressed using its own electrode, such that the miniaturized array is equivalent to many individual sensors measuring in parallel from a test sample. The recesses may be relatively densely packed, allowing a large number of layers to be used for a given volume of test sample. Individual addressing may be achieved by providing separate contacts to each electrode which is simple using modem microfabrication techniques, for example lithography.

Furthermore, in some embodiments, the method may allow the formation of multiple layers of one or more amphiphilic molecules within a single apparatus across the plural recesses in an array using a very straightforward technique.

In most applications, one or more membrane proteins may be subsequently inserted into the layer. Certain membrane proteins that may be used in accordance with the disclosure are discussed in more detail below.

According to further aspects of the disclosure, there is provided an apparatus suitable for implementing such methods of formation of a layer of amphiphilic molecules.

Further details and features of the disclosure will now be described.

The amphiphilic molecules are typically a lipid. In some embodiments, the layer is a bilayer formed from two opposing monolayers of lipid. The lipids may comprise one or more lipids. The lipid bilayer may also contain additives that affect the properties of the bilayer. Certain lipids and other amphiphilic molecules, and additives that can be used in accordance with the disclosure are discussed in more detail below.

Various techniques may be applied to add the amphiphilic molecules to the aqueous solution.

A first technique is simply to add the amphiphilic molecules to the aqueous solution outside the apparatus before introducing the aqueous solution into the chamber.

A second technique comprises before introducing the aqueous solution into the chamber, to deposit the amphiphilic molecules on an internal surface of the chamber, or elsewhere in the flow path of the aqueous solution, for example in a fluidic inlet pipe connected to the inlet. In this case, the aqueous solution covers the internal surface during stop (c) whereby amphiphilic molecules are added to the aqueous solution. In this manner the aqueous solution is used to collect the amphiphilic molecules from the internal surface. Such deposition of the amphiphilic molecules has several advantages.

It allows the formation of layer of amphiphilic molecules in the absence of large amounts of organic solvent, as would typically be present if the amphiphilic molecules were added directly to the aqueous solution. This means that it is not necessary to wait for evaporation of the organic solvent before the layer can be formed. In addition, this means that the apparatus is not required to be made from materials that are insensitive to organic solvents. For instance, organic-based adhesives can be used and screen-printed conductive silver/silver chloride paste can be used to construct electrodes.

In some embodiments, the deposited amphiphilic molecules may be dried. In such embodiments, an aqueous solution may be used to rehydrate the amphiphilic molecules. This allows amphiphilic molecules to be stably stored in the apparatus before use. In some embodiments, it also avoids the need for wet storage of amphiphilic molecules. Such dry storage of amphiphilic molecules increases shelf life of the apparatus.

Several techniques may be used to insert a membrane protein into the layer of amphiphilic molecules.

A first technique is simply for the aqueous solution to have a membrane protein added thereto, whereby the membrane protein is inserted spontaneously into the layer of amphiphilic molecules. One or more membrane protein(s) may be added to the aqueous solution outside the apparatus before introducing the aqueous solution into the chamber. Alternatively a membrane protein may be deposited on an internal surface of the chamber before introducing the aqueous solution into the chamber. In this case, the aqueous solution covers the internal surface during step (c), whereby one or more membrane protein(s) is added to the aqueous solution.

A second technique is for the aqueous solution to have vesicles containing a membrane protein added thereto, whereby the membrane protein is inserted on fusion of the vesicles with the layer of amphiphilic molecules.

A third technique is to insert one or more membrane protein by carrying the membrane protein to the layer on a probe, for example an agar-tipped rod.

To form a layer of amphiphilic molecules, the aqueous solution is flowed across the body to cover the recess. Formation is improved if a multi-pass technique is applied in which aqueous solution covers and uncovers the recess at least once before covering the recess for a final time. This is thought to be because at least some aqueous solution is left in the recess which assists formation of the layer in a subsequent pass.

The pre-treatment coating is a hydrophobic fluid which assists formation of the layer by increasing the affinity of the amphiphilic molecules to the surface of the body around the recess. In general any pre-treatment that modifies the surface of the surfaces surrounding the aperture to increase its affinity to lipids may be used. Certain exemplary materials for the pre-treatment coating that may be used in accordance with the disclosure are discussed in more detail below.

To assist in the spreading of the pre-treatment coating, surfaces including either or preferably both of (a) the outermost surface of the body around the recess and (b) at least an outer part of the internal surface of the recess extending from the rim of the recess may be hydrophobic. This may be achieved by making the body with an outermost layer formed of a hydrophobic material.

Another way to achieve this is for the surfaces to be treated by a fluorine species, such as a fluorine radical, for example by treatment with a fluorine plasma during manufacture of an apparatus of the disclosure.

The application of the pre-treatment coating may leave excess hydrophobic fluid covering said electrode contained in the recess. This potentially insulates the electrode by reducing ionic flow, thereby reducing the sensitivity of the apparatus in measuring electrical signals. However various different techniques may be applied to minimize this problem.

A first technique may comprise applying a voltage across an electrode in a recess and a further electrode in the chamber sufficient to reduce the amount of excess hydrophobic fluid covering said electrode contained in the recess. This produces a similar effect to electro-wetting. The voltage is applied after flowing aqueous solution across the body to cover the recess so that aqueous solution flows into the recess. As the voltage will rupture any layer formed across the recess, subsequently the aqueous solution is flowed to uncover the recess, and then aqueous solution, having amphiphilic molecules added thereto, is flowed across the body to re-cover the recess so that a layer of the amphiphilic molecules forms across the recess.

A second technique may comprise making an inner part of the internal surface of the recess hydrophilic. Typically this may be applied in combination with making the outer part of the internal surface of the recess hydrophobic. This may be achieved by making the body with an inner layer formed of a hydrophilic material and an outermost layer formed of a hydrophobic material.

A third technique may comprise providing on the electrode a hydrophilic surface, for example a protective material, which repels the hydrophobic fluid applied in step (c) whilst allowing ionic conduction from the aqueous solution to the electrode. The protective material may be a conductive polymer, for example polypyrrole/polystyrene sulfonate. Alternatively, the protective material may be a covalently attached hydrophilic species, such as thiol-PEG.

In general, a wide range of constructional features may be employed in the apparatus to form the body of non-conductive material, the at least one recess formed therein and the other elements defining the chamber. Examples are described in further detail below.

According to a second aspect of the present disclosure, there is provided a method of improving the performance of an electrode in a recess in conducting electro-physiological measurements, the method comprising depositing a conductive polymer on the electrode.

Further according to a second aspect of the present disclosure, there is provided an apparatus for conducting electro-physiological measurements, the apparatus comprising, a body having a recess in which an electrode is located, wherein a conductive polymer is provided on the electrode.

It has been discovered that the providing a conductive polymer on an electrode in a recess can improve the performance of the electrode in conducting electro-physiological measurements. One advantage is to improve the electrode's performance as a stable electrode for conducting electro-physiological measurements. A further advantage is to increase the charge reservoir available to the electrode within the recess without increasing the volume of aqueous solution contained in the recess.

To allow better understanding, embodiments of the present disclosure will now be described by way of non-limitative example with reference to the accompanying drawings.

BRIEF DESCRIPTION OF THE DRAWINGS

Some embodiments of the disclosure may be understood by referring, in part, to the present disclosure and the accompanying drawings, wherein:

FIGS. 7A and 7B are 3D and 2D LP profiles, respectively, of a recess formed using photolithography;

DETAILED DESCRIPTION OF THE DISCLOSURE

Figure 1:
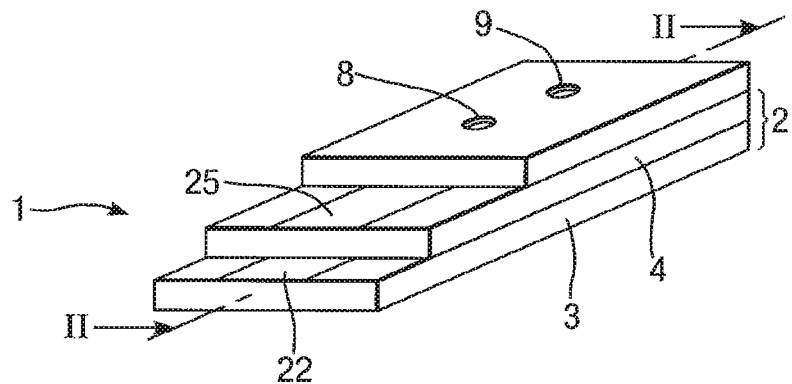
FIG. 1 is a perspective view of an apparatus.
Figure 2:
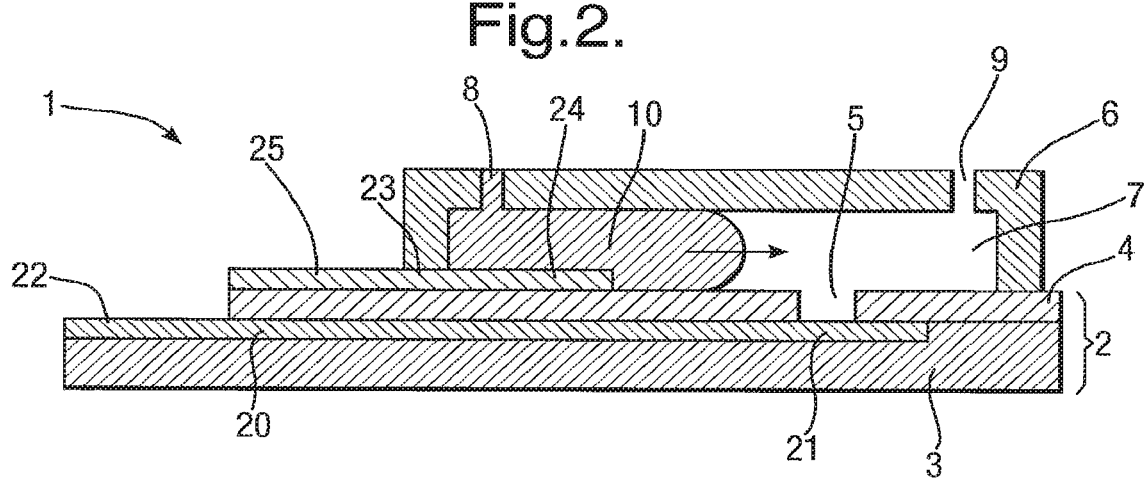
FIG. 2 is a cross-sectional view of the apparatus of FIG. 1, taken along line II-II in FIG. 1, and showing the introduction of an aqueous solution.
Figure 3:
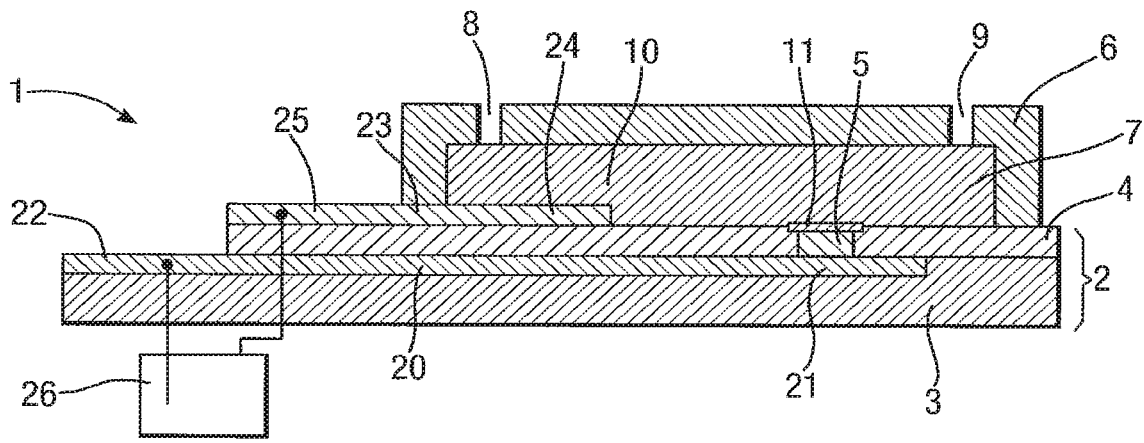
FIG. 3 is a cross-sectional view of the apparatus, similar to that of FIG. 2 but showing the apparatus full of aqueous solution.

An apparatus 1 which may be used to form a layer of amphiphilic molecules is shown in FIG. 1. The apparatus 1 includes a body 2 having layered construction as shown in FIGS. 2 and 3 comprising a substrate 3 of non-conductive material supporting a further layer 4 also of nonconductive material. in the general case, there may be plural further layers 4, as described further below.

A recess 5 is formed in the further layer 4, in particular as an aperture which extends through the further layer 4 to the substrate 3. In the general case, there may be plural recesses 5, as described further below.

The apparatus 1 further includes a cover 6 which extends over the body 2. The cover 6 is hollow and defines a chamber 7 which is closed except for an inlet 8 and an outlet 9 each formed by openings through the cover 6. The lowermost wall of the chamber 7 is formed by the further layer 4 in FIG. 2, but as an alternative the further layer 4 could be shaped to provide side walls.

As described further below, in use aqueous solution 10 is introduced into the chamber 7 and a layer 11 of amphiphilic molecules is formed across the recess 5 separating aqueous solution 10 in the recess 5 from the remaining volume of aqueous solution in the chamber 7. The apparatus includes the following electrode arrangement to allow measurement of electrical signals across the layer 11 of amphiphilic molecules.

Use of a chamber 7 which is closed makes it very easy to flow aqueous solution 10 into and out of the chamber 7. This is done simply by flowing the aqueous solution 10 through the inlet S as shown in FIG. 2 until the chamber 7 is full as shown in FIG. 3. During this process, gas (typically air) in the chamber 7 is displaced by the aqueous solution 10 and vented through the outlet 9. For example, a simple fluidics system attached to the inlet 8 may be used. This may be as simple as a plunger, although more complicated systems may be used to improve the control. However, the chamber 7 is not necessarily closed and may be open, for example by forming the body 2 as a cup.

The substrate 3 has a first conductive layer 20 deposited on the upper surface of the substrate 3 and extending under the further layer 4 to the recess 5. The portion of the first conductive layer 20 underneath the recess 5 constitutes an electrode 21 which also forms the lowermost surface of the recess 5. The first conductive layer 20 extends outside the further layer 4 so that a portion of the first conductive layer 20 is exposed and constitutes a contact 22.

The further layer 4 has a second conductive layer 23 deposited thereon and extending under the cover 6 into the chamber 7, the portion of the second conductive layer 23 inside the chamber 7 constituting an electrode 24. The second conductive layer 23 extends outside the cover 6 so that a portion of the second conductive layer 23 is exposed and constitutes a contact 25.

The electrodes 21 and 24 make electrical contact with aqueous solution in the recess 5 and chamber 7. This allows measurement of electrical signals across the layer 11 of amphiphilic molecules by connection of an electrical circuit 26 to the contacts 22 and 25. The electrical circuit 26 may have basically the same construction as a conventional circuit for performing stochastic sensing across a lipid bilayer formed in a conventional cell by the Montal & Mueller method.

Figure 12:
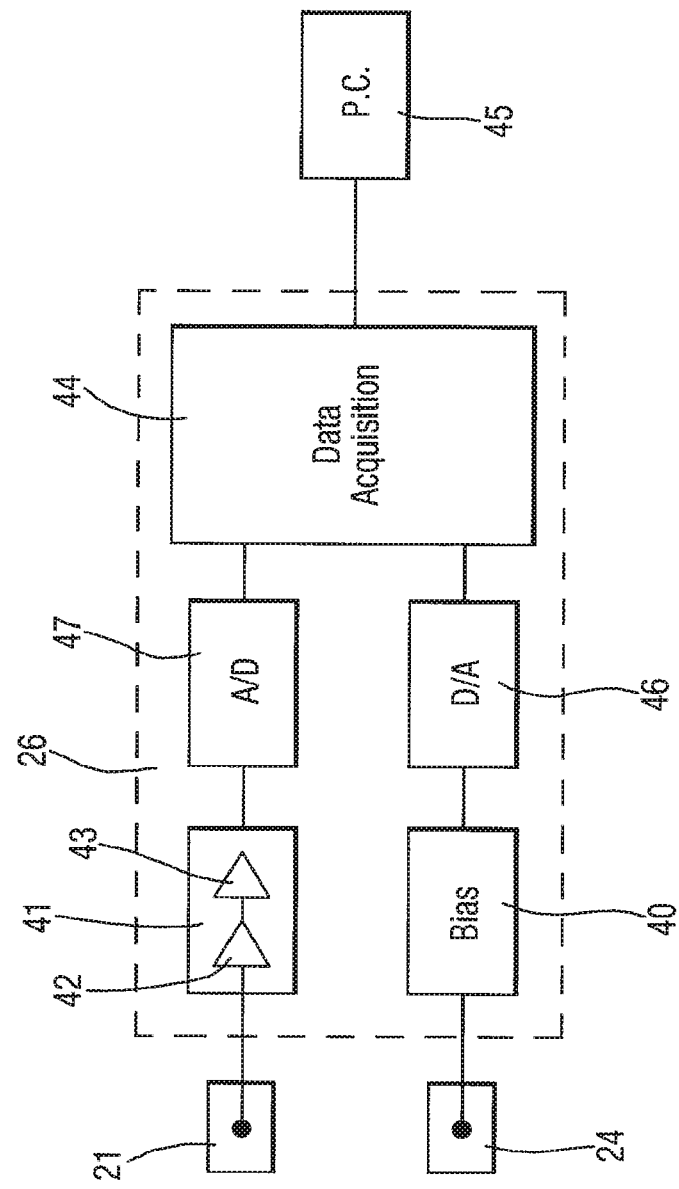
FIG. 12 is a diagram of an electrical circuit.

An example design of the electrical circuit 26 is shown in FIG. 12. The primary function of the electrical circuit 26 is to measure the electrical current signal developed between the electrodes 21 and 24 to provide a meaningful output to the user.

This may be simply an output of the measured signal, but in principle could also involve further analysis of the signal. The electrical circuit 26 needs to be sufficiently sensitive to detect and analyze currents which are typically very low. By way of example, an open membrane protein might typically pass current of 100 pA to 200 pA with a 1 M salt solution.

In this implementation, the electrode 24 in the chamber 7 is used as a reference electrode and the electrode 21 in the recess 5 is used as a working electrode. Thus the electrical circuit 26 provides the electrode 24 with a bias voltage potential relative to the electrode 21 which is itself at virtual ground potential and supplies the current signal to the electrical circuit 26.

The electrical circuit 26 has a bias circuit 40 connected to the electrode 24 in the chamber 7 and arranged to apply a bias voltage which effectively appears across the two electrodes 21 and 24.

The electrical circuit 26 also has an amplifier circuit 41 connected to the electrode 21 in the recess 5 for amplifying the electrical current signal appearing across the two electrodes 21 and 24. Typically, the amplifier circuit 41 consists of a two amplifier stages 42 and 43.

The input amplifier stage 42 connected to the electrode 21 converts the current signal into a voltage signal.

The input amplifier stage 42 may comprise transimpedance amplifier, such as an electrometer operational amplifier configured as an inverting amplifier with a high impedance feedback resistor, of for example 500MΩ, to provide the gain necessary to amplify the current signal which typically has a magnitude of the order of tens to hundreds of pico-amps.

Alternatively, the input amplifier stage 42 may comprise a switched integrator amplifier. This is preferred for very small signals as the feedback element is a capacitor and virtually noiseless. In addition, a switched integrator amplifier has wider bandwidth capability. However, the integrator does have a dead time due to the necessity to reset the integrator before output saturation occurs. This dead time may be reduced to around a microsecond so is not of much consequence if the sampling rate required is much higher. A transimpedance amplifier is simpler if the bandwidth required is smaller.

Generally, the switched integrator amplifier output is sampled at the end of each sampling period followed by a reset pulse. Additional techniques can be used to sample the start of integration eliminating small errors in the system.

The second amplifier stage 43 amplifies and filters the voltage signal output by the first amplifier stage 42. The second amplifier stage 43 provides sufficient gain to raise the signal to a sufficient level for processing in a data acquisition unit 44. For example with a 500 MΩ feedback resistance in the first amplifier stage 42, the input voltage to the second amplifier stage 43, given a typical current signal of the order of 100 pA, will be of the order of 50 mV, and in this case the second amplifier stage 43 must provide a gain of 50 to raise the 50 mV signal range to 2.5V.

The electrical circuit 26 includes a data acquisition unit 44 which may be a microprocessor running an appropriate program or may include dedicated hardware.

The data acquisition unit 44 may be a card to be plugged into a computer 45 such as a desktop or laptop. In this case, the bias circuit 40 is simply formed by an inverting amplifier supplied with a signal from a digital-to-analog converter 46 which may be either a dedicated device or a part of the data acquisition unit 44 and which provides a voltage output dependent on the code loaded into the data acquisition unit 44 from software. Similarly, the signals from the amplifier circuit 41 are supplied to the data acquisition card 40 through an analog-to-digital converter 47.

Figure 13:
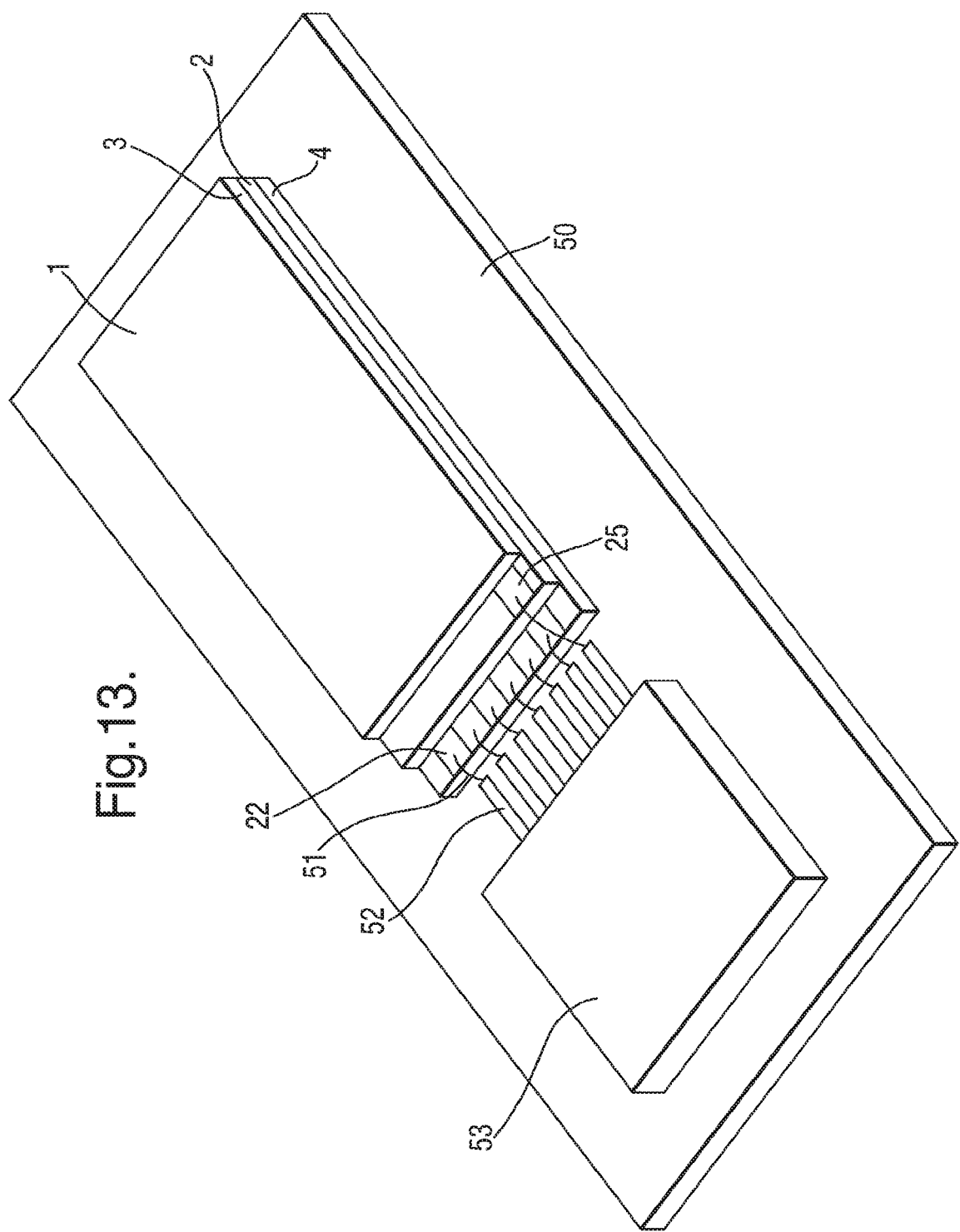
FIG. 13 is a perspective view of the apparatus and electrical circuit mounted on a printed circuit board.

The various components of the electrical circuit 26 may be formed by separate components or any of the components may be integrated into a common semiconductor chip. The components of the electrical circuit 26 may be formed by components arranged on a printed circuit board. An example of this is shown in FIG. 13 wherein the apparatus 1 is bonded to a printed circuit board 50 with aluminum wires 51 connecting from the contacts 22 and 25 to tracks 52 on the printed circuit board. A chip 53 incorporating the electrical circuit 26 is also bonded to the printed circuit board 50. Alternatively the apparatus 1 and the electrical circuit 26 may be mounted on separate printed circuit boards.

In the case that the apparatus 1 contains plural recesses 5, each having a respective electrode 21, then the electrical circuit 26 is modified essentially by replicating the amplifier circuit 41 and A/D converter 47 for each electrode 21 to allow acquisition of signals from each recess 5 in parallel. In the case that the input amplifier stage 42 comprises switched integrators then those would require a digital control system to handle the sample-and-hold signal and reset integrator signals. The digital control system is most conveniently configured on a field-programmable-gate-array device (FPGA). In addition the FPGA can incorporate processor-like functions and logic required to interface with standard communication protocols i.e. USB and Ethernet.

Figure 14:
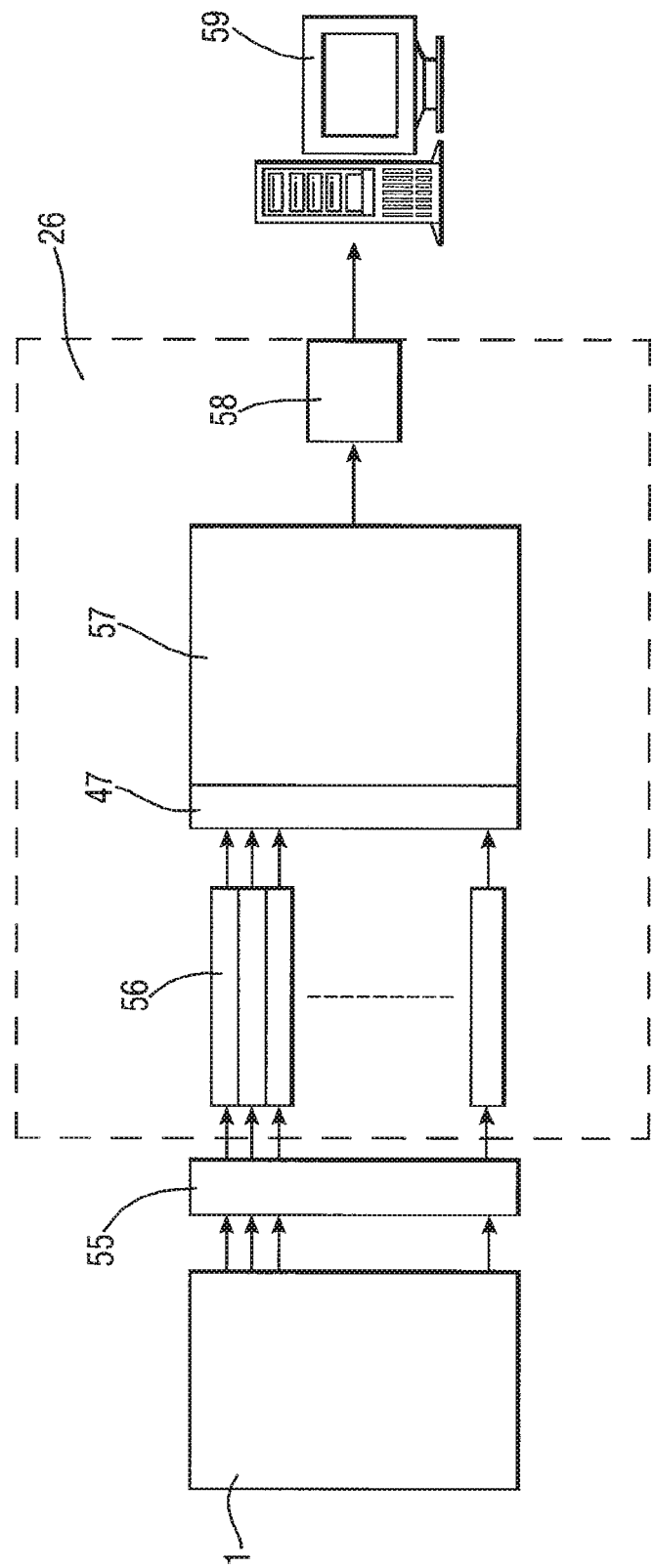
FIG. 14 is a diagram of an electrical circuit for acquiring plural signals in parallel.

FIG. 14 shows a possible architecture of the electrical circuit 26 and is arranged as follows. The respective electrodes 21 of the apparatus 1 are connected to the electrical circuit 26 by an interconnection 55, for example the aluminum wires 51 and the printed circuit board in the arrangement of FIG. 13. In the electrical circuit 26, the amplifier circuits 41 may be formed in one or more amplifier chips 56 having plural channels. The signals from different electrodes 21 may be on separate channels or multiplexed together on the same channel. The outputs of the one or more amplifier chips 56 are supplied via the A/D converter 47 to a programmable logic device 57 for receiving the signal on each channel. For example to handle signals from an apparatus having 1024 recesses, the programmable logic device 57 might operate at a speed of the order of 10Mbits/s. The programmable logic device 57 is connected via an interface 58, for example a USB interface, to a computer 59 to supply the signals to the computer 59 for storage, display and further analysis.

During use the apparatus 1 may be enclosed in a Faraday cage to reduce interference.

Various materials for the components of the apparatus 1 will now be discussed. The materials for each component of apparatus 1 are determined by the properties required to enable the component to function correctly during operation, but the cost and manufacturing throughput are also considered. All materials may be chosen to provide sufficient mechanical strength to allow robust handling, and surfaces compatible with bonding to the subsequent layers.

The material of the substrate 3 is chosen to provide a rigid support for the remainder of the apparatus 1. The material is also chosen to provide a high resistance and low capacitance electrical insulation between adjacent electrodes 21 when there are plural recesses 5. Possible materials include without limitation: polyester (e.g. Mylar), or another polymer; or silicon, silicon nitride, or silicon oxide. For example, the substrate may comprise a silicon wafer with a thermally grown oxide surface layer.

The material of the further layer 4 (or in the general case layers) are chosen to provide a high resistance and low capacitance electrical insulation between the electrodes 21 and 24 and also, when there are plural recesses 5, between the electrodes 21 and 24 of adjacent recesses 5. Also the surface of the further layer 4 should be chemically stable both to the pre-treatment coating applied before operation (as discussed below) and to the aqueous solution 10. Lastly, the further layer 4 should be mechanically robust in order to maintain its structural integrity and coverage of the first conductive layer 20, and should be suitable for subsequent attachment of the cover 6.

The following is a list of possible materials for the further layer 4, together with thicknesses which have been successfully employed experimentally, although these thicknesses are not limitative: photoresist (e.g. SUB photoresist or Cyclotene) with a variety of thicknesses; polycarbonate, 6 µm thick film; PVC, 7 µm thick film; polyester, 50 µm thick film; adhesive backed polyester, 25 µm and 50 µm thick film; thermal laminating films, e.g. Magicard 15 µm thick and Murodigital 35 µm; or a screen-printed dielectric ink.

Advantageously, surfaces including (a) the outermost surface of the body 2 around the recess and (b) the outer part of the internal surface of the recess 5 extending from the rim of the recess 5 are hydrophobic. This assists in the spreading of the pre-treatment coating and therefore also formation of a lipid bilayer. One particular way to achieve this is to modify these surfaces by a fluorine species. Such a fluorine species is any substance capable of modifying the surfaces to provide a fluorine-containing layer. The fluorine species is preferably one containing fluorine radicals. For example the modification may be achieved by treating the body 2 with a fluorine plasma, for example a $CF_4$ during manufacture.

The conductive layers 20 and 23 will now be discussed further.

The material of the electrodes 21 and 24 should provide an electrochemical electrode in contact with the aqueous solution 10, enabling measurement of low currents, and should be stable to the pre-treatment coating and aqueous solution 10. The material of the remainder of the conductive layers 20 and 23 (usually but not necessarily the same as the electrodes 21 and 24) also provides electrical conductance from the electrodes to the contacts 22 and 25. The first conductive layers 20 will also accept bonding of the further layers 4. The conductive layers 20 and 23 can be constructed with plural overlapping layers and/or an appropriate surface treatment. One possible material is platinum, coated with silver at the area exposed to the test solution and then silver chloride formed on top of the silver. Possible materials for the first conductive layer 20 include without limitation: Silver/silver chloride electrode ink; silver with or without a surface layer, for example of silver chloride formed by chloridisation or of silver fluoride formed by fluoridisation; gold with or without redox couple in solution; platinum with or without redox couple in solution; ITO with and without redox couple in solution; gold electrochemically coated with conductive polymer electrolyte; or platinum electrochemically coated with conductive polymer electrolyte. Possible materials for the second conductive layer 23 include without limitation: silver/silver chloride electrode ink; silver wire; or chloridised silver wire.

Some specific examples of include: the substrate 3 being silicon and the conductive layer 20 being a metal conductor (diffusion or polysilicon wires are poor methods) buried in a silicon oxide insulating layer (e.g. using typical semiconductor fabrication technology); the substrate 3 being glass and the conductive layer 20 being metal conductors (e.g. using typical LCD display technology); or the substrate 3 being a polymeric substrates and the conductive layer 20 being an ablated metal or printed conductor (e.g. using typical glucose biosensor technology).

The requirements for the material of the cover 6 are to be easily attached to create a seal for the chamber 7, to be compatible with both the pro-treatment coating and the aqueous solution 10. The following are possible materials, together with thicknesses which have been successfully employed experimentally, although these thicknesses are not limitative: silicone rubber, 0.5, 1.0, 2.0 mm thick; polyester, 0.5 mm thick; or PMMA (acrylic) 0.5 mm to 2 mm thick.

Various methods of manufacturing the apparatus 1 will now be discussed. In general terms, the layered construction of the apparatus 1 is simple and easy to form by a variety of methods. Three different fabrication technologies which have actually been applied are: lamination of polymer films; printed circuit board manufacture with high resolution solder mask formation and photolithography using silicon wafers or glass.

An example of a lamination process is as follows.

The substrate 3 is a 250 µm thick polyester sheet (Mylar), and the first conductive layer 20 is deposited by either: screen printing silver/silver chloride electrode ink; adhesion of metal foil; or vapour deposition (sputtering or evaporation).

The further layer 4 is then laminated onto the substrate 3 by either: a pressure-sensitive adhesive; a thermally activated adhesive; or using the wet silver/silver chloride ink as the adhesive painted directly onto the dielectric before lamination (referred to as "painted electrodes"). The aperture in the further layer 4 that forms the recess 5 is created with 5-100 µm diameter either before or after lamination to the substrate 3 by either: electrical discharge (sparking); or laser drilling, for example by an excimer, solid state or $CO_2$ laser. An apparatus created by lamination of polymer films sometimes requires an additional sparking step to activate the electrodes prior to use. The second conductive layer 23 is formed on top of the further layer 4 by screen printing. The cover 6 is laminated on top using pressure sensitive adhesive.

An example of a process employing photolithography using silicon wafers is as follows.

The substrate 3 is a silicon wafer with an oxide surface layer. The first conductive layer 20 is formed by gold, silver, chloridised silver, platinum or ITO deposited onto the substrate 3. Photoresist (e.g. SUS) is then spin-coated over the substrate 3 to form the further layer 4. The recess 5 is formed with 5-100 µm diameter by removal of the photoresist following UV exposure using a mask to define the shape of the recess 5. The second conductive layer 23 is formed on top of the further layer 4, for example by screen printing. The cover 6 is laminated on top using pressure sensitive adhesive.

The ability to use this type of process is significant because it allows the apparatus to be formed on silicon chips using standard silicon wafer processing technology and materials.

The electrodes 21 and 24 will now be discussed further.

For stable and reliable operation, the electrodes 21 and 24 should operate at the required low current levels with a low over-potential and maintain their electrode potential value over the course of the measurement. Further, the electrodes 21 and 24 should introduce a minimum amount of noise into the current signal. Possible materials for the electrodes 21 and 24 include without limitation: Silver/silver chloride electrode ink; silver with or without a surface layer, for example of silver chloride formed by chloridisation or of silver fluoride formed by fluoridisation; gold with or without redox couple in solution; platinum with or without redox couple in-solution; ITO with and without redox couple in solution; palladium hydride, gold electrochemically coated with conductive polymer electrolyte; or platinum electrochemically coated with conductive polymer electrolyte.

Silver is a good choice for the material of electrodes 21 and 24 but is difficult to incorporate in a silicon wafer manufacturing process due to its tendency to undergo oxidation on exposure to light, air and high temperatures. To avoid this problem it is possible to manufacture the apparatus with an inert conductive material (e.g. Pt or Au) in the recess, and then change the surface type or properties of the inert conductive material using methods including but not limited to electroplating, electropolymerisation, electroless plating, plasma modification, chemical reaction, and other coating methods known in the art.

Electroplating of silver may be achieved, for example, using a modified version of the method of Polk et al., "Ag/AgCl microelectrodes with improved stability for microfluidics", Sensors and Actuators B 114 (2006) 239-247. A plating solution is prepared by addition of 0.4Ig of silver nitrate to 20 ml of IM ammonium hydroxide solution. This is rapidly shaken to avoid precipitation of the insoluble silver oxide, and to facilitate the formation of the diammine silver complex. The solution is always fresh to avoid fall in plating efficiency. The plating is performed using conventional equipment, connecting the electrode 21 as the cathode and using a platinum electrode is used as the anode. For example in the case of plating on Pt electrodes, a potential of −0.58V is applied to the cathode, with the anode being held at ground potential, whereas in the case of plating on Au electrodes, the potential is held at −0.48V with respect to ground. A target charge of $5.1 \times 10^3 C/m^2$ has been found empirically to result in a silver deposition of between 1p m and 2 µm for a 100 µm diameter electrode, typically taking of the order of 60 s.

In performing such plating it is desirable to achieve uniform penetration of the aqueous plating solution to the bottom of the recess 5. In the case that the layer 4 is formed from a naturally hydrophobic material (e.g. SU8 photoresist) and in order to ensure uniform wetting of the recess, desirably the degree of hydrophilicity can be increased. Three methods to achieve this are as follows. A first method is application of a lipid to the surface of the layer 4, so that the lipid acts as a surfactant, facilitating the entry of the plating solution. A second method is exposure of the layer 4 to oxygen plasma which activates the material of the layer and produces hydrophilic functional groups. This produces a well defined hydrophilic and clean surface. A third method is to add ethanol to the plating solution.

Where the electrode 21 is made of silver (or indeed other metals), the outer surface of the electrode is desirably converted to a halide, in order for the electrode 21 to function efficiently as a provider of a stable reference potential. In common usage, the halide used is chloride, since the conversion of silver to silver chloride is relatively straightforward to achieve, for example by electrolysis in a solution of hydrochloric acid. Alternative chemical methods avoiding the use of a potentially corrosive acid which may affect the surface condition of the layer 4 include a) sweeping voltammetry in 3 M sodium chloride solution, and b) a chemical etching by immersion of the electrode 21 in 50 mM ferric chloride solution.

An alternative halogen for the hyalinization is fluorine. The choice of fluorine has the significant advantage that the silver fluoride layer can be formed in the same step as modification of surfaces (a) and (b) of the body 2 to make them hydrophobic, as discussed above. For example this may be achieved during manufacture of the apparatus 1 by treatment of the body 2 by a fluorine plasma for example a $CF_4$ plasma.

This is effective to modify the surfaces of the body 2, particularly in the case that the layer 4 is a photoresist such as SU8 to achieve a sufficient degree of hydrophobicity to support the formation of a stable lipid bilayer. At the same time exposure to the fluorine plasma converts the metal of the electrode 21 into an outer layer of metal fluoride.

There will now be discussed some possible adaptations of the electrode 21 in the recess 5 as alternatives to the use of a fluorine plasma as discussed above.

The electrode 21 may be electrochemically modified to change the surface-type. This allows use of additional materials with good bulk properties but poor surface properties, such as gold. Possible electrochemical surface modifications include without limitation: silver electroplating; electrochemical chloridisation of silver; electropolymerisation of a polymer/polyelectrolyte.

Figure 4:
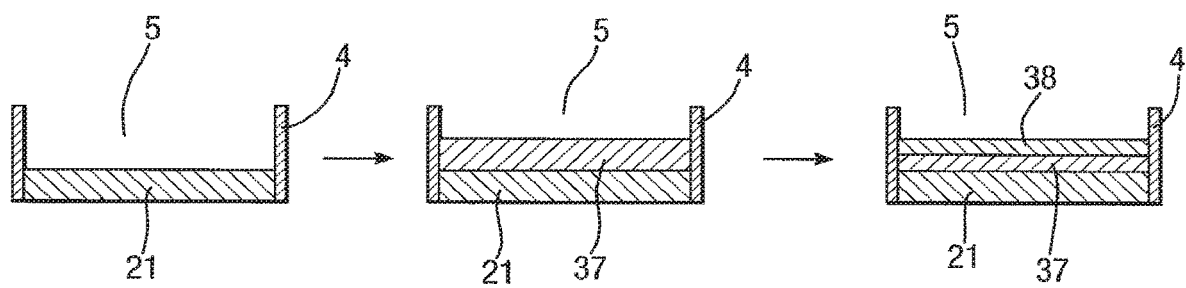
FIG. 4 is sequence of a cross-sectional, partial views of the recess in the apparatus over an electrochemical electrode modification process.

By way of further example, one possible sequence of modification is shown in FIG. 4 in which a coating 37 of silver is formed on the electrode 21 formed of gold or platinum by electrochemical deposition. Electroplating may typically be performed in 0.2 M $AgNO_2$, 2 M KI, 0.5 mM $Na_2S_2O_3$ at −0.48 V using a standard single liquid junction Ag/AgCl reference electrode and a platinum counter electrode. A typical thickness of the coating 37 is estimated to be 750 nm with a deposition time of about 50 s and about 50 µC charge passed. Subsequently a chloridised layer 38 is formed by chloridisation, typically at +150 mV in 0.1 M HC for 30 s.

Another possible surface modification is to apply a conductive polymer. The conductive polymer may be any polymer which is conductive. A suitable conductive polymer will have mobile charge carriers. Typically such a conductive polymer will have a backbone having delocalised electrons which are capable of acting as charge carriers, allowing the polymer to conduct. The conductive polymer may be doped to increase its conductivity, for example by a redox process or by electrochemical doping. Suitable conductive polymers include, without limitation: polypyrroles, polyacetylenes, polythiophenes, polyphenylenes, polyanilines, polyfluorenes, poly(3-alkylthiophene)s, polytetrathiafulvalenes, polynaphthalenes, poly(p-phenylene sulfide)s, polyindoles, polythionincs, polyethylenedioxythiophenes, and poly(para-phenylene vinylene)s.

One possible conductive polymer is a polypyrrole, which may be doped, for example with polystyrene sulfonate. This may be deposited, for example, on an electrode 21 of gold by electrooxidizing an aqueous solution of 0.1 M pyrrole+90 mM polystyrene sulfonate in 0.1 M KCl at +0.80V vs. Ag/AgCl reference electrode. The estimated thickness of polymer deposited is 1 µm at 30 µC, based on an assumption that 40 mC/cm² of charge produces a film of thickness around 0.1 µm. The polymerization process can be represented as follows, where PE stands for polystyrene sulfonate:

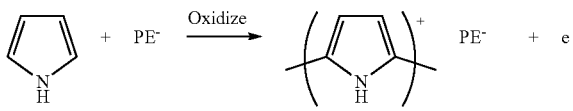

One advantage of using a conductive polymer deposited on an inert electrode, such as polypyrrole doped with polystyrene, electropolymerised onto gold or platinum, is to improve the electrode's performance as a stable electrode for conducting electrophysiological measurements. A further advantage is to increase the charge reservoir available to the electrode within the recess without increasing the volume of aqueous solution contained in the recess. These advantages are generally applicable when conducting electrophysiological measurements using an electrode in a recess, such as the electrode 21 in the apparatus 1.

Other advantages of using a conductive polymer on the electrode 21 in the recess 5 of the apparatus 1 include but are not limited to control of the hydrophilic nature of the electrode surface to aid wetting of the electrode surface by the aqueous buffer solution and similarly prevention of blocking of the electrode by the chemical pre-treatment prior to bilayer formation.

Figure 34A:
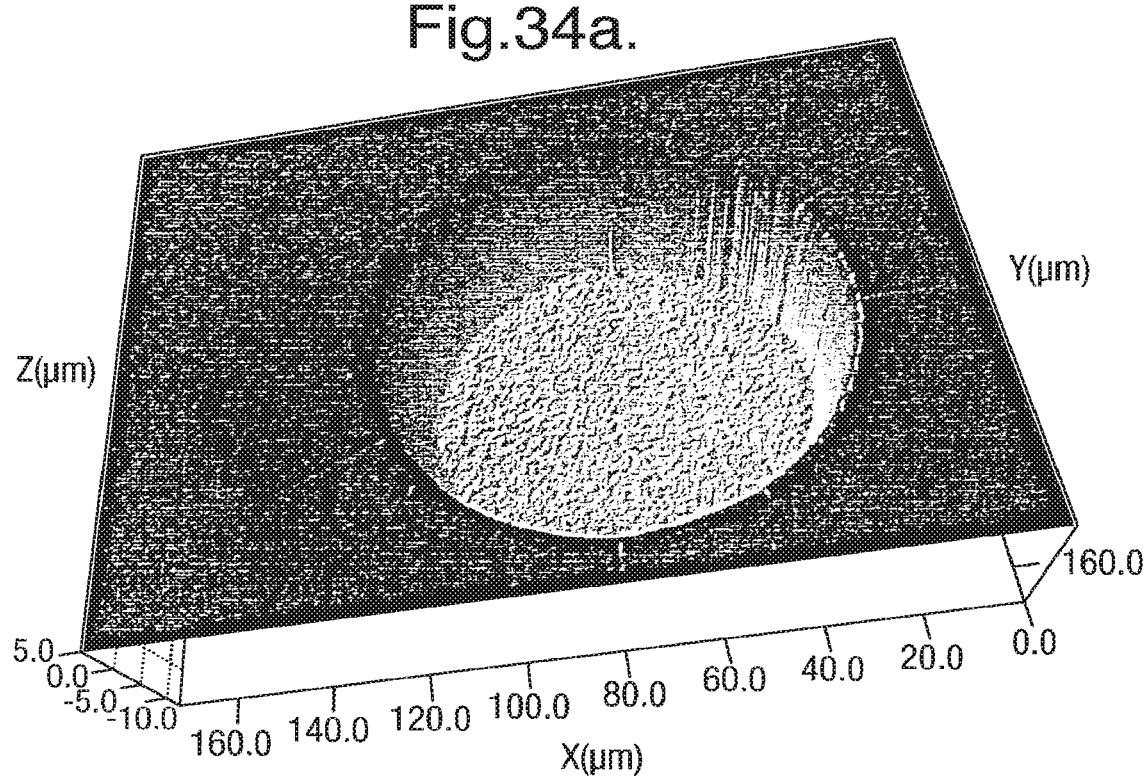
FIGS. 34A and 34B are 3D- and 2D surface profiles of a recess having an electrode modified by electropolymerisation of polypyrrole, measured by profilometry.
Figure 34B:
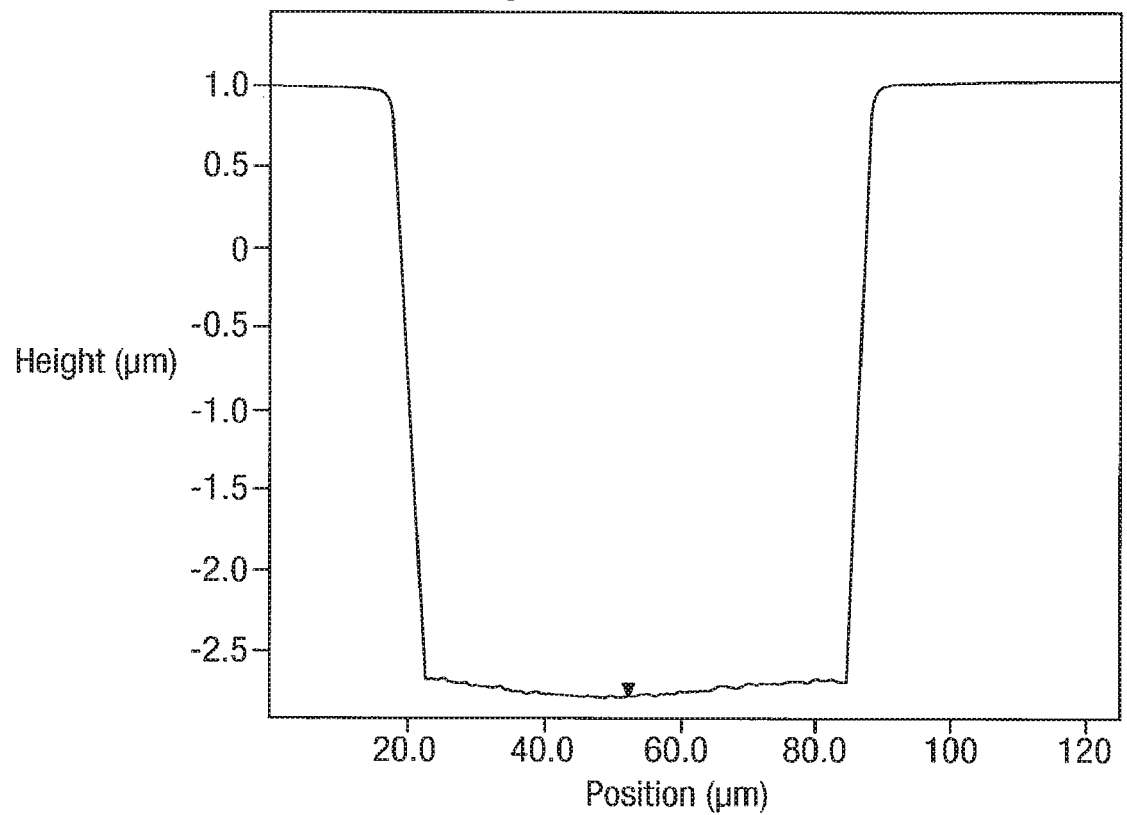
Figure 35:
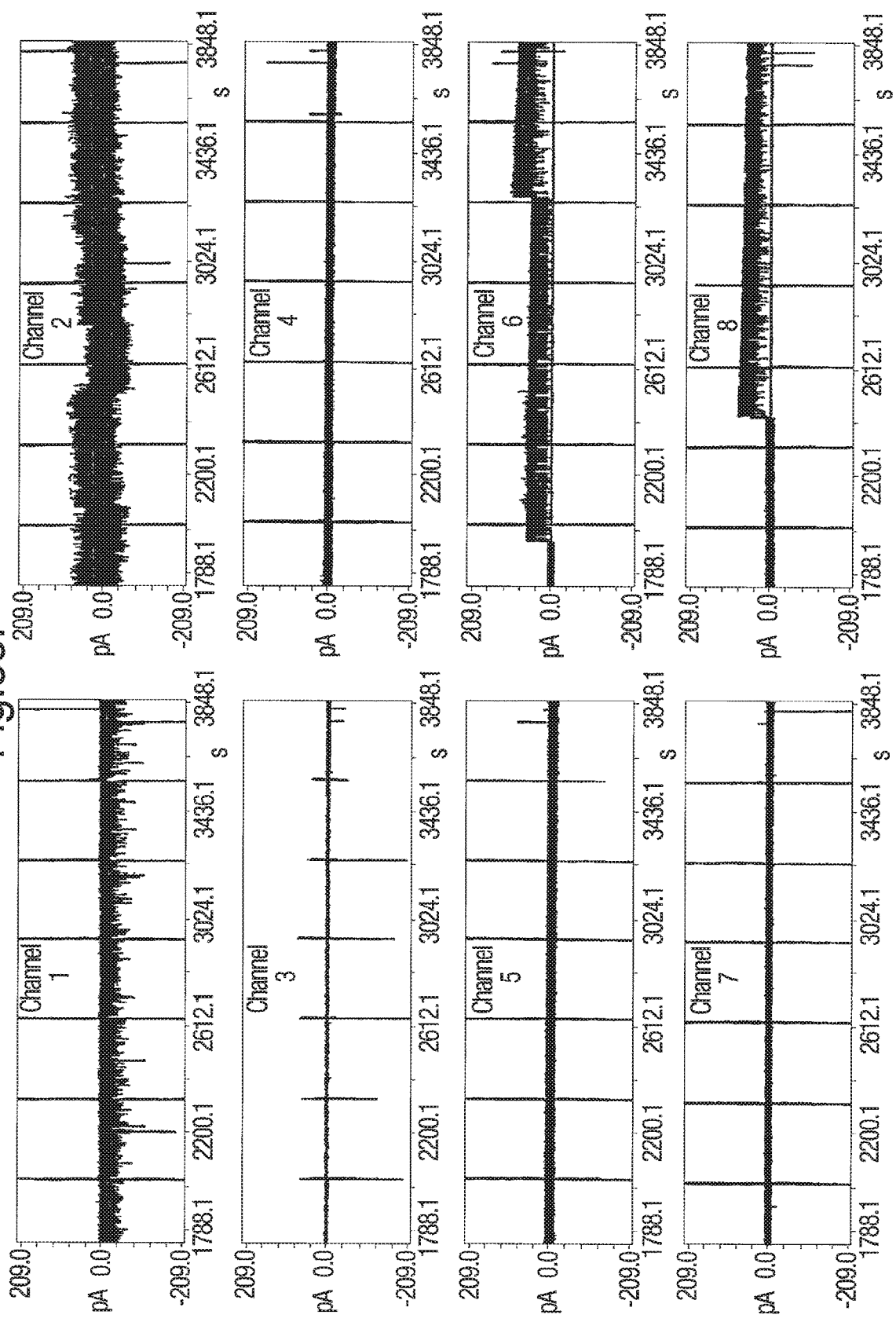
FIG. 35 is a graph of current recorded on an array of recesses having an electrode modified by electropolymerisation of polypyrrole.

FIGS. 34A and 34B are 3D and 2D surface profiles of an example electrode modified by electropolymerisation of polypyrrole, measured by profilometry. The thickness of electrochemically deposited polymer film in this example is about 2 µm. FIG. 35 shows the current recorded on an array of recesses modified by electropolymerisation of polypyrrole, showing stable lipid bilayers and single molecule detection of cyclodextrin from inserted protein pores.

In all embodiments, an alternative to the second conductive layer 23 is to form an electrode in the chamber 7 simply by insertion through the cover 6 of a conductive member, such as a chloridised silver wire.

In order to characterise the electrodes 21, visualisation of recesses 5 formed in a body 2 has been conducted using optical microscopy (OM), scanning electron microscopy (SEM), and laser profilometry (LP).

Figure 5:
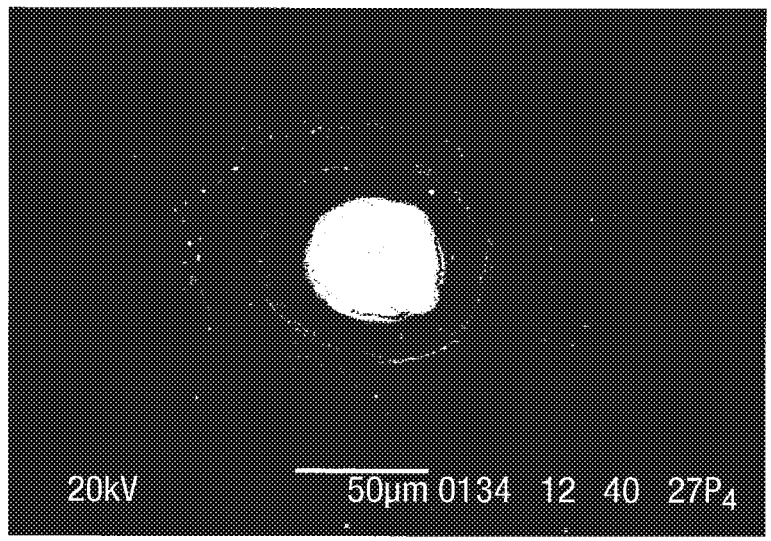
FIG. 5 is an SEM image of a recess formed by $CO_2$ laser drilling.

FIG. 5 shows an SEM image of a recess 5 formed by drilling with a CO₂ laser in an apparatus 1 formed by lamination of polymer layers, with subsequent application of electrical discharge to activate the electrode 21. The image illustrates that the geometry of the recess 5 is poorly defined using this method of formation, with considerable surface damage therearound and variability in diameter, although it is hoped this maybe improved through optimisation of the laser characteristics.

Figure 6:
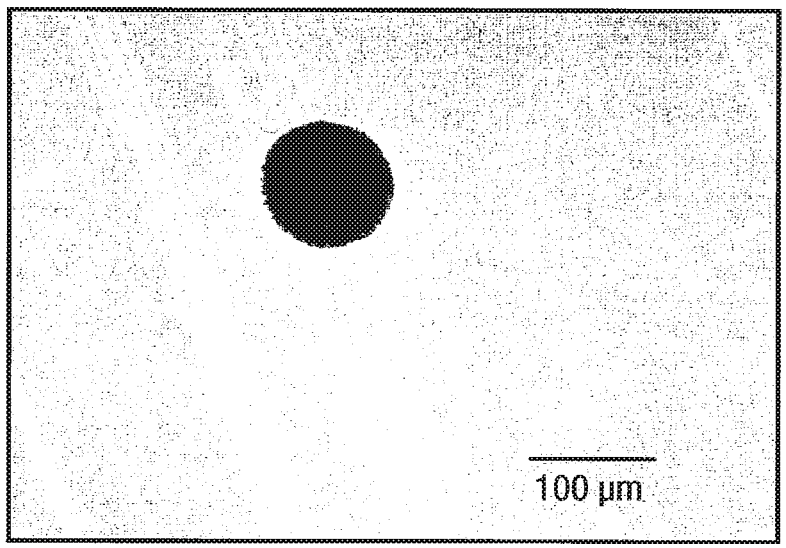
FIG. 6 is an OM image of a recess formed using photolithography.
Figure 8A:
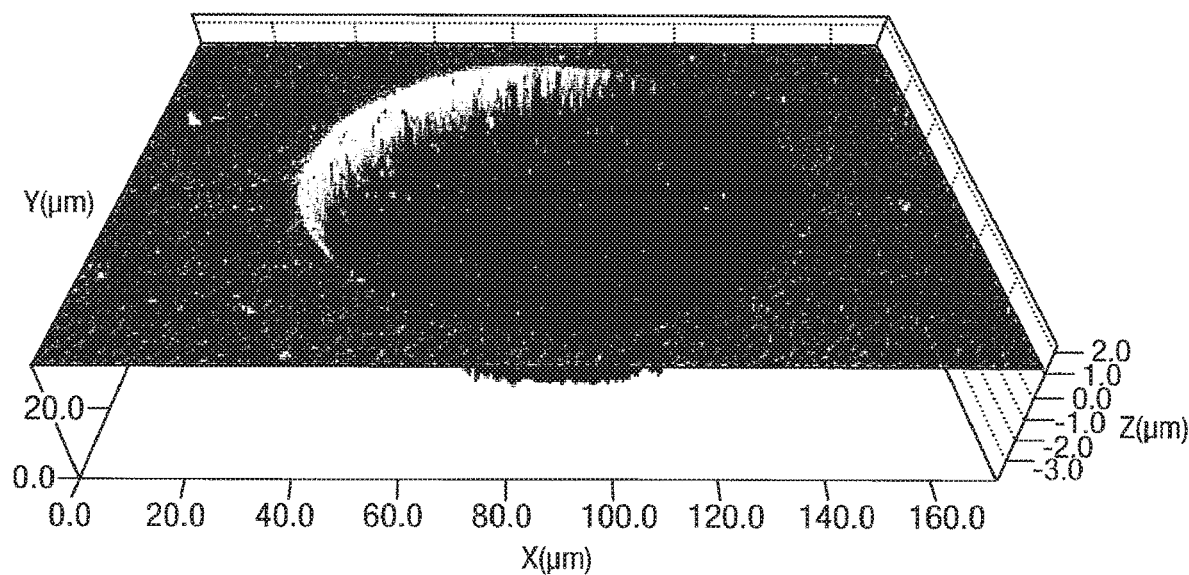
FIGS. 8A and 8B are 3D and 2D LP profiles, respectively, of a recess formed using photolithography, after electroplating.
Figure 8B:
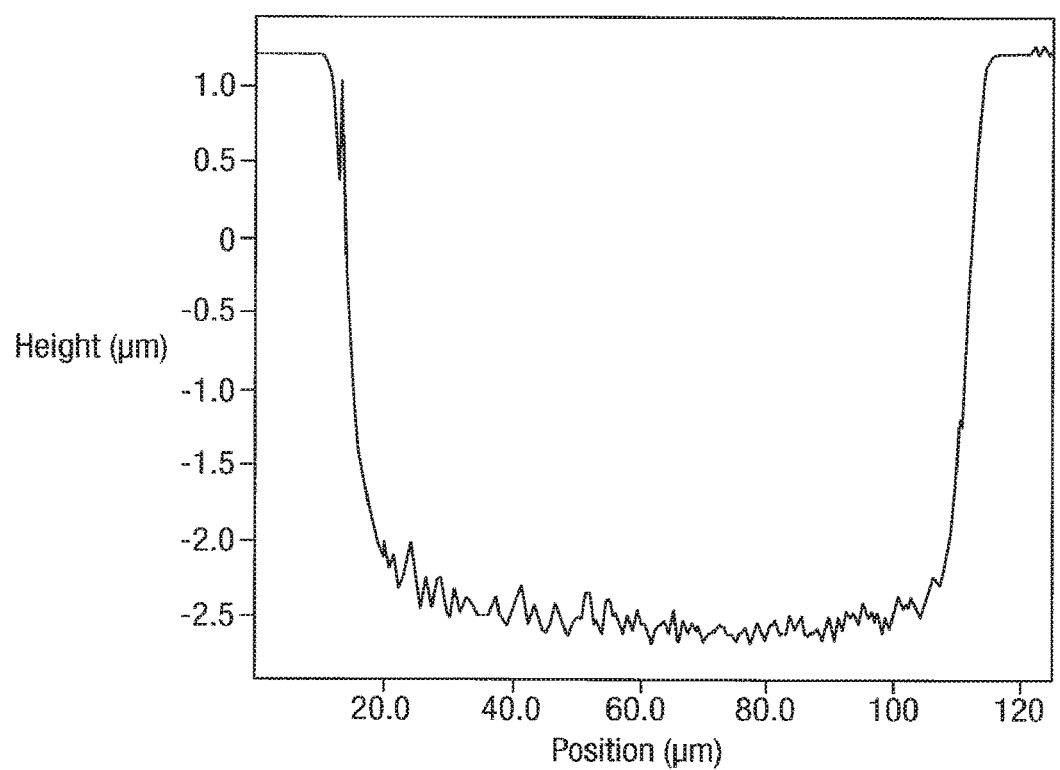

FIG. 6 shows an OM image of a recess 5 formed using photolithography of a further layer 4 of SUB photoresist over an electrode 21 of vapour deposited gold on a substrate 3 of silicon. Similarly, FIGS. 7A and 7B are 3D and 2D LP profiles of a similarly manufactured recess 5. FIGS. 8A and 8B are 3D and 2D LP profiles of the same recess 5 after electroplating to form a coating 38 of silver. These images show that photolithography provides a high degree of control of the geometry and dimensions of the recess.

Excimer laser methods also produce a controlled geometry similar to photolithography.

Figure 33:
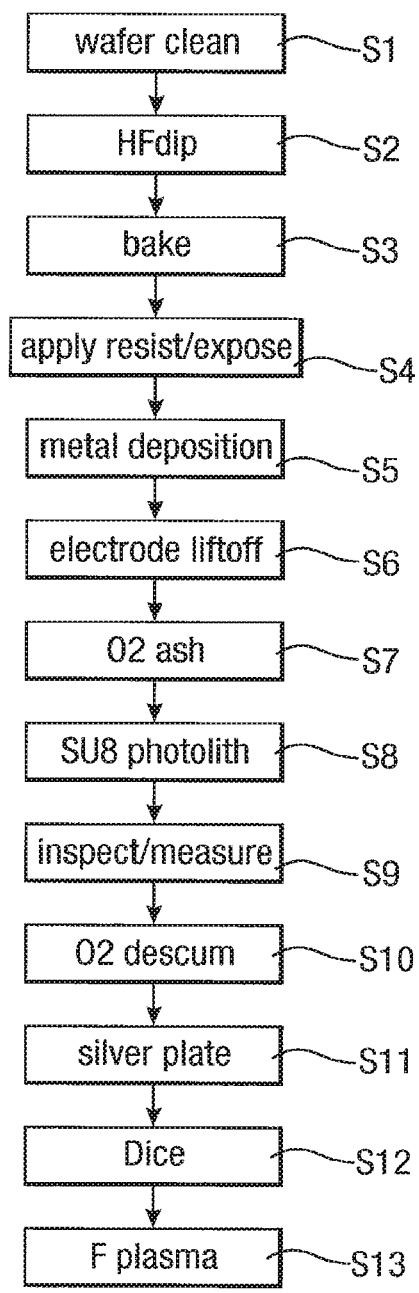
FIG. 33 is a flow chart of a method of manufacture of the apparatus.

There will now be described an example of a method of manufacture of the apparatus 1, as shown in FIG. 33. The rationale of this method is to provide high throughput manufacture. This is achieved by processing a wafer of silicon which forms the substrate 3 of plural apparatuses 1 and which is subsequently diced. The wafer is prepared with an insulating layer, for example a thermally grown silicon-oxide.

First the wafer is prepared. In step S1, the wafer is cleaned. In step S2, the wafer is subjected to a BF dif to improve adhesion of metals and resist. Typical conditions are a 3 minute dip in 10:1 buffered oxide etch. In S3, the wafer is subjected to a bake as a dehydration step. Typical conditions are baking for 1 hour at 200° C. in an oven. Next, the wafer is metallised to provide the first conductive layer 20 of each apparatus 1. In step S4, photoresist is spun onto the wafer which is then subjected to UV light to form the desired pattern. In step S5, the conductive layers 20 are deposited, for example consisting of successive layers of Cr and Au. Typically of respective thicknesses 50 nm and 300 nm. In step S6 the resist is removed for example by soaking in acetone.

Next, the layers 4 and recesses 5 are formed. In step S7, photoresist adhesion is improved by the application of an O₂ plasma and dehydration bake for example in an oven. In step S8, the wafer has applied thereto photoresist which is then subjected to UV exposure to form the layers 4 and recesses, for example SU8-10 with a thickness of 20m. In step S9 an inspection and measurement of the recesses is performed.

Next, the electrodes 21 are plated. In step S10, the surface is prepared for plating by performing an O₂ plasma descum. In step S11, silver plating of the electrode is performed, as described above, for example to form a plating thickness of 1.5 µm.

In step S12, the wafer is diced to form the bodies 2 of separate apparatuses 1.

Lastly, the bodies 2 are treated by a CF₄ plasma which modifies the surfaces of the body 2 and the electrode 21 as discussed above. A typical exposure is for 12 minutes at 70 W and 160 mTorr.

In practice with an apparatus 1 manufactured using this method, the results of bilayer formation and pore current stability have been comparable to those achieved with bodies plated and chloridised by wet chemical means.

The method of using the apparatus 1 to form a layer 11 of amphiphilic molecules will now be described. First the nature of the amphiphilic molecules that may be used will be considered.

The amphiphilic molecules are typically a lipid. In this case, the layer is a bilayer formed from two opposing monolayers of lipid. The two monolayers of lipids are arranged such that their hydrophobic tail groups face towards each other to form a hydrophobic interior. The hydrophilic head groups of the lipids face outwards towards the aqueous environment on each side of the bilayer. The bilayer may be present in a number of lipid phases including, but not limited to, the liquid disordered phase (fluid lamellar), liquid ordered phase, solid ordered phase (lamellar gel phase, interdigitated gel phase) and planar bilayer crystals (lamellar sub-gel phase, lamellar crystalline phase).

Any lipids that may form a lipid bilayer may be used. The lipids are chosen such that a lipid bilayer having the required properties, such as surface charge, ability to support membrane proteins, packing density or mechanical properties, is formed. The lipids can comprise one or more different lipids. For instance, the lipids can contain up to 100 lipids. The lipids preferably contain 1 to 10 lipids. The lipids may comprise naturally-occurring lipids and/or artificial lipids.

The lipids typically comprise a head group, an interfacial moiety and two hydrophobic tail groups which may be the same or different. Suitable head groups include, but are not limited to, neutral head groups, such as diacylglycerides (DO) and ceramides (CM); zwitterionic head groups, such as phosphatidylcholine (PC), phosphatidylethanolamine (PE) and sphingomyelin (SM); negatively charged head groups, such as phosphatidylglycerol (PG); phosphatidylserine (PS), phosphatidylinositol (PI), phosphatic acid (PA) and cardiolipin (CA); and positively charged headgroups, such as trimethylammonium-Propane (TAP). Suitable interfacial moieties include, but are not limited to, naturally-occurring interfacial moieties. such as glycerol-based or ceramide-based moieties. Suitable hydrophobic tail groups include, but are not limited to, saturated hydrocarbon chains, such as lauric acid (n-Dodecanolic acid), myristic acid (n-Tetradecononic acid), palmitic acid (n-Hexadecanoic acid), stearic acid (n-Octadecanoic) and arachidic (n-Eicosanoic); unsaturated hydrocarbon chains, such as oleic acid (cis-9-Octadecanoic); and branched hydrocarbon chains, such as phytanoyl. The length of the chain and the position and number of the double bonds in the unsaturated hydrocarbon chains can vary. The length of the chains and the position and number of the branches, such as methyl groups, in the branched hydrocarbon chains can vary. The hydrophobic tail groups can be linked to the interfacial moiety as an ether or an ester.

The lipids can also be chemically-modified. The head group or the tail group of the lipids may be chemically-modified. Suitable lipids whose head groups have been chemically-modified include, but are not limited to, PEG-modified lipids, such as 1,2-Diacyl-sn-Glycero 3-Phosphoethanolamine-N-[Methoxy(Polyethylene glycol)-2000]; functionionalised PEG Lipids, such as 1,2-Distearoyl-sn-Glycero-3 Phosphoethanolamine-N-[Biotinyl(Polyethylene Glycol)2000]; and lipids modified for conjugation, such as 1,2-Dioleoyl-sn-Glycero-3, Phosphoethanolamine-N-(succinyl) and 1,2-Dipalmitoyl-sn-Glycero-3-Phosphoethanolamine-N-(Biotinyl). Suitable lipids whose tail groups have been chemically-modified include, but are not limited to, polymerisable lipids, such as 1,2-bis(10,12-tricosadiynoyl)-sn-Glycero-3-Phosphocholine; fluorinated lipids, such as 1-Palmitoyl-2-(16-Fluoropalmitoyl)-sn-Glycero-3-Phosphocholine; deuterated lipids, such as 1,2-Dipalmitoyl-D62-sn-Glycero-3-Phosphocholine; and ether linked lipids, such as 1,2-Di-O-phytanyl-sn-Glycero-3-Phosphocholine.

The lipids typically comprise one or more additives that will affect the properties of the lipid bilayer. Suitable additives include, but are not limited to, fatty acids, such as palmitic acid, myristic acid and oleic acid; fatty alcohols, such as palmitic alcohol, myristic alcohol and oleic alcohol; sterols, such as cholesterol, ergosterol, lanosterol, sitosterol and stigmasterol; lysophospholipids, such as 1-Acyl-2-Hydroxy-sn-Glycero-3-Phosphocholine; and ceramides. The lipid preferably comprises cholesterol and/or ergosterol when membrane proteins are to be inserted into the lipid bilayer.

However, although lipids are commonly used to form bilayers, it is expected that in general the method is applicable to any amphiphilic molecules which may form a layer.

As to the aqueous solution 10, in general a wide range of aqueous solutions 10 that are compatible with the formation of a layer 11 of amphiphilic molecules may be used. The aqueous solution 10 is typically a physiologically acceptable solution. The physiologically acceptable solution is typically buffered to a pH of 3 to 11. The pH of the aqueous solution 10 will be dependent on the amphiphilic molecules used and the final application of the layer 11. Suitable buffers include without limitation: phosphate buffered saline (PBS); N-2-Hydroxyethylpiperazine-N'-2-Ethanesulfonic Acid (HEPES) buffered saline; Piperazine-1,4-Bis-2-Ethanesulfonic Acid (PIPES) buffered saline; 3-(n-Morpholino)Propanesulfonic Acid (MOPS) buffered saline; and Tris(Hydroxymethyl)aminomethane (TRIS) buffered saline. By way of example, in one implementation, the aqueous solution 10 may be 10 mM PBS containing 1.0 M sodium chloride (NaCl) and having a pH of 6.9.

The method of using the apparatus 1 is as follows.

Figure 9:
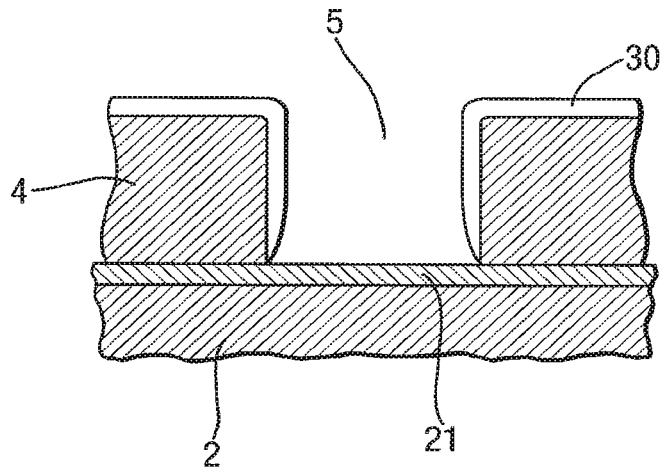
FIG. 9 is a cross-sectional, partial view of the recess in the apparatus with a pre-treatment coating applied.

First, a pre-treatment coating 30 is applied to the body 2 across the recess 5, as shown in FIG. 9. The pre-treatment coating 30 is a hydrophobic fluid which modifies the surface of the body 2 surrounding the recess 5 to increase its affinity to the amphiphilic molecules.

The pre-treatment coating 30 is typically an organic substance, usually having long chain molecules, in an organic solvent. Suitable organic substances include without limitation: n-decane, hexadecane, isoecoisane, squalene, fluorinated oils (suitable for use with fluorinated lipids), alkyl-silane (suitable for use with a glass membrane) and alkyl-thiols (suitable for use with a metallic membrane). Suitable solvents include but are not limited to: pentane, hexane, heptane, octane, decane, and toluene. The material might typically be 0.1 µl to 10 µl of 0.1% to 50% (v/v) hexadecane in pentane or another solvent, for example 2 µl of 1% (v/v) hexadecane in pentane or another solvent, in which case lipid, such as diphantytanoyl-sn-glycero-3-phosphocholine (DPhPC), might be included at a concentration of 0.6 mg/ml.

Some specific materials for the pre-treatment coating 30 are set out in Table 1 by way of example and without limitation.

TABLE 1

| Pre-treatment formulation | Volumes applied |
| --- | --- |
| 0.3% hexadecane in pentane | 2x 1 µl |
| 1% hexadecane in pentane | 2x2x 0.5 µl; 2x 0.5 µl; 1 µl; 2x 1 µl; 2x 1 µl; 2 µl; 2x 2 µl; 5 µl |
| 3% hexadecane in pentane | 2x 1 µl; 2 µl |
| 10% hexadecane in pentane | 2x 1 µl; 2 µl; 5 µl |
| 0.5% hexadecane + 0.6 mg/ml DPhPC lipid in pentane | 5 µl |
| 1.0% hexadecane + 0.6 mg/ml DPhPC lipid in pentane | 2x 2x 0.5 µl |
| 1.5% hexadecane + 0.6 mg/ml DPhPC lipid in pentane | 2 µl; 2x 1 µl |

The pre-treatment coating 30 may be applied in any suitable manner, for example simply by capillary pipette.

The pre-treatment coating 30 may be applied before or after the cover 6 is attached to the apparatus 1.

The precise volume of material of the pre-treatment coating 30 required depends on the size of the recess 5, the formulation of the material, and the amount and distribution of the when it dries around the aperture. In general increasing the amount (by volume and/or by concentration) improves the effectiveness, although excessive material can cover the electrode 21 as discussed below. As the diameter of the recess 5 is decreased, the amount of material of the pre-treatment coating 30 required also varies. The distribution of the pre-treatment coating 30 can also affect effectiveness, this being dependent on the method of deposition, and the compatibility of the membrane surface chemistry. Although the relationship between the pre-treatment coating 30 and the case and stability of layer formation is complex, it is straightforward to optimize the amount by routine trial and error. In another method the chamber 7 can be completely filled by pre-treatment in solvent followed by removal of the excess solvent and drying with a gas flow.

The pre-treatment coating 30 is applied across the recess 5. As a result and as shown in FIG. 9, the pre-treatment coating 30 covers the surface of the body 2 around the recess 5. The pre-treatment coating 30 also extends over the rim of the recess 5 and desirably covers at least the outermost portion of the side walls of the recess 5. This assists with formation of the layer 11 of amphiphilic molecules across the recess 5.

However, the pro-treatment coating 30 also has a natural tendency during application to cover the electrode 21. This is undesirable as the pro-treatment coating 30 reduces the flow of current to the electrode 21 and therefore reduces the sensitivity of measurement of electrical signals, in the worst case preventing any measurement at all. A number of different techniques may be employed to reduce or avoid this problem, and will be discussed after the description of forming the layer 11 of amphiphilic molecules.

After application of the pre-treatment coating 30, the aqueous solution 10 is flowed across the body 2 to cover the recess 5 as shown in FIG. 3. This step is performed with the amphiphilic molecules added to the aqueous solution 10. It has been demonstrated that, with an appropriate pre-treatment coating 30 this allows the formation of the layer 11 of amphiphilic molecules across the recess 5. Formation is improved if a multi-pass technique is applied in which aqueous solution 10 covers and uncovers the recess 5 at least once before covering the recess 5 for a final time. This is thought to be because at least some aqueous solution is left in the recess 5 which assists formation of the layer 11 in a subsequent pass. Notwithstanding this, it should be noted that the formation of the layer 11 is reliable and repeatable. This is despite the fact that the practical technique of flowing aqueous solution 10 across the body 2 through the chamber 7 is very easy to perform. Formation of the layer 11 may be observed by monitoring of the resultant electrical signals across the electrodes 21 and 24, as described below. Even if a layer 11 fails to form it is a simple matter to perform another pass of the aqueous solution 10. Such reliable formation of a layer 11 of amphiphilic molecules using a simple method and a relatively simple apparatus 1 is a particular advantage of the present disclosure.

Furthermore, it has been demonstrated that the layers 11 of amphiphilic molecules are of high quality, in particular being suitable for high sensitivity biosensor applications such as stochastic sensing and single channel recording. The layers 11 have high resistance providing highly resistive electrical seals, having an electrical resistance of 1 GΩ or more, typically at least 100 GΩ which, for example, enables high-fidelity stochastic recordings from single protein pores.

This is achieved whilst trapping a volume of aqueous solution 10 in the recess 5 between the layer 11 and the electrode 21. This maintains a significant supply of electrolyte. For example, the volume of aqueous solution 10 is sufficient to allow stable continuous do current measurement through membrane proteins inserted in the layer. Experimental results demonstrating these advantages are set out later.

There are various techniques for adding the amphiphilic molecules to the aqueous solution 10, as follows.

A first technique is simply to add the amphiphilic molecules to the aqueous solution 10 outside the apparatus 1 before introducing the aqueous solution 10 into the chamber 7.

A second technique which has particular advantage is, before introducing the aqueous solution 10 into the chamber 7, to deposit the amphiphilic molecules on an internal surface of the chamber 7, or on an internal surface elsewhere in the flow path of the aqueous solution 10 into the chamber 7, for example in a fluidic inlet pipe connected to the inlet. The amphiphilic molecules can be deposited on any one or more of the internal surfaces of the chamber 7, including a surface of the further layer 4 or of the cover 6. The aqueous solution 10 covers the internal surface during its introduction, whereby the amphiphilic molecules are added to the aqueous solution 10. In this manner, the aqueous solution 10 is used to collect the amphiphilic molecules from the internal surface. The aqueous solution 10 may cover the amphiphilic molecules and the recess 5 in any order but preferably covers the amphiphilic molecules first. If the amphiphilic molecules are to be covered first, the amphiphilic molecules are deposited along the flow path between the inlet 8 and the recess 5.

Any method may be used to deposit the lipids on an internal surface of the chamber 7. Suitable methods include, but are not limited to, evaporation or sublimation of a carrier solvent, spontaneous deposition of liposomes or vesicles from a solution and direct transfer of the dry lipid from another surface. An apparatus 1 having lipids deposited on an internal surface may be fabricated using methods including, but not limited to, drop coating, various printing techniques, spin-coating, painting, dip coating and aerosol application.

The deposited amphiphilic molecules are preferably dried. In this case, the aqueous solution 10 is used to rehydrate the amphiphilic molecules. This allows the amphiphilic molecules to be stably stored in the apparatus 1 before use. It also avoids the need for wet storage of amphiphilic molecules. Such dry storage of amphiphilic molecules increases shelf life of the apparatus. Even when dried to a solid state, the amphiphilic molecules will typically contain trace amounts of residual solvent. Dried lipids are preferably lipids that comprise less than 50 wt % solvent, such as less than 40 wt %, less than 30 wt %, less than 20 wt %, less than 15 wt %, less than 10 wt % or less than 5 wt % solvent.

In most practical uses, a membrane protein is inserted into the layer 11 of amphiphilic molecules. There are several techniques for achieving this.

A first technique is simply for the aqueous solution 10 to have a membrane protein added thereto, whereby the membrane protein is inserted spontaneously into the layer 11 of amphiphilic molecules after a period of time. The membrane protein may be added to the aqueous solution 10 outside the apparatus 1 before introducing the aqueous solution 10 into the chamber 7. Alternatively the membrane protein may be added after formation of the layer 11.

Another way of adding the membrane protein to the aqueous solution 10 is to deposit it on an internal surface of the chamber 7 before introducing the aqueous solution 10 into the chamber 7. In this case, the aqueous solution 10 covers the internal surface during its introduction, whereby the membrane protein is added to the aqueous solution 10 and subsequently will spontaneously insert into layer 11. The membrane proteins may be deposited on any one or more of the internal surfaces of the chamber 7, including a surface of the further layer 4 or of the cover 6. The membrane proteins can be deposited on the same or different internal surface as the amphiphilic molecules (if also deposited). The amphiphilic molecules and the membrane proteins may be mixed together.

Any method may be used to deposit the membrane proteins on an internal surface of the chamber 7. Suitable methods include, but are not limited to, drop coating, various printing techniques, spin-coating, painting, dip coating and aerosol application.

The membrane proteins arm preferably dried. In this case, the aqueous solution 10 is used to rehydrate the membrane proteins. Even when dried to a solid state, the membrane proteins will typically contain trace amounts of residual solvent. Dried membrane proteins are preferably membrane proteins that comprise less than 20 wt % solvent, such as less than 15 wt %, less than 100 wt % or less than Swt % solvem.

A second technique is for the aqueous solution 10 to have vesicles containing the membrane protein added thereto, whereby the membrane protein is inserted on fusion of the vesicles with the layer 11 of amphiphilic molecules.

A third technique is to insert the membrane protein by carrying the membrane protein to the layer 11 on a probe, for example an agar-tipped rod, using the techniques disclosed in WO-2006/100484. Use of a probe may assist in selectively inserting different membrane proteins in different layers 11, in the case that the apparatus has an array of recesses. However, this requires modification to the apparatus 1 to accommodate the probe.

Any membrane proteins that insert into a lipid bilayer may be deposited. The membrane proteins may be naturally-occurring proteins and/or artificial proteins. Suitable membrane proteins include, but are not limited to, P-barrel membrane proteins, such as toxins, porins and relatives and autotransporters; membrane channels, such as ion channels and aquaporins; bacterial rhodopsins; G-protein coupled receptors; and antibodies. Examples of non-constitutive toxins include hemolysin and leukocidin, such as Staphylococcal leukocidin. Examples of porins include anthrax protective antigen, maltoporin, OmpG, OmpA and OmpF. Examples of autotransporters include the NalP and Hia transporters. Examples of ion channels include the NMDA receptor, the potassium channel from *Streptomyces lividans* (KcsA), the bacterial mechanosensitive membrane channel of large conductance (MscL), the bacterial mechanosensitive membrane channel of small conductance (MacS) and gramicidin. Examples of G-protein coupled receptors include the metabotropic glutamate receptor. The membrane protein can also be the anthrax protective antigen.

The membrane proteins preferably comprise α-hemolysin or a variant thereof. The α-hemolysin pore is formed of seven identical subunits (heptameric). The polynucleotide sequence that encodes one subunit of α-hemolysin is shown in SEQ ID NO: 1. The full-length amino acid sequence of one subunit of α-hemolysin is shown in SEQ ID NO: 2. The first 26 amino acids of SEQ ID NO: 2 correspond to the signal peptide. The amino acid sequence of one mature subunit of α-hemolysin without the signal peptide is shown in SEQ ID NO: 3. SEQ ID NO: 3 has a methionine residue at position 1 instead of the 26 amino acid signal peptide that is present in SEQ ID NO: 2.

A variant is a heptameric pore in which one or more of the seven subunits has an amino acid sequence which varies from that of SEQ ID NO: 2 or 3 and which retains pore activity. 1, 2, 3, 4, 5, 6 or 7 of the subunits in a variant α-hemolysin may have an amino acid sequence that varies from that of SEQ ID NO: 2 or 3. The seven subunits within a variant pore are typically identical but may be different.

The variant may be a naturally-occurring variant which is expressed by an organism, for instance by a *Staphylococcus* bacterium. Variants also include non-naturally occurring variants produced by recombinant technology. Over the entire length of the amino acid sequence of SEQ ID NO: 2 or 3, a variant will preferably be at least 50% homologous to that sequence based on amino acid identity. More preferably, the subunit polypeptide is at least 80/9, at least 90%, at least 95%, at least 98%, at least 99% homologous based on amino acid identity to the amino acid sequence of SEQ ID NO: 2 or 3 over the entire sequence. Amino acid substitutions may be made to the amino acid sequence of SEQ ID NO: 2 or 3, for example a single amino acid substitution may be made or two or more substitutions may be made. Conservative substitutions may be made, for example, according to the following table. Amino acids in the same block in the second column and preferably in the same line in the third column may be substituted for each other:

| NON-AROMATIC | Non-polar | G A P |
| | | I L V |
| | Polar-uncharged | C S T M |
| | | N Q |
| | Polar-charged | D E |
| | | H K R |
| AROMATIC | | H F W Y |

Non-conservative substitutions may also be made at one or more positions within SEQ ID NO: 2 or 3, wherein the substituted residue is replaced with an amino acid of markedly different chemical characteristics and/or physical size. One example of a non-conservative substitution that may be made is the replacement of the lysine at position 34 in SEQ ID NO: 2 and position 9 in SEQ ID NO: 3 with cysteine (i.e. K34C or K9C). Another example of a non-conservative substitution that may be made is the replacement of the asparagine residue at position 43 of SEQ ID NO: 2 or position 18 of SEQ ID NO: 3 with cysteine (i.e. N43C or N17C). The inclusion of these cysteine residues in SEQ ID NO: 2 or 3 provides thiol attachment points at the relevant positions. Similar changes could be made at all other positions, and at multiple positions on the same subunit.

One or more amino acid residues of the amino acid sequence of SEQ ID NO: 2 or 3 may alternatively or additionally be deleted. Up to 50% of the residues may be deleted, either as a contiguous region or multiple smaller regions distributed throughout the length of the amino acid chain.

Variants can include subunits made of fragments of SEQ ID NO: 2 or 3. Such fragments retain their ability to insert into the lipid bilayer. Fragments may be at least 100, such as 150, 200 or 250, amino acids in length. Such fragments may be used to produce chimeric pores. A fragment preferably comprises the β-barrel domain of SEQ ID NO: 2 or 3.

Variants include chimeric proteins comprising fragments or portions of SEQ ID NO: 2 or 3. Chimeric proteins are formed from subunits each comprising fragments or portions of SEQ ID NO: 2 or 3. The f-barrel part of chimeric proteins are typically formed by the fragments or portions of SEQ ID NO: 2 or 3.

One or more amino acid residues may alternatively or additionally be inserted into, or at one or other or both ends of, the amino acid sequence SEQ ID NO: 2 or 3. Insertion of one, two or more additional amino acids to the C-terminal end of the peptide sequence is less likely to perturb the structure and/or function of the protein, and these additions could be substantial, but preferably peptide sequences of up to 10, 20, 50, 100 or 500 amino acids or more can be used. Additions at the N-terminal end of the monomer could also be substantial, with one, two or more additional residues added, but more preferably 10, 20, 50, 500 or more residues being added. Additional sequences may also be added to the protein in the trans-membrane region, between amino acid residues 119 and 139 of SEQ ID NO: 3. More precisely, additional sequences may be added between residues 127 and 130 of SEQ ID NO: 3, following removal of residues 128 and 129. Additions may be made at the equivalent positions in SEQ ED NO: 2. A carrier protein may be fused to an amino acid sequence according to the disclosure.

Standard methods in the art may be used to determine homology. For example the UWGCG Package provides the BESTFIT program which can be used to calculate homology, for example used on its default settings (Devereux et al (1984) Nucleic Acids Research 12, p387-395). The PILEUP and BLAST algorithms can be used to calculate homology or line up sequences (such as identifying equivalent residues or corresponding sequences (typically on their default settings)), for example as described in Altschul S. F. (1993) J Mol Evol 36:290,300; Altschul, S. F et al (1990) J Mol Biol 215:403-10. Software for performing BLAST analyses is publicly available through the National Center for Biotechnology Information (http://www.ncbi.ohn.nih.gov/).

The membrane proteins can be labelled with a revealing or detection/detectable label. The detectable label can be any suitable label which allows the proteins to be detected. Suitable labels include, but are not limited to, fluorescent molecules, radioisotopes, e.g. $^{125}I$, $^{35}S$, enzymes, antibodies, polynucleotides and linkers such as biotin.

The membrane proteins may be isolated from an organism, such as *Staphylococcus aureus*, or made synthetically or by recombinant means. For example, the protein may be synthesized by in vitro transcription translation. The amino acid sequence of the proteins may be modified to include non-naturally occurring amino acids or to increase the stability of the proteins. When the proteins are produced by synthetic means, such amino acids may be introduced during production. The proteins may also be modified following either synthetic or recombinant production.

The proteins may also be produced using D-amino acids. In such cases the amino acids will be linked in reverse sequence in the C to N orientation. This is conventional in the art for producing such proteins.

A number of side chain modifications are known in the art and may be made to the side chains of the membrane proteins. Such modifications include, for example, modifications of amino acids by reductive alkylation by reaction with an aldehyde followed by reduction with $NaBH_4$. amidination with methylacetimidate or acylation with acetic anhydride.

Recombinant membrane proteins may be produced using standard methods known in the art. Nucleic acid sequences encoding a protein may be isolated and replicated using standard methods in the art. Nucleic acid sequences encoding a protein may be expressed in a bacterial host cell using standard techniques in the art. The protein may be introduced into a cell by in situ expression of the polypeptide from a recombinant expression vector. The expression vector optionally carries an inducible promoter to control the expression of the polypeptide.

Thus an apparatus of the disclosure, such as apparatus 1 can be used for a wide range of applications. Typically a membrane protein is inserted in the layer 11. An electrical signal, typically a current signal, developed between the electrode 21 in the recess 5 and the further electrode 24 in the chamber 7 is monitored, using the electrical circuit 26. Often a voltage is also applied between the electrodes 21 and 24, whilst monitoring the electrical signal. The form of the electrical signal, and in particular changes therein, provide information about the layer 11 and any membrane protein inserted therein.

Some non-limitative examples of uses will now described. One use is in vitro investigation of membrane proteins by single-channel recording. An important commercial use is as a biosensor to detect the presence of a range of substances. The apparatus 1 may be used to detect an analyte molecule that binds with an inserted membrane protein, or another stimulus, using stochastic sensing by detecting a change in the current flow indicating the presence of the anlayte molecule or other stimulus.

Similarly, the apparatus 1 may be used to detect the presence or absence of membrane pores or channels in a sample, by detecting a change in the current flow as the pore or channel inserts. The lipid bilayer may be used for a range of other purposes, such as studying the properties of molecules known to be present (e.g. DNA sequencing or drug screening), or separating components for a reaction.

Some techniques to reduce or avoid the problem of the pre-treatment coating 30 covering the electrode 21 will now be discussed.

A first technique may comprise the following: after application of the pre-treatment coating 30 to apply a voltage across the electrode 21 in the recess 5 and the further electrode 24 in the chamber 7 sufficient to reduce the amount of excess hydrophobic fluid covering the electrode 21 in the recess 5. This is produces a similar effect to electro-wetting.

Figure 10A:
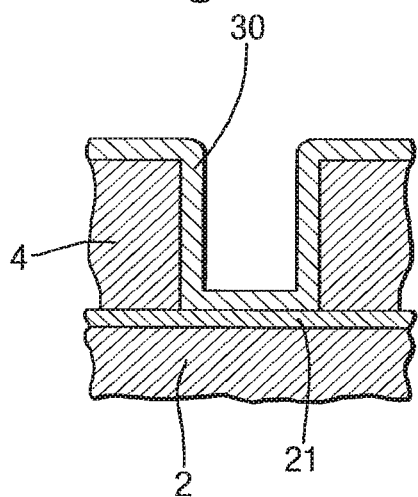
FIGS. 10A, 10B, 10C, 10D and 10E are a sequence of cross-sectional, partial view of the recess in the apparatus during a method of removing excess pre-treatment coating.
Figure 10B:
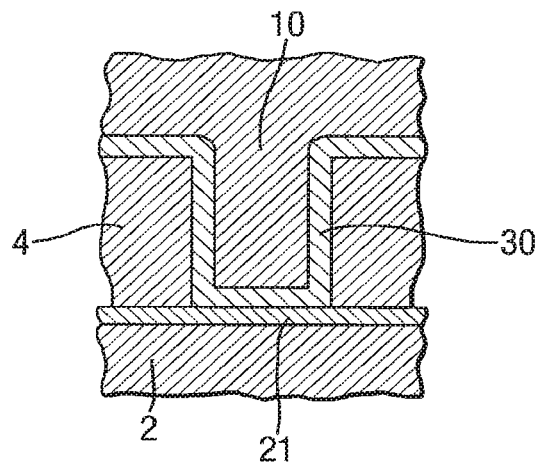
Figure 10C:
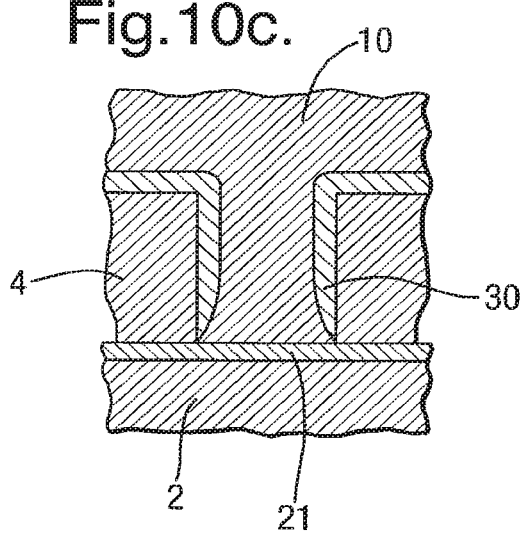
Figure 10D:
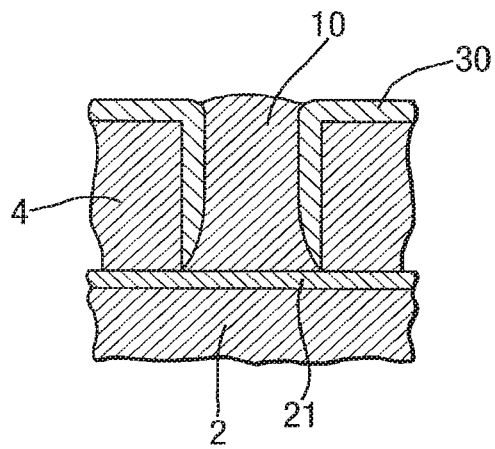
Figure 10E:
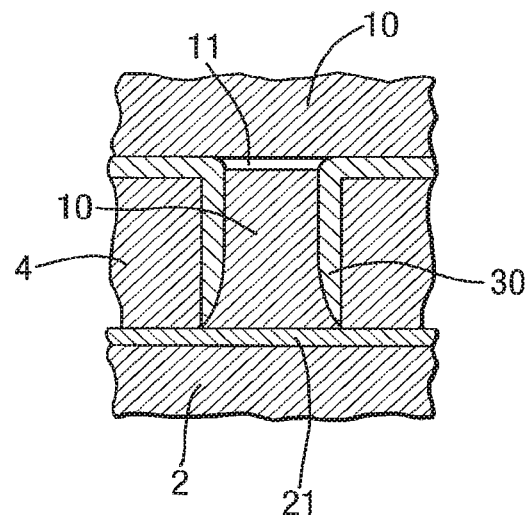

This technique is illustrated in FIGS. 10A, 10B, 10C, 10D and 10E. First, as shown in FIG. 10A, the pre-treatment coating 30 is applied as shown in FIG. 10A where the pre-treatment coating 30 covers the electrode 21. Next, as shown in FIG. 10B, aqueous solution 10 is flowed across the body 2 to cover the recess 5 so that aqueous solution 10 flows into the recess 5. Next, a voltage is applied which removes the pre-treatment coating 30 covering the electrode 21, as shown in FIG. 10C. This voltage will rupture any layer of amphiphilic molecules formed across the recess 5. Therefore, next, as shown in FIG. 10D, the aqueous solution 10 is flowed out of the chamber 7 to uncover the recess 5. Typically an amount of aqueous solution 10 will remain in the recess 5. Lastly, as shown in FIG. 10E, aqueous solution 10, having amphiphilic molecules added thereto, is flowed across the body 2 to re-cover the recess 5 so that the layer 11 of the amphiphilic molecules forms.

This is most simply performed by flowing the same aqueous solution 10 in and out of the chamber 7. However, in principle, the aqueous solution 10 flowed into the chamber 7 to re-covering the recess 5 (in FIG. 10E) could be different from the aqueous solution 10 flowed into the chamber 7 to first cover the recess 5 (in FIG. 10B) before applying the voltage. Similarly, there could be no amphiphilic molecules added to the aqueous solution 10 flowed into the chamber 7 to first cover the recess 5 (in FIG. 10B) before applying the voltage.

Figure 11:
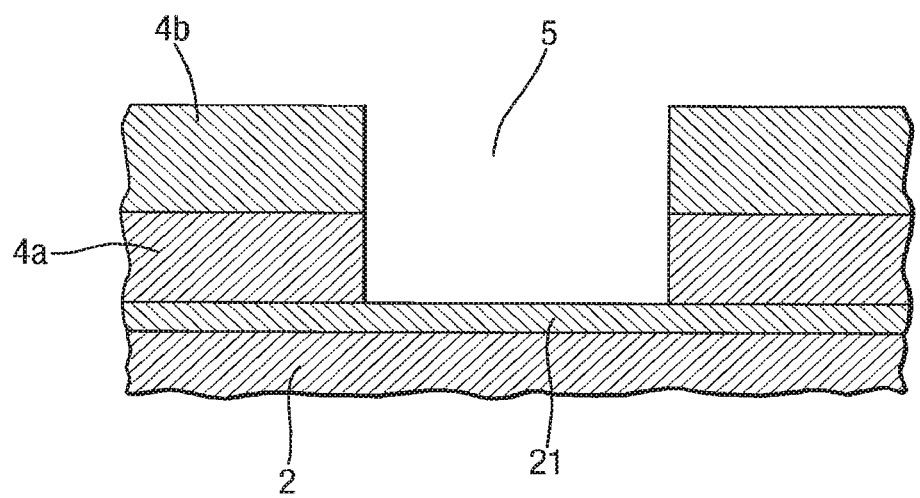
FIG. 11 is a cross-sectional, partial view of the recess in the apparatus having plural further layers in the body.

A second technique comprises making an inner part of the internal surface of recess 5 hydrophilic. This may be achieved by making body 2 with two (or in general more) further layers 4a and 4b as shown in FIG. 11, of which the innermost further layer 4a (or layers) formed of a hydrophilic material, for example $SiO_2$. Typically but without limitation, the innermost further layer 4a might have a thickness of 2 µm.

The outermost further layer 4b (or layers) is formed of a hydrophobic material and as a result both of (a) the outermost surface of the body 2 around the recess and (b) the outer part of the internal surface of the recess 5 extending from the rim of the recess 5 is hydrophobic. This assists in the spreading of the pre-treatment coating. In some embodiments, indeed this property of these surfaces of the body 2 is desirable even if there is not an inner further layer 4a formed of a hydrophilic material. Typically but without limitation, outermost further layer 4b might have a thickness of 1 µm, 3 µm, 5 µm, 10 µm, 20 µm or 30 µm.

A third technique comprises providing a hydrophillic surface on electrode 21 which repels an applied pre-treatment coating 30, whilst allowing ionic conduction from aqueous solution 10 to electrode 2. This may be achieved by depositing a protective material on electrode 21. A range of protective materials may be used. One possibility is a conductive polymer, for example polypyrrole/polystyrene sulfonate as discussed above. Another possibility is a covalently attached hydrophilic species, such as thiol-PEG.

As will be understood by those skilled in the art who have the benefit of the instant disclosure, other equivalent or alternative devices, methods, and systems for formation of layers of amphiphilic molecules can be envisioned without departing from the description contained herein. Accordingly, the manner of carrying out the disclosure as shown and described is to be construed as illustrative only. Persons skilled in the art may make various changes in the shape, size, number, and/or arrangement of parts of one or more of the apparatus of the disclosure without departing from the scope of the instant disclosure. Similarly one or more methods of the disclosure may be changed by varying the steps without departing from the scope of the disclosure. Also, where ranges have been provided, the disclosed endpoints may be treated as exact and/or approximations as desired or demanded by the particular embodiment. In addition, it may be desirable in some embodiments to mix and match range endpoints. A device or parts thereof may be configured and arranged to be disposable, serviceable, interchangeable, and/or replaceable. These equivalents and alternatives along with obvious changes and modifications are intended to be included within the scope of the present disclosure. Accordingly, the foregoing disclosure is intended to be illustrative, but not limiting, of the scope of the disclosure as illustrated by the following examples and claims.

EXAMPLE 1

The apparatus 1 described above has been made and used experimentally to demonstrate formation of a layer 11, in particular being a lipid bilayer, and insertion of a membrane protein, for example α-hemolysin. The following procedure was followed after manufacture of the apparatus 1:
1) apply pre-treatment coating 30 to body 2;
2) introduce aqueous solution 10 into chamber 7 to cover recess 5;
3) electro-wet the electrode 21;
4) remove aqueous solution 10 to un-cover recess 5 and re introduce aqueous solution 10 into chamber 7 to cover recess 5 and form the layer 11;
5) add α-hemolysin free into aqueous solution 10 and monitor insertion into layer 11.

In step 1), the pre-treatment coating 30 was hexadecane dissolved in pentane. The quantity and volume of the pre-treatment coating 30 was varied for each test to obtain the optimum conditions for formation of the layer 11. Insufficient pre-treatment coating 30 prevented formation of the layer 11 while excess pre-treatment coating 30 caused blocking of the recesses. However routine variation of the amount allowed optimisation.

The amphiphilic molecules were a lipid, in particular 1,2-diphytanoyl-sn-glycero-3-phosphocholine. The lipid was dissolved in pentane and then dried onto the surface of the cover 6 defining an internal surface of the chamber 7 before attaching the cover 6 on top of the body 2. In step 2), the aqueous solution 10 collected the lipid.

Step 3) was performed by application of a large potential to across the electrodes 21 and 24. This removed excess pre-treatment coating 30 from the electrode 21. Although not required in every case, when performed this stage helped to condition the recess 5 for formation of the layer 11 and assisted subsequent measurement of electrical signals.

By monitoring of the electrical signals developed across the electrodes 21 and 24, in steps 4) and 5), formation of the layer 11 and insertion of the membrane protein was observed.

The procedure was successfully performed for an apparatus 1 of the type described above formed by lamination onto a polymer substrate 3. Formation of the layer 11 and insertion of the membrane protein was observed using all the fabrication variables described above, albeit with varying degrees of repeatability and signal quality.

EXAMPLE 2

An example will now be described for a typical apparatus 1, in which the first conductive layer 20 was formed by a silver foil strips (25 µm thick, from Goodfellow) thermally laminated onto the substrate 3 using a 15 µm thick laminating film (Magicard) to form the further layer 4. A circular recess 5 of diameter 100 µm was created further layer 4 using an excimer laser, exposing a circular silver electrode 21 of diameter 100 µm. The exposed silver was chloridised electrochemically as described previously. The second conductive layer 23 was a screen printing silver/silver chloride ink printed on the top side of the body 2.

The pre-treatment coating 30, comprising 0.5 µl of 1% heaxadecane+0.6 mg/ml DPhPC in pentane, was then applied to the body 2 and dried at room temperature.

The cover 6 comprised a 1 mm thick silicon rubber body with a 250 µm thick Mylar lid. Lipid (4 µl of 10 mg/ml DPhPC in pentane) was applied to the inside of the cover 6 and allowed to dry at room temperature before attachment to the body 2 with self-adhesive.

A typical successful test proceeded as follows.

Figure 15:
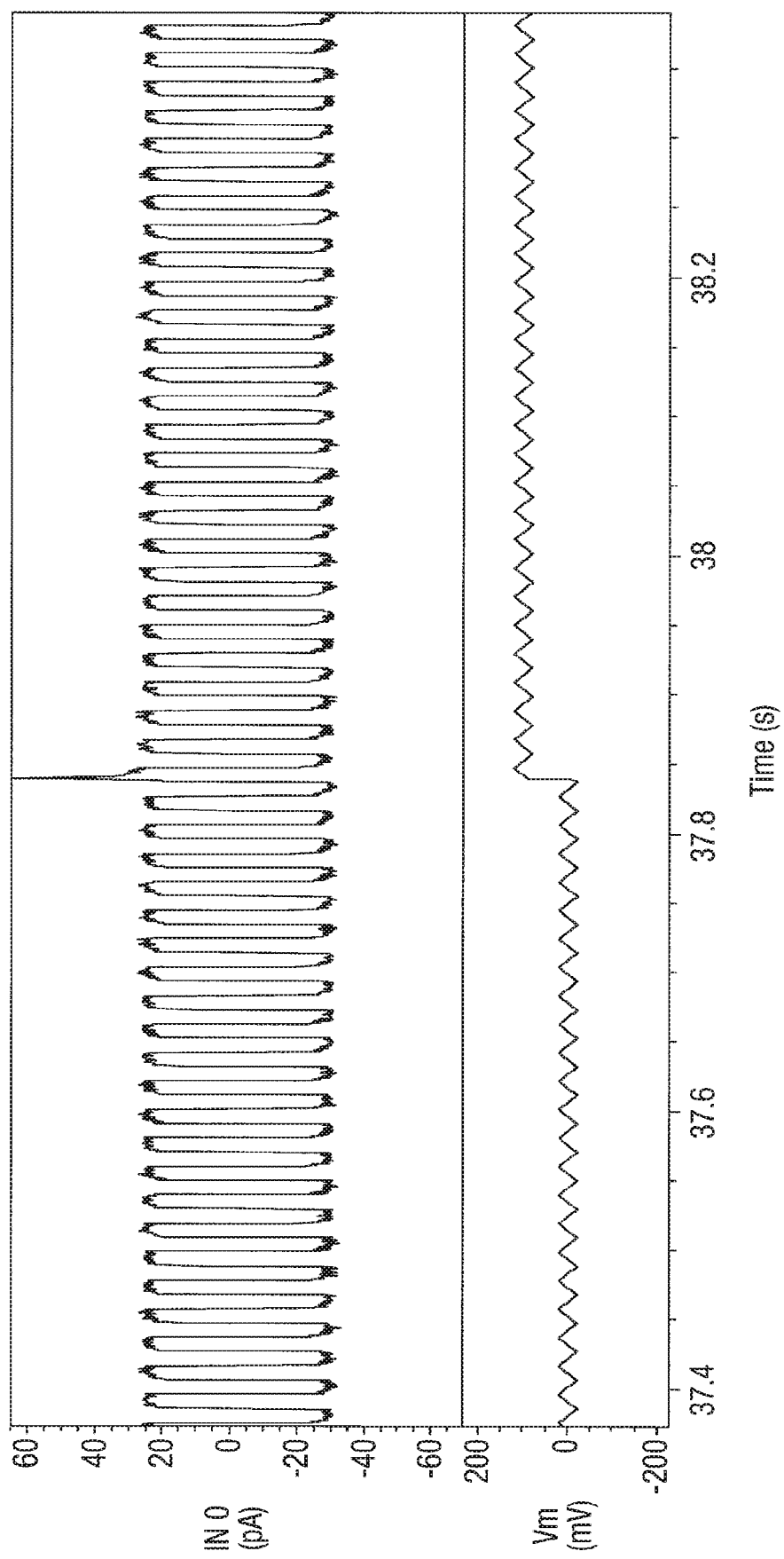
FIG. 15 is a graph of the applied potential and current response for a dry apparatus.

The dry contacts 22 and 25 were attached to the electrical circuit 26 enclosed in a Faraday cage and a 20 mV 50 Hz triangular potential waveform applied. FIG. 15 shows the applied waveform and the resultant current signal which is indicative of the expected capacitive response.

Figure 16:
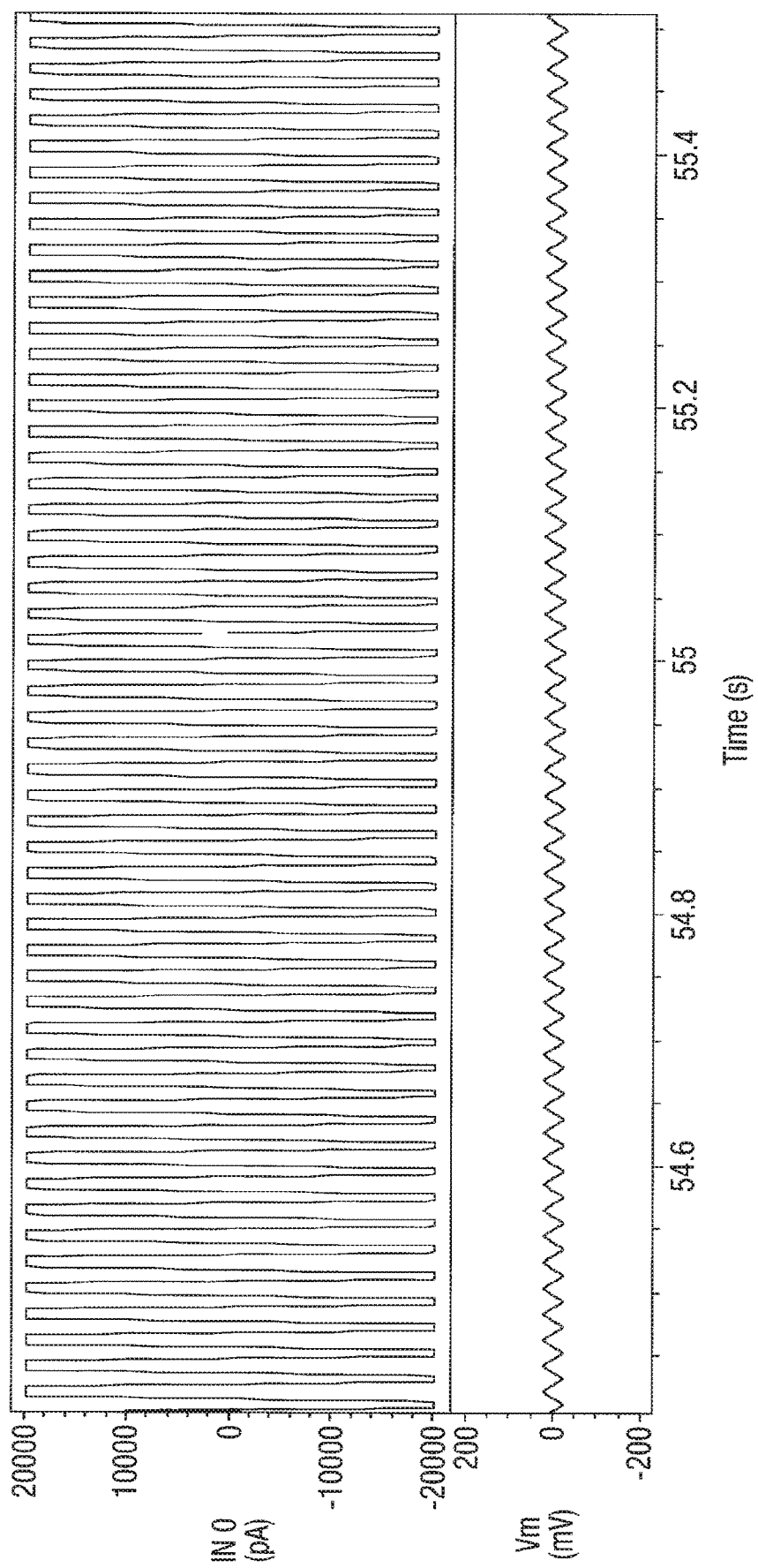
FIG. 16 is a graph of the applied potential and current response for a wet apparatus.

Addition of the aqueous solution 10 creates an "open circuit" connection between the electrodes, such that the current response to the applied potential waveform is large, typically saturating the current amplifier. A typical trace is shown in FIG. 16, involving a current response greater than 20,000 pA to the 20 mV potential. This corresponds to a resistance of less than 1MΩ, which is sufficiently small for use in conjunction with bilayer formation and pore current measurement.

Figure 17:
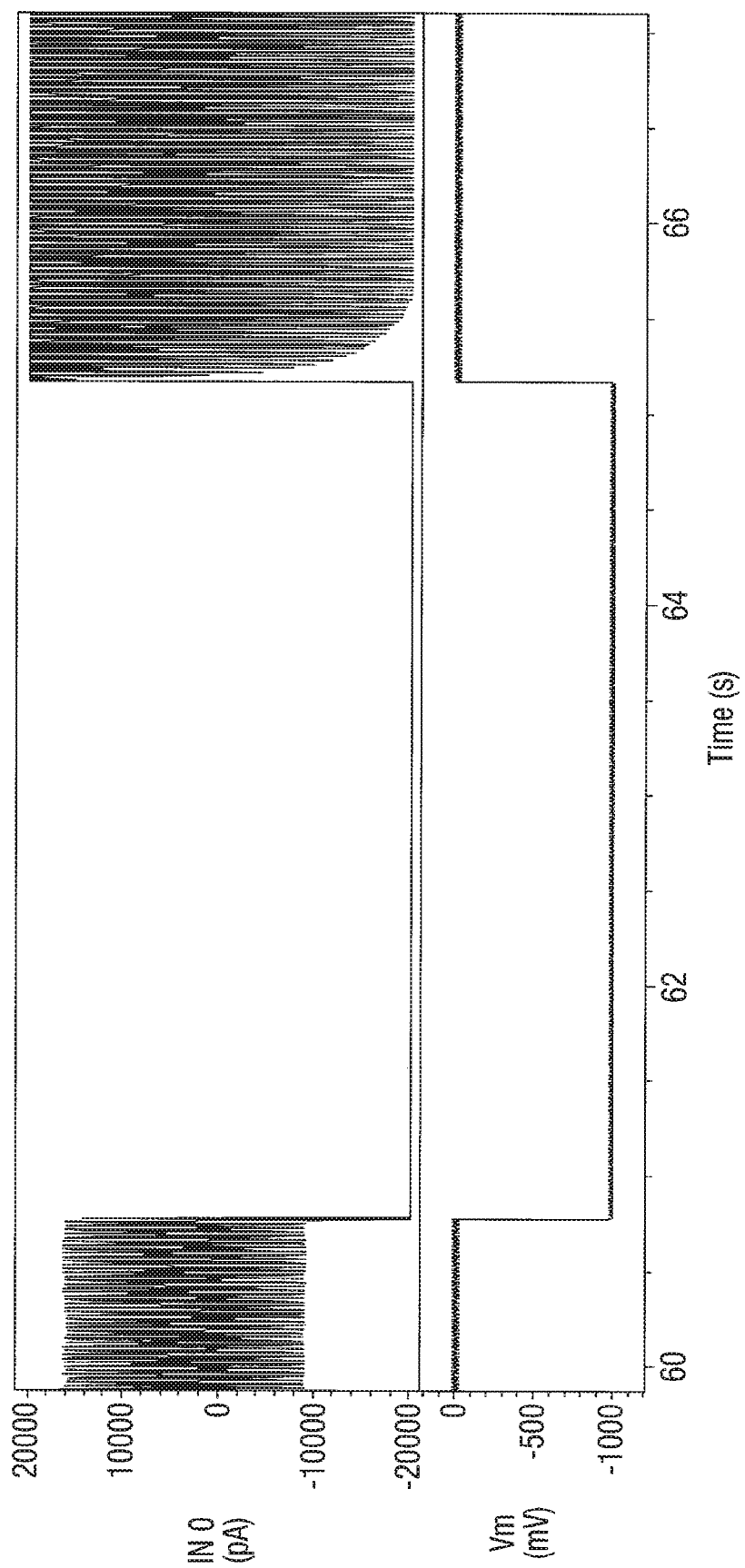
FIG. 17 is a graph of the applied potential and current response on electro-wetting of the apparatus.
Figure 18:
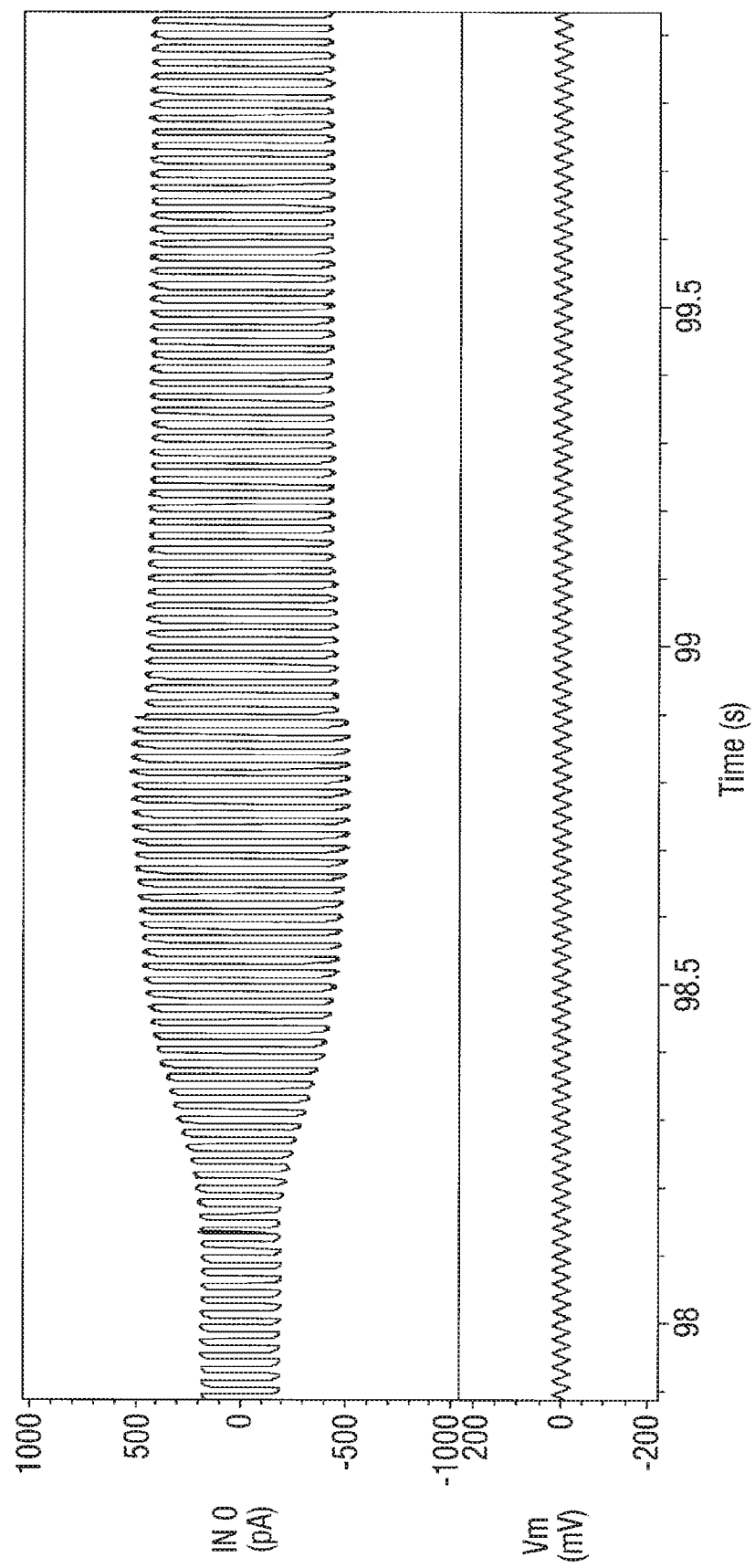
FIG. 18 is a graph of the applied potential and current response on formation of a layer of amphiphilic molecules.

In the event that the electrode 21 does not initially form a proper electrical connection with the aqueous solution 10, application of a −1 V DC potential can be used to increase in the available active electrode area. This is illustrated in FIG. 17, in which the electrode begins partially active and is then fully activated after around 4s of the applied potential.

Following open-circuit connection between the aqueous solution 10 and the electrode 21, the aqueous solution 10 is removed from the chamber 7 and reintroduced.

On re-introduction, a layer 11 of the lipid collected from the internal surface of chamber 7 is formed across recess 5. The formation is observed by an increase in the capacitive squarewave current response to just under 500 pA, for example as shown in FIG. 1g. This value is consistent with the capacitance expected for a circular lipid bilayer of diameter of order 100 μm and varies predictably for different geometries.

Figure 19:
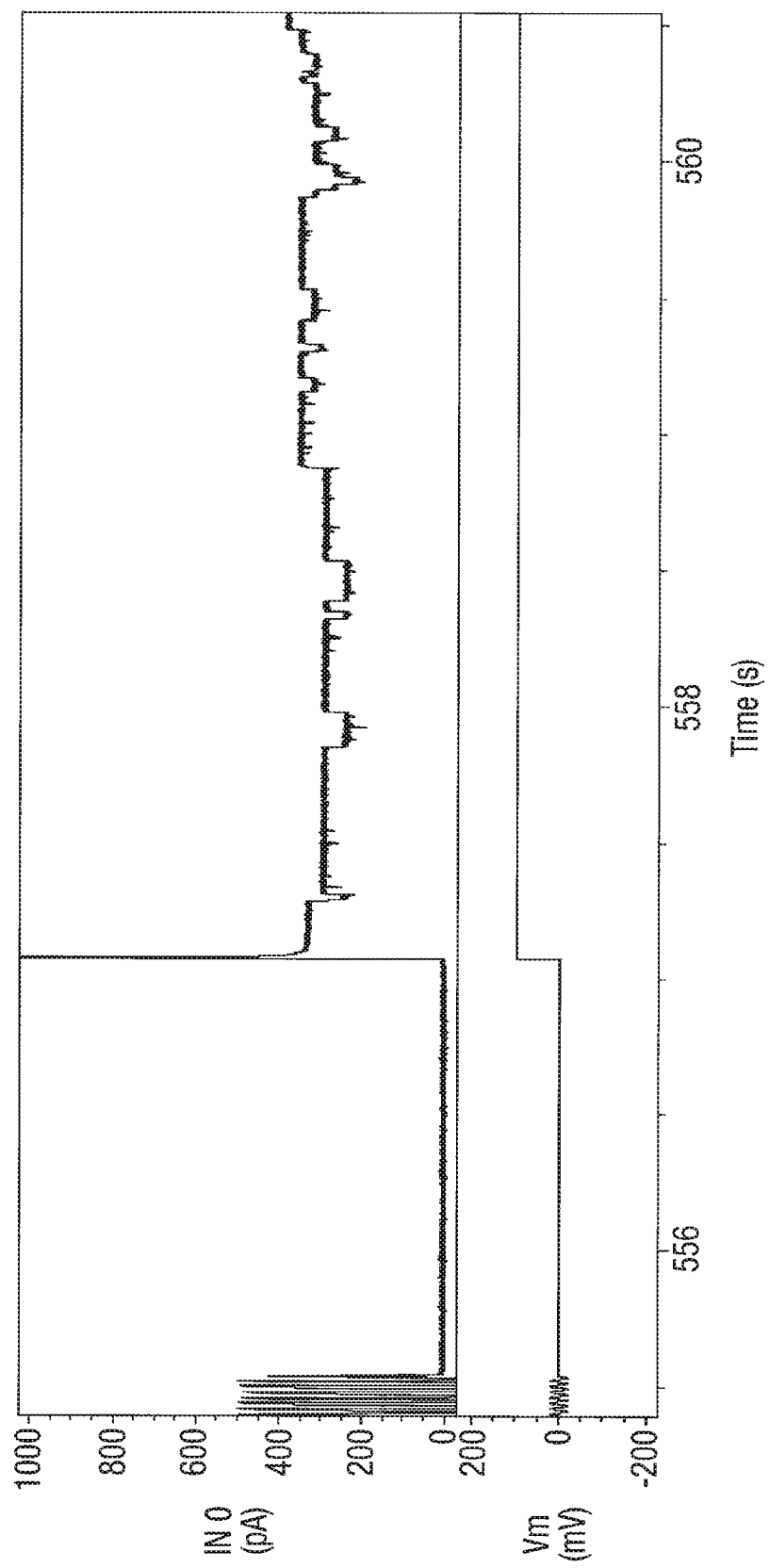
FIGS. 19, 20, 21 and 22 are graphs of the applied potential and current response for various different apparatuses.

Subsequent addition of α-hemolysin to the aqueous solution 10 creates a current response typical of pore insertion under an applied potential of 100 mV. For example FIG. 19 is a typical example with cyclodextrin present in the aqueous solution 10 and shows an expected current response with binding events confirming that the current is through the pores.

Although the example above shows data for the thermally laminated apparatus 1, the other systems investigated also produced successful formation of the layer 11 and pore insertion. For example, this was also successfully demonstrated for an apparatus 1 formed by lamination using pressure-sensitive adhesive bonding of the further layer 4. However, the adhesive layer was found to complicate formation of the recess 5 both in terms of the resulting aspect ratio and spreading of the adhesive across the electrode 21. This problem was overcome by electrical sparking to "activate" the electrode 21.

Figure 20:
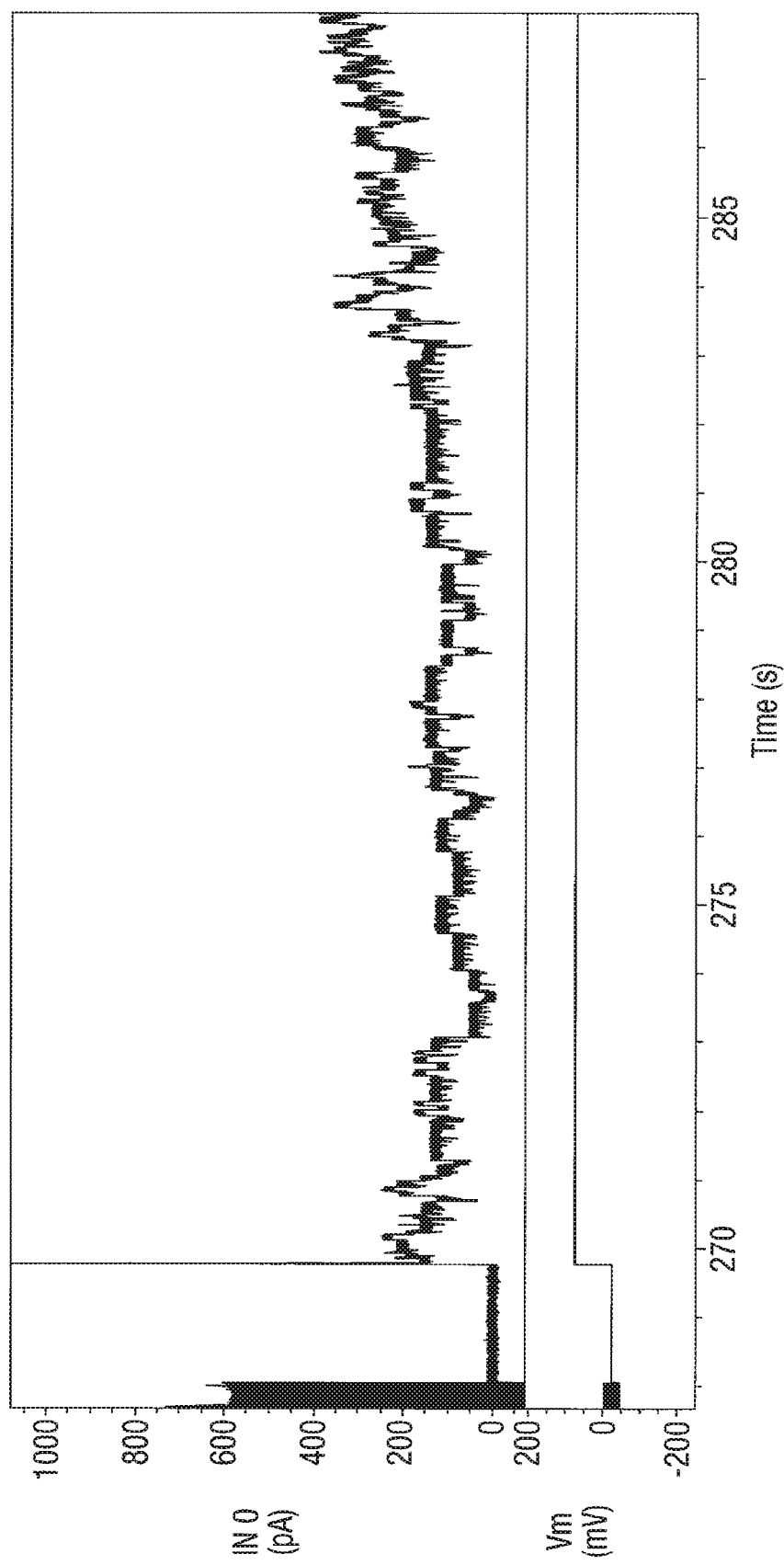
Figure 21:
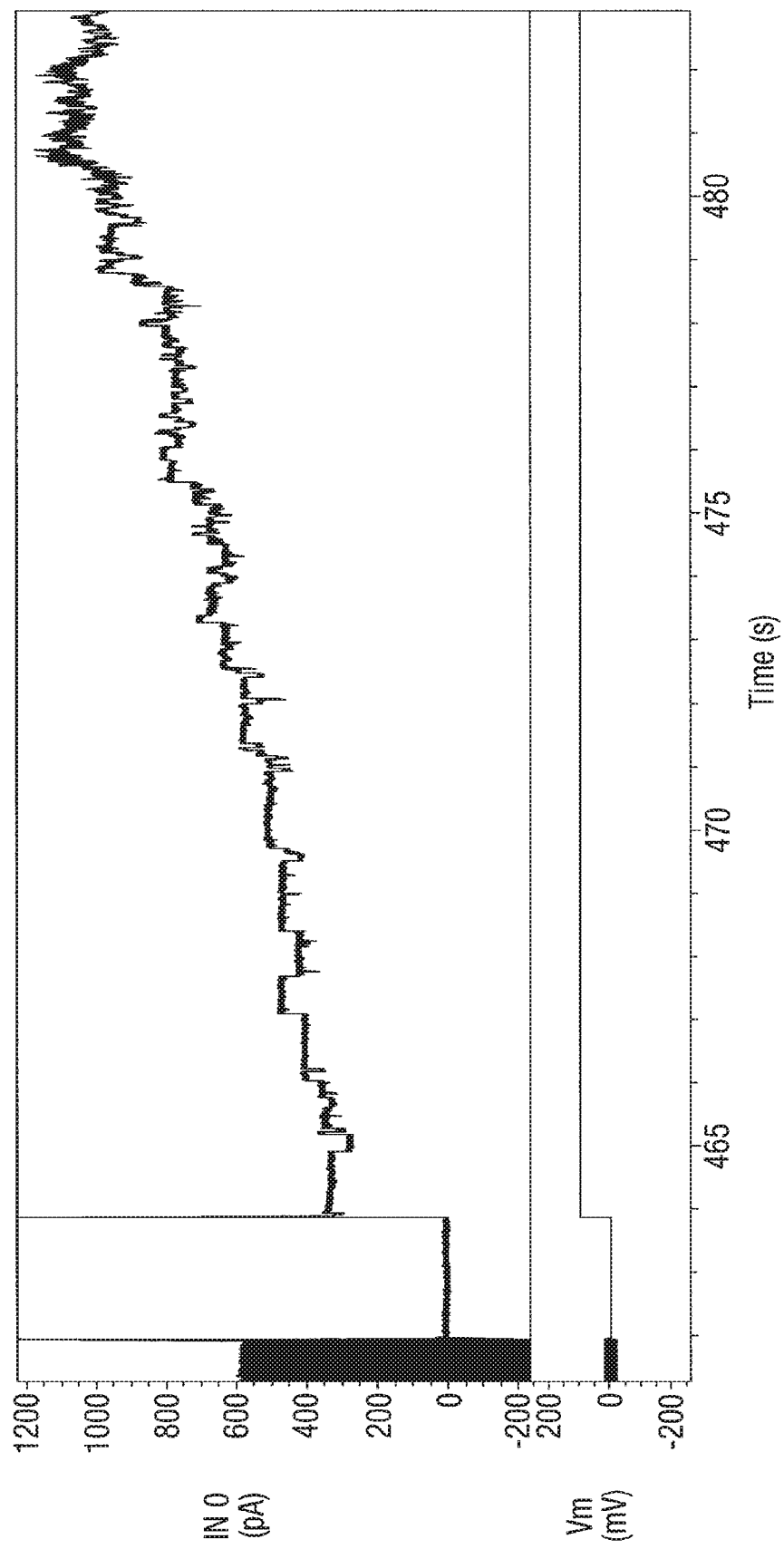

The impact of the quality of the recess 5 is evident by comparing results from recesses formed by a $CO_2$ laser and an excimer laser, as shown in FIGS. 20 and 21, respectively. In both cases formation of the layer 11 and pore insertion is successful and evident in the response, but more reproducible apertures were produced using the excimer laser. Recesses 5 formed by the $CO_2$ laser tended to form relatively leaky layers 11 with more noisy pore signals and were also susceptible to blocking. Recesses 5 formed by the excimer laser produced well sealed layers 11 with good pore signals.

Formation of the layer 11 and pore insertion was similarly observed with an apparatus 1 formed as described above using high definition printed circuit board manufacture. In this case, to form apparatus 1, the first conductive layer 20 was formed by etching the copper foil on an FR4 substrate typically used in printed circuit board manufacture. The board was then screen printed with a Ronascreen SPSR™ photoimageable solder mask to a depth of 25 μm and exposed to UV light on an Orbotech Paragon 9000 laser direct imaging machine and developed with $KaCO_3$ solution to create 100 μm circular apertures over the electrodes 21.

Formation of the layer 11 and pore insertion was similarly observed with an apparatus 1 formed as described above using photolithography. In this case, to form the apparatus 1, the first conductive layer 20 was formed by gold vapour deposited using clean-room facilities onto the substrate 3 and a further layer 4 of SU8 photoresist of thickness 12.5 μm was spin-coated on top. Recesses 5 were formed by curing of the photoresist by UV exposure with a mask and subsequent removal of the uncured photoresist. Recesses 5 had a diameter of 100 μm, exposing an electrode 21 of diameter 100 μm. After baking to set the photoresist, the wafer was diced to form separate substrates each with a single recess 5. The electrodes 21 were electroplated with silver and then chloridised electrochemically as described previously. The second electrode 24 was screen printed silver/silver chloride ink printed on the top side of the body 2.

The pre-treatment coating 30, comprising 0.5 μl of 0.75% hexadecane in pentane, was then applied to the body 2 and dried at room temperature.

The cover 6 comprised a 1 mm thick silicon rubber body with a 250 μm thick Mylar lid. Lipid (4 μl of 10 mg/ml DPhPC in pentane) was applied to the inside of the cover 6 and allowed to dry at room temperature before attachment to the body 2 with self-adhesive.

Figure 22:
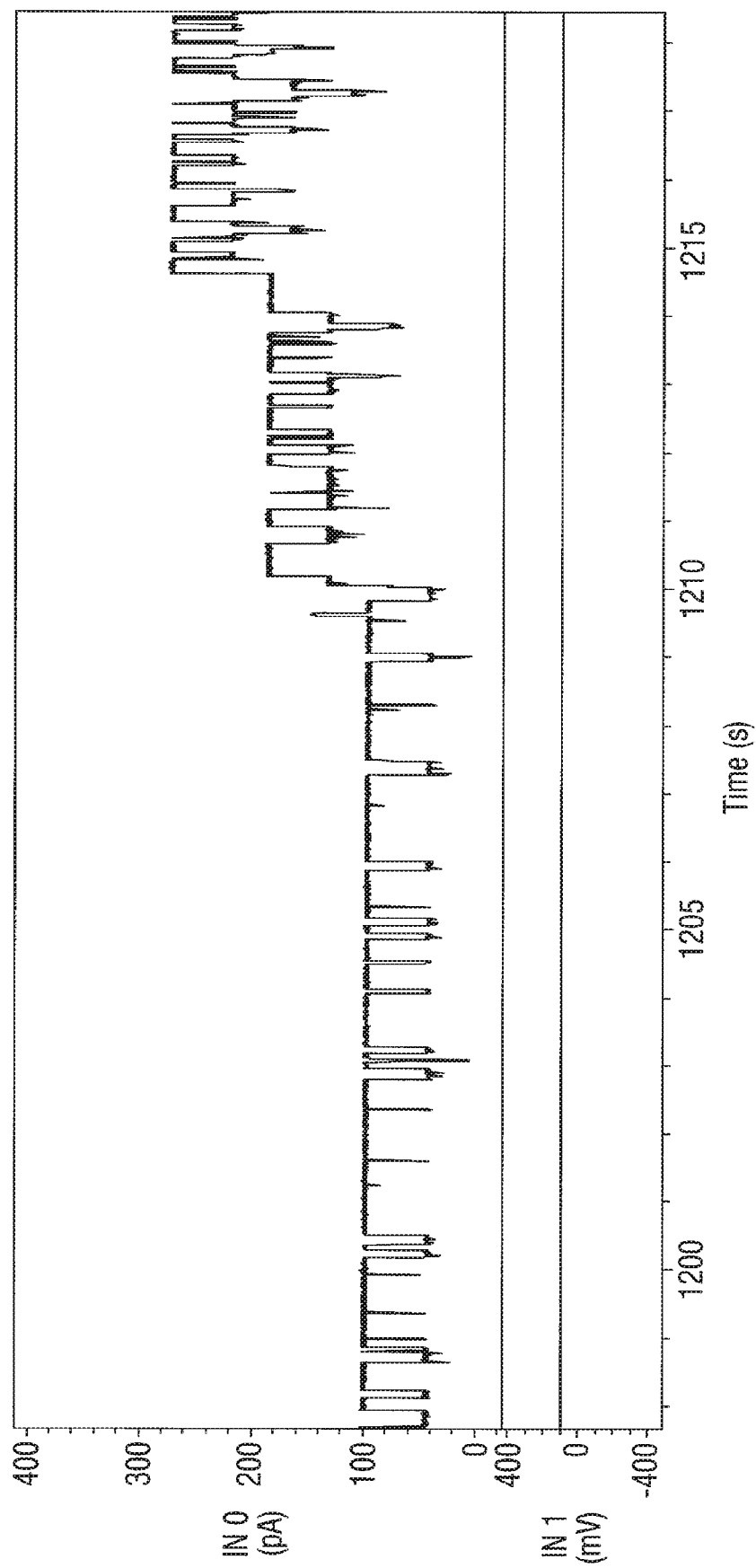

Testing was performed as described above and successful formation of the layer 11 and pore insertion was observed. For example, FIG. 22 shows a typical current trace showing cyclodextrin binding events with wild-type α-hemolysin pores.

These results generally show the ease with which the method of formation of the layer 11 may be performed. In particular formation of the layer 11 is achieved with a wide range of materials of the apparatus 1, dimensions (width and depth) of the recess 5, and methods of manufacture. Some variation in success rate is evident but in general this can be optimised by routine testing of different apparatuses 1. In particular the formation of the layer 11 is not overly dependent on the width of the recess 5. Formation has been demonstrated over widths from 5 μm to 100 μm and in view of the ease of formation it is expected that formation is possible at higher widths up to 200 μm, 500 μm or higher. Also in view of this case of formation of the layer 11, it is expected that variations of the shape of the recess 5 could also be accommodated.

EXAMPLE 3

There will now be discussed modifications to the apparatus 1 to include plural recesses 5, commonly referred to as an array of recesses 5. The ability to easily form an array of layers 11 across an array of recesses 5 in a single apparatus 1 is a particular advantage of the present disclosure. By contrast to traditional methods of formation of lipid bilayers, the apparatus 1 has a single chamber 7, but creates the layer 11 in situ during the test and captures a reservoir of electrolyte in the recess 5 under the layer 11 which allows continuous stable measurement of current passing through protein pores inserted in the layer 11. Further the layer 11 formed is of high quality and is localised to the area of the recess 5. ideal for high-fidelity current measurements using membrane protein pores. These advantages are magnified in an apparatus 1 which forms an array of layers 11 because this allows measurements to be taken across all the layers 11 in parallel, either combining the current signals to increase sensitivity or monitoring the current signals separately to perform independent measurements across each layer 11.

Apparatuses having an array of recesses 5 have been tested and demonstrated successful formation of an array of layers 11, showing the possibility of creating a miniaturized array of close packed individually addressable layers recording current signals in parallel from a test sample.

Essentially an apparatus 1 having an array of recesses 5 can be formed simply using the manufacturing techniques described above but instead forming plural recesses 5. In this case, the first conductive layer 20 is divided to form a separate electrode 21, contact 22 and intermediate conductive track 27 in respect of each recess 5. The apparatus 1 has a single chamber 7 with a single electrode 24 common to all the recesses 5.

Figure 23:
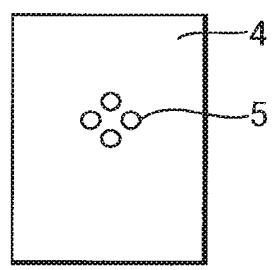
FIGS. 23, 24 and 25 are plan views of a further layer in a modified apparatus having plural recesses.
Figure 24:
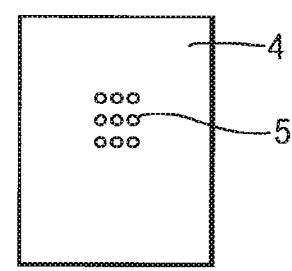
Figure 25:
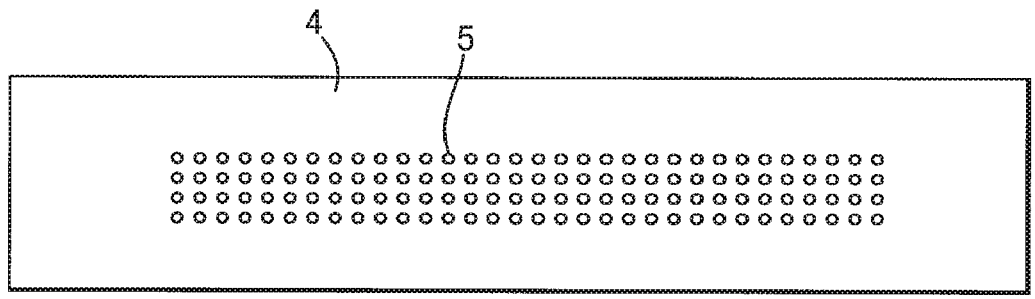

FIGS. 23, 24 and 25 show first to third designs in which the apparatus 1 is modified by providing, respectively, four, nine and 128 recesses 5 in the further layer 4.

Figure 26:
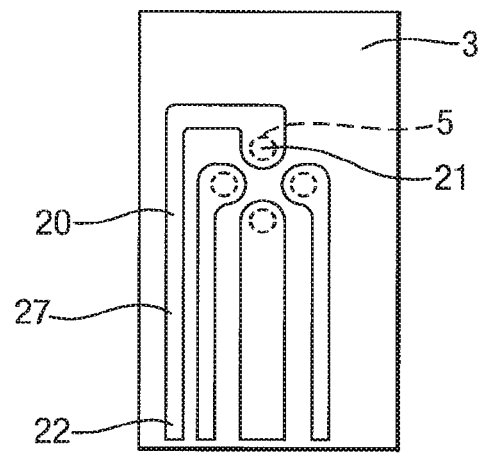
FIGS. 26, 27 and 28 are plan views of the substrate in the modified apparatuses having plural recesses.
Figure 27:
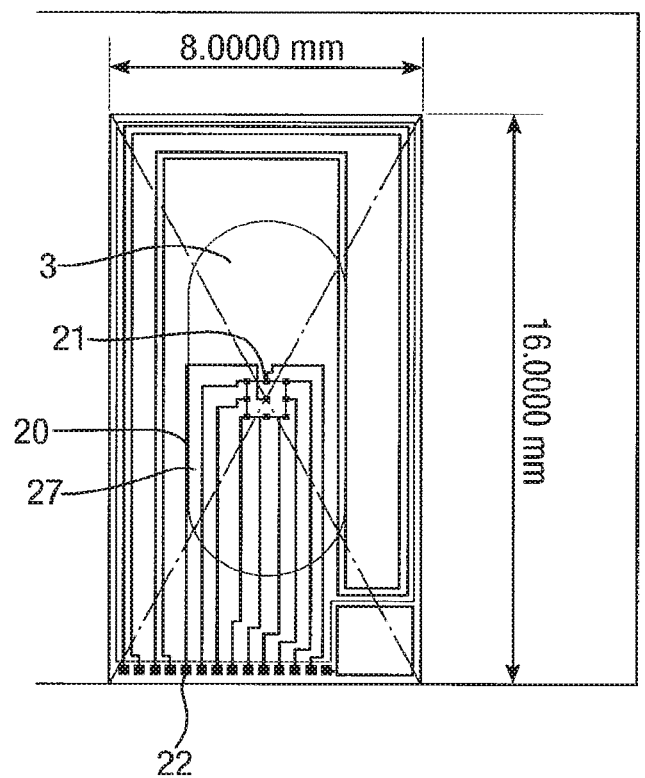
Figure 28:
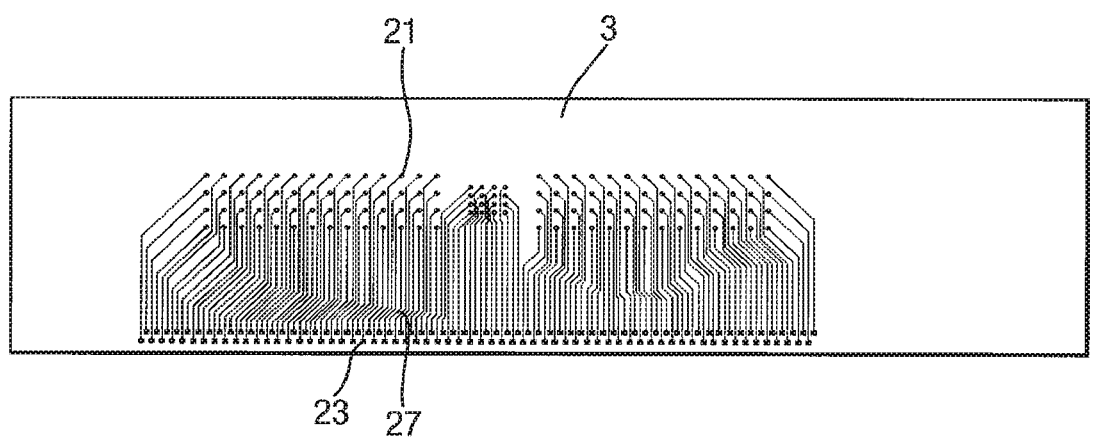

In each of the first to third designs, the first conductive layer 20 is divided, as shown, respectively, in FIGS. 26, 27 and 28 being plan views of the substrate 3. The first conductive layer 20 provides, in respect of each recess 5: an electrode 21 underneath the recess 5; a contact 22 exposed for connection of the external circuit 26 and a track 27 between the electrode 21 and the contact 22. Thus each electrode 21, and its associated track 27 and contact 22, is electrically insulated from each other allowing separate measurement of current signals from each recess 5.

Manufacture of the apparatus 1 may be performed using the techniques described above using lamination of polymer films or photolithography using silicon wafers.

Apparatuses 1 having plural recesses 5 have been made and used experimentally to demonstrate formation of a layer 11, in particular being a lipid bilayer, and insertion of a membrane protein, in particular α-hemolysin. The experimental procedure was as described above for an apparatus 1 having a single recess 5, except that formation of the layer 5 and membrane protein insertion was observed at plural recesses 5. Some examples are as follows.

An apparatus of the first design having four recesses 5 was manufactured by the technique described above of lamination onto a polymer substrate 3. The first conductive layer 20 was silver vapour deposited on a polyester sheet substrate 3. The further layer 4 was a 15 μm thick laminating film thermally laminated on top. The four recesses 5 of 100 μm diameter were formed at a pitch of 300 μm by an excimer laser.

For recording of from each recess 5 simultaneously in parallel, multiple Axon current amplifier devices were operated in parallel with a single silver/silver chloride electrode 24 in the chamber 7 as the ground electrode common to all channels.

Figure 29:
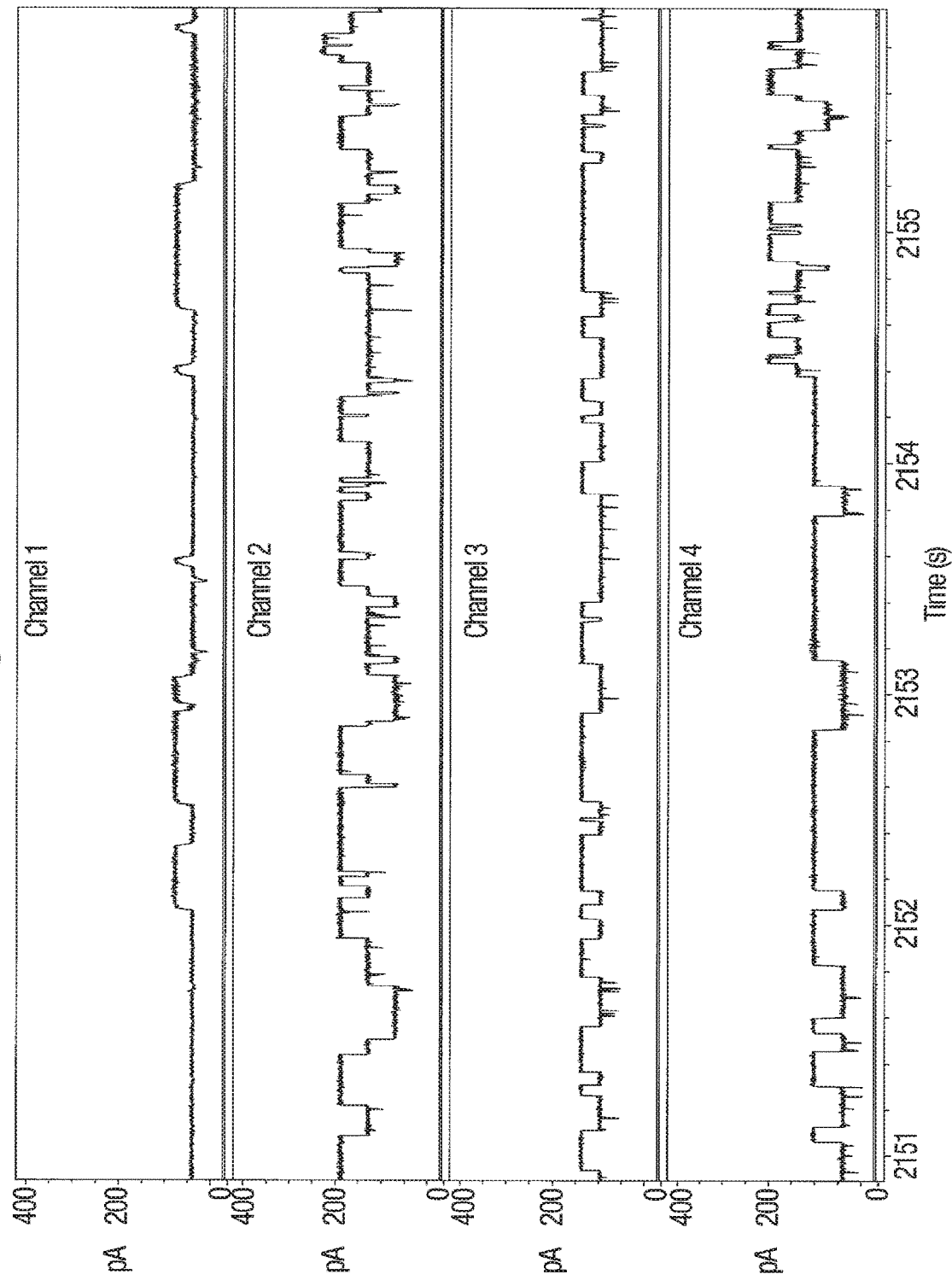
FIGS. 29 and 30 are graphs of the current response for two different apparatuses having plural recesses.

Formation of layers 11 and insertion of membrane proteins at plural recesses 5 was successfully recorded in parallel. Often this occurred at each recess 5 although sometimes a layer 11 failed to form at one or more recesses 5. For example typical current traces are shown in FIG. 29 demonstrating simultaneous formation of four layers 11, each having one or two α-hemolysin pores inserted, with cyclodextrin binding events. Notably there is no cross-talk between the signals. This confirms that the layers 11 are operating independently and can produce meaningful measurements in parallel while being individually addressed and using a common second electrode 24.

An apparatus of the second design having nine recesses 5 was manufactured by the technique described above of photolithography using silicon wafer substrates 2. The further layer 4 was 5 μm thick SUS photoresist. The nine circular recesses 5 were formed at a pitch of 300 μm by photolithography. In this case, the recesses 9 had different diameters, in particular of 5 μm, 10 μm, 15 μm, 20 μm, 20 μm, 30 μm, 40 μm, 50 μm, and 100 μm. The substrate 3 was bonded to a printed circuit board with separate tracks connected to each contact 22 and 25. Epoxy was added across the contacts 22 and 25 for protection.

In order to control the applied potential and record the current response in parallel, a multichannel electrical circuit 26 was created with corresponding software. Testing was computer automated using a syringe pump to provide fluidics control of the repeated application and removal of the aqueous solution 10.

Figure 30:
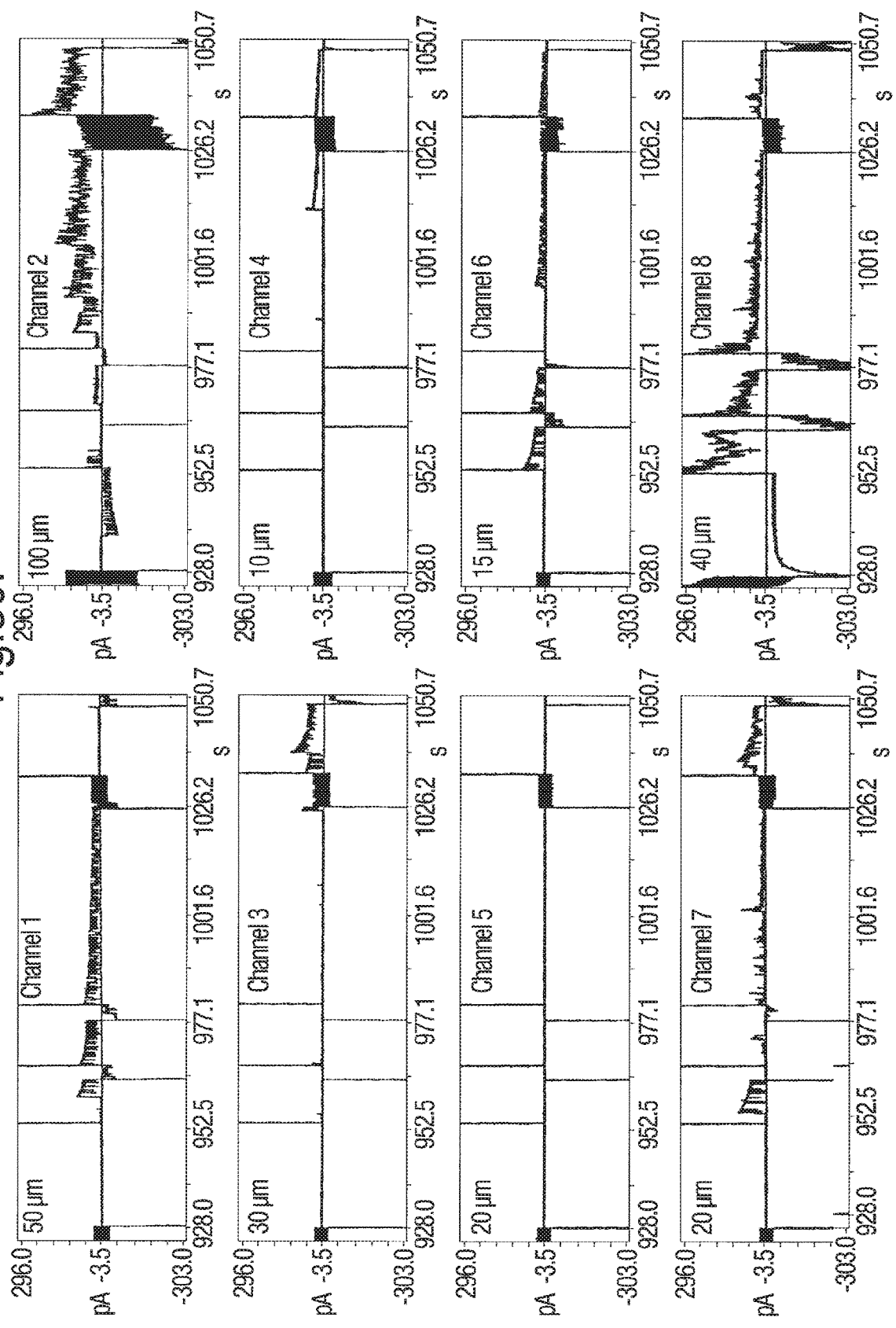

Formation of layers 11 and insertion of membrane proteins at plural recesses 5 was successfully recorded in parallel. Often this occurred at each recess 5 although sometimes a layer 11 failed to form at one or more recesses 5. For example, typical current traces for recesses 5 constructed with gold electrodes and operating without a redox couple in solution are shown in FIG. 30 demonstrating simultaneous formation of eight layers 11, each having one or two α-hemolysin pores inserted, with cyclodextrin binding events. Again there is no cross-talk and this confirms that the layers 11 are operating independently and can produce meaningful measurements in parallel.

Furthermore the apparatus 1 demonstrates successful formation of a layer 11 across the recess 5 of each diameter in the range of 5 μm to 100 μm. Accordingly the apparatus 1 was used to investigate the role of the diameter of the recess 5 and the quantity of pre-treatment coating applied, by experimentally testing the percentage success rate of forming a layer 5 with three different concentrations of pre-treatment coating 30, namely 0.5%, 1.0%, and 2.0% hexadecane in pentane. The results showed that in the case of too little pretreatment coating 30, it was not possible to form the layer 11 across the range of diameters of recess 5. Furthermore in the case of too much pretreatment coating 30, it was not possible to wet the electrode 21 and formation of the layer 11 could not be observed. In this particular configuration, the yield of formation of layers 11 was greater than 60% for the range of diameters 15 μm to 100 μm. Factors affecting layer formation, some of which were investigated in this experiment include, but are not limited to, pretreatment coating 30, diameter of recess 5, depth of recess 5, aspect ratio of recess 5, surface properties of the recess 5, surface properties of the surfaces around the recess, fluid flow within the chamber 7, the amphiphilic molecules used in the layer formation and the physical and electrical properties of the electrode 21 within the recess 5. Subsequent experiments have demonstrated yield of formation of layers 11, verified by stochastic binding signals of inserted membrane channels, greater than 70% using the 128 recesses, each 100 μm in diameter, of the device of FIG. 28.

In the apparatus 1 described above, the conductive tracks 27 from the electrode 21 to the contact 22 is formed on a surface of the substrate 3 under the further layer. This may be referred to as a planar escape route for the conductive track 27. As previously described the separate conductive tracks 27 allow each electrode 21 to be connected individually to a dedicated low-noise high-input impedance picoammeter in the circuit 26 whilst minimizing the signal deterioration due to noise and bandwidth reduction. Such planar conductive tracks 27 are ideal for an apparatus 1 having a small number of recesses 5 and a thick layer between the tracks 27 and the aqueous solution 10.

However, for uses where high sensitivity is required, the electrical connection between the electrodes 21 and the amplifier circuit desirably has low parasitic capacitance and low leakage to the surroundings. Parasitic capacitance causes noise and hence signal deterioration and bandwidth reduction. Leakage also increases noise, as well as introducing an offset current. In the apparatus 1, the conductive tracks 27 experience some degree of parasitic capacitance and leakage, both between tracks 27 and between track and aqueous solution 10. As the number of recesses in the array increases, the number of electrical connections to escape increases and with a planar escape route, a practical limit is reached where the density of the conductive tracks 27 creates too much parasitic capacitance and/or leakage between tracks. Furthermore as the thickness of the layer 4 decreases the capacitance and/or leakage between the tracks 27 and the aqueous solution 10 increases.

By way of example, typical figures may be obtained by modelling the lipid bilayer as a capacitive element with a typical value for the capacitance per unit area of 0.8 pF/cm$^2$. The parasitic capacitance between track 27 and aqueous solution 10 can be crudely modelled as a capacitative element with the area of track 27 exposed, through the layer, to the aqueous solution. Typical values for the track 27 may be 50 μm wide with 2 mm exposed and a relative permittivity (dielectric constant) of the layer around 3. For a 100 μm diameter bilayer and 20 μm deep recess the capacitance is 63 pF with a track-solution parasitic capacitance of 0.13 pF. However scaling to smaller bilayers of 5 μm diameter and 1 μm deep the capacitance is 0.16 pF with parasitic capacitance 0.53 pF. For smaller bilayers and thinner layers the parasitic capacitance dominates.

Figure 31:
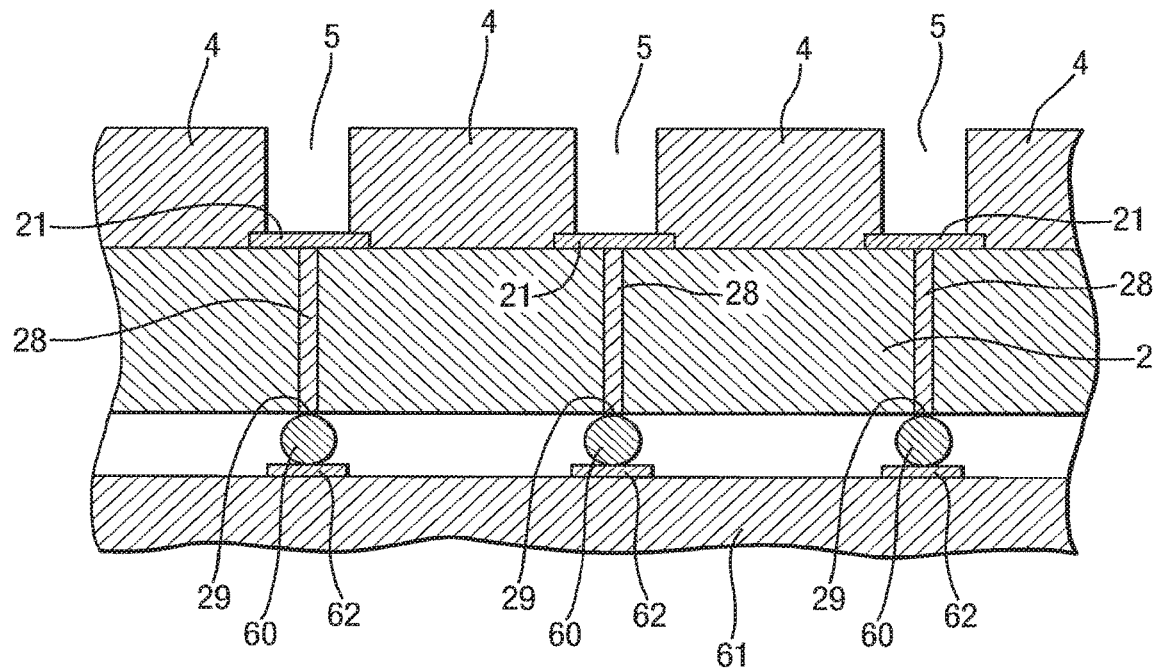
FIG. 31 is a cross-sectional view of a portion of a modified apparatus.

To reduce this problem, a modification shown in FIG. 31 comprises, replacing the conductive track 27 by a conductive path 28 which extends through the body 2 to a contact 29 on the opposite side of the body 2 from the electrode 21. In particular, the conductive path 28 extends through the substrate 3. As this substrate 3 provides a thicker dielectric between the conductive paths 28 than is possible between the planar conductive paths 27, a much lower parasitic capacitance is achieved. Also, the leakage is low due to the thickness and dielectric properties of the substrate 3. Consequently, the use of the conductive paths 28 effectively increases the number of recesses 5 which may be accommodated in the body 2 before the practical limits imposed by parasitic capacitance and/or leakage are met. This form of interconnect can be attached to a low-capacitance multi-layer substrate 61, which allows a far greater number of electrical escape routes by virtue of the number of layers and the low dielectric constant of the material. In addition the use of solder bump technology (also known as "flip chip" technology) and a suitable connector allows the apparatus 1 shown in FIG. 31, excluding the substrate 61, to be made as low cost disposable part.

The conductive path 28 may be formed using known through-wafer interconnection technology. Types of through-wafer interconnects which may be applied to form the conductive path include without limitation: on substrates 3 of silicon, through-wafer interconnects formed by producing a via through the silicon wafer, isolating the internal surface of via and filling the via with a conducting material, or alternatively the conductive path 28 is formed by producing a semiconductor PN junction in the form of a cylindrical via through the silicon substrate; on substrates 3 of glass, through-wafer interconnects formed by methods including laser drilling, wet etching and filling vias with metal or doped semiconductor material; and on substrates 3 made of polymers, through-wafer interconnects formed by methods including laser drilling, laser ablation, screen printed conductors and known printed circuit board techniques.

As the opposite side of the body 2 from the electrode 21 is dry, an electrical point contact array can be used to make connections to the electrical circuit 26. By way of example, FIG. 31 illustrates the use of solder bump connections. In particular, deposited on each contact 29 are respective solder bumps 60 on which a circuit element 61 is mounted so that the solder bumps 60 make electrical contact with a track 62 on the circuit element 61.

The circuit element 61 may be a printed circuit board for example as shown in FIG. 13.

Figure 32:
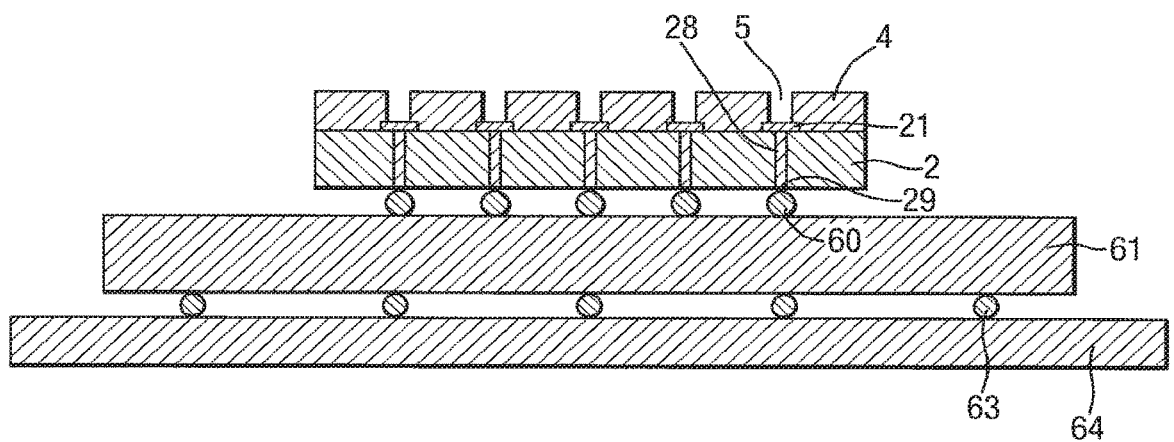
FIG. 32 is a cross-sectional view of another modified apparatus.

Alternatively, the circuit element 61 could be an integrated circuit chip or a laminate, for example a low temperature cured ceramic package. Such an integrated circuit chip or laminate may be used as a method of spreading out connections, connecting to a further solder bump array on the opposite side of the integrated circuit chip or laminate with a greater pitch. An example of this is shown in FIG. 32 in which the circuit element 61 is an integrated circuit chip or a laminate providing connections from the solder bumps 60 deposited on the body 2 to further solder bumps 63 arrayed at a greater pitch and used to connect to a further circuit element 64, for example a printed circuit board. The circuit element 61 being an integrated circuit chip or laminate may also be used to escape connections sideways in a multi-layer format.

In the case of a substrate 3 of semiconductor material such as silicon, two types of through-wafer interconnect which may be applied to make the conductive path 28 are Metal-Insulator-Semiconductor (MIS), and a PN junction type. In MIS, a hole is drilled through the silicon chip by Deep Reactive Ion Etching (DRIE) process and this hole is coated with insulator and then filled with metal to form a the conductive path 28. The PN junction type of through-wafer interconnect is a semiconductor junction formed into a cylindrical via through a silicon chip. Each type of through-wafer interconnection is formed on silicon wafers that have been thinned down to less than 0.3 mm to save DRIE processing time in making the holes. The important feature of PN junction type through-wafer interconnects is the low capacitance provided by having a large depletion region compared to the MIS type of interconnect. This is partially helped by increasing the reverse-bias of the junction.

---

SEQUENCE LISTING

| | |
|---|---|
| <110> | OXFORD NANOPORE TECHNOLOGIES LIMITED |
| <120> | FORMATION OF LAYERS OF AMPHIPHILIC MOLECULES |
| <130> | N.102405B CHM |
| <150> | GB 0724736.4 |
| <151> | 2007-12-19 |

SEQUENCE LISTING

<150> US 61/080,492

<151> 2008-07-14

<160> 3

<170> PatentIn version 3.5

<210> 1

<211> 960

<212> DNA

<213> *Staphylococcus aureus*

<220>

<221> CDS

<222> (1)..(960)

<400> 1

```
atg aaa aca cgt ata gtc agc tca gta aca aca aca cta ttg cta ggt    48
Met Lys Thr Arg Ile Val Ser Ser Val Thr Thr Thr Leu Leu Leu Gly
1               5                   10                  15 tca ata tta atg aat cct gtc gct aat gcc gca gat tct gat att aat    96
Ser Ile Leu Met Asn Pro Val Ala Asn Ala Ala Asp Ser Asp Ile Asn
            20                  25                  30 att aaa acc ggt act aca gat att gga agc aat act aca gta aaa aca   144
Ile Lys Thr Gly Thr Thr Asp Ile Gly Ser Asn Thr Thr Val Lys Thr
        35                  40                  45 gat gat tta gtc act tat gat aaa gaa aat ggc atg cac aaa aaa gta   192
Gly Asp Leu Val Thr Tyr Asp Lys Glu Asn Gly Met His Lys Lys Val
    50                  55                  60 ttt tat agt ttt atc gat gat aaa aat cac aat aaa aaa ctg cta gtt   240
Phe Tyr Ser Phe Ile Asp Asp Lys Asn His Asn Lys Lys Leu Leu Val
65                  70                  75                  80 att aga aca aaa ggt acc att gct ggt caa tat aga gtt tat agc gaa   288
Ile Arg Thr Lys Gly Thr Ile Ala Gly Gln Tyr Arg Val Tyr Ser Glu
                85                  90                  95 gaa ggt gct aac aaa agt ggt tta gcc tgg cct tca gcc ttt aag gta   336
Glu Gly Ala Asn Lys Ser Gly Leu Ala Trp Pro Ser Ala Phe Lys Val
            100                 105                 110 cag ttg caa cta cct gat aat gaa gta gct caa ata tct gat tac tat   384
Gln Leu Gln Leu Pro Asp Asn Glu Val Ala Gln Ile Ser Asp Tyr Tyr
        115                 120                 125 cca aga aat tcg att gat aca aaa gag tat atg agt act tta act tat   432
Pro Arg Asn Ser Ile Asp Thr Lys Glu Tyr Met Ser Thr Leu Thr Tyr
    130                 135                 140 gga ttc aac ggt aat gtt act ggt gat gat aca gga aaa att ggc ggc   480
Gly Phe Asn Gly Asn Val Thr Gly Asp Asp Thr Gly Lys Ile Gly Gly
145                 150                 155                 160 ctt att ggt gca aat gtt tcg att ggt cat aca ctg aaa tat gtt caa   528
Leu Ile Gly Ala Asn Val Ser Ile Gly His Thr Leu Lys Tyr Val Gln
                165                 170                 175 cct gat ttc aaa aca att tta gag agc cca act gat aaa aaa gta ggc   576
Pro Asp Phe Lys Thr Ile Leu Glu Ser Pro Thr Asp Lys Lys Val Gly
            180                 185                 190 tgg aaa gtg ata ttt aac aat atg gtg aat caa aat tgg gga cca tac   624
Trp Lys Val Ile Phe Asn Asn Met Val Asn Gln Asn Trp Gly Pro Tyr
        195                 200                 205
```

-continued

SEQUENCE LISTING

```
gat cga gat tct tgg aac ccg gta tat ggc aat caa ctt ttc atg aaa   672
Asp Arg Asp Ser Trp Asn Pro Val Tyr Gly Asn Gln Leu Phe Met Lys
    210                 215                 220 act aga aat ggt tct atg aaa gca gca gat aac ttc ctt gat cct aac   720
Thr Arg Asn Gly Ser Met Lys Ala Ala Asp Asn Phe Leu Asp Pro Asn
225                 230                 235                 240 aaa gca agt tct cta tta tct tca ggg ttt tca cca gac tcc gct aca   768
Lys Ala Ser Ser Leu Leu Ser Ser Gly Phe Ser Pro Asp Phe Ala Thr
                245                 250                 255 gtt att act atg gat aga aaa gca tcc aaa caa caa aca aat ata gat   816
Val Ile Thr Met Asp Arg Lys Ala Ser Lys Gln Gln Thr Asn Ile Asp
            260                 265                 270 gta ata tac gaa cga gtt cgt gat gat tac caa ttg cat tgg act tca   864
Val Ile Tyr Glu Arg Val Arg Asp Asp Tyr Gln Leu His Trp Thr Ser
        275                 280                 285 aca aat tgg aaa ggt acc aat act aaa gat aaa tgg aca gat cgt tct   912
Thr Asn Trp Lys Gly Thr Asn Thr Lys Asp Lys Trp Thr Asp Arg Ser
    290                 295                 300 tca gaa aga tat aaa atc gat tgg gaa aaa gaa gaa atg aca aat taa   960
Ser Glu Arg Tyr Lys Ile Asp Trp Glu Lys Glu Glu Met Thr Asn Asa
305                 310                 315
```

<210> 2

<211> 319

<212> PRT

<213> *Staphylococcus aureus*

<400> 2

```
Met Lys Thr Arg Ile Val Ser Ser Val Thr Thr Thr Leu Leu Leu Gly
1               5                   10                  15

Ser Ile Leu Met Asn Pro Val Ala Asn Ala Ala Asp Ser Asp Ile Asn
            20                  25                  30

Ile Lys Thr Gly Thr Thr Asp Ile Gly Ser Asn Thr Thr Val Lys Thr
        35                  40                  45

Gly Asp Leu Val Thr Tyr Asp Lys Glu Asn Gly Met His Lys Lys Val
    50                  55                  60

Phe Tyr Ser Phe Ile Asp Asp Lys Asn His Asn Lys Lys Leu Leu Val
65                  70                  75                  80

Ile Arg Thr Lys Gly Thr Ile Ala Gly Gln Tyr Arg Val Tyr Ser Glu
            85                  90                  95

Glu Gly Ala Asn Lys Ser Gly Leu Ala Trp Pro Ser Ala Phe Lys Val
            100                 105                 110

Gln Leu Gln Leu Pro Asp Asn Glu Val Ala Gln Ile Ser Asp Tyr Tyr
        115                 120                 175

Pro Arg Asn Ser Ile Asp Thr Lys Glu Tyr Met Ser Thr Leu Thr Tyr
    130                 135                 140

Gly Phe Asn Gly Asn Val Thr Gly Asp Asp Thr Gly Lys Ile Gly Gly
145                 150                 155                 160

Leu Ile Gly Ala Asn Val Ser Ile Gly His Thr Leu Lys Tyr Val Gln
            165                 170                 175

Pro Asp Phe Lys Thr Ile Leu Glu Ser Pro Thr Asp Lys Lys Val Gly
        180                 185                 190

Trp Lys Val Ile Phe Asn Asn Met Val Asn Gln Asn Trp Gly Pro Tyr
    195                 200                 205
```

SEQUENCE LISTING

Asp Arg Asp Ser Trp Asn Pro Val Tyr Gly Asn Gln Leu Phe Met Lys
    210                 215                 220

Thr Arg Asn Gly Ser Met Lys Ala Ala Asp Asn Phe Len Asp Pro Asn
225                 230                 235                 240

Lys Ala Ser Ser Leu Leu Ser Ser Gly Phe Ser Pro Asp Phe Ala Thr
                245                 250                 255

Val Ile Thr Met Asp Arg Lys Ala Ser Lys Gln Gln Thr Asn Ile Asp
            260                 265                 270

Val Ile Tyr Glu Arg Val Arg Asp Asp Tyr Gln Leu His Trp Thr Ser
        275                 280                 285

Thr Asn Trp Lys Gly Thr Asn Thr Lys Asp Lys Trp Thr Asp Arg Ser
290                 295                 300

Ser Glu Arg Tyr Lys Ile Asp Trp Glu Lys Glu Met Thr Asn
305                 310                 315

<210> 3

<211> 294

<212> PRT

<213> Staphylococcus aureus

<400> 3

Met Ala Asp Ser Asp Ile Asn Ile Lys Thr Gly Thr Thr Asp Ile Gly
1               5                   10                  15

Ser Asn Thr Thr Val Lys Thr Gly Asp Leu Val Thr Tyr Asp Lys Glu
                20                  25                  30

Asn Gly Met His Lys Lys Val Phe Tyr Ser Phe Ile Asp Asp Lys Asn
            35                  40                  45

His Asn Lys Lys Leu Leu Val Ile Arg Thr Lys Gly Thr Ile Ala Gly
        50                  55                  60

Gln Tyr Arg Val Tyr Ser Glu Glu Gly Ala Asn Lys Ser Gly Leu Ala
65                  70                  75                  80

Trp Pro Ser Ala Phe Lys Val Gln Leu Gln Leu Pro Asp Asn Gln Val
                85                  90                  95

Ala Gln Ile Ser Asp Tyr Tyr Pro Arg Asn Ser Ile Asp Thr Lys Glu
            100                 105                 110

Tyr Met Ser Thr Leu Thr Tyr Gly Phe Asn Gly Asn Val Thr Gly Asp
        115                 120                 125

Asp Thr Gly Lys Ile Gly Gly Leu Ile Gly Ala Asn Val Ser Ile Gly
    130                 135                 140

His Thr Leu Lys Tyr Val Gln Pro Asp Phe Lys Thr Ile Leu Gln Ser
145                 150                 155                 160

Pro Thr Asp Lys Lys Val Gly Trp Lys Val Ile Phe Asn Asn Met Val
                165                 170                 175

Asn Gln Asn Trp Gly Pro Tyr Asp Arg Asp Ser Trp Asn Pro Val Tyr
            180                 185                 190

Gly Asn Gln Leu Phe Met Lys Thr Arg Asn Gly Ser Met Lys Ala Ala
        195                 200                 205

Asp Asn Phe Len Asp Pro Asn Lys Ala Ser Ser Leu Leu Ser Ser Gly
    210                 215                 220

Phe Ser Pro Asp Phe Ala Thr Val Ile Thr Met Asp Arg Lys Ala Ser
225                 230                 235                 240

SEQUENCE LISTING

```
Lys Gln Gln Thr Asn Ile Asp Val Ile Tyr Gln Arg Val Arg Asp Asp
                245                 250                 255

Tyr Gln Leu His Trp Thr Ser Thr Asn Trp Lys Gly Thr Asn Thr Lys
            260                 265                 270

Asp Lys Trp Thr Asp Arg Ser Ser Glu Arg Tyr Lys Ile Asp Trp Glu
        275                 280                 285

Lys Gln Glu Met Thr Asn
    290
```

SEQUENCE LISTING

```
<160> NUMBER OF SEQ ID NOS: 3

<210> SEQ ID NO 1
<211> LENGTH: 960
<212> TYPE: DNA
<213> ORGANISM: Staphylococcus aureus
<220> FEATURE:
<221> NAME/KEY: CDS
<222> LOCATION: (1)..(960)

<400> SEQUENCE: 1 atg aaa aca cgt ata gtc agc tca gta aca aca aca cta ttg cta ggt      48
Met Lys Thr Arg Ile Val Ser Ser Val Thr Thr Thr Leu Leu Leu Gly
1               5                  10                  15 tcc ata tta atg aat cct gtc gct aat gcc gca gat tct gat att aat      96
Ser Ile Leu Met Asn Pro Val Ala Asn Ala Ala Asp Ser Asp Ile Asn
            20                  25                  30 att aaa acc ggt act aca gat att gga agc aat act aca gta aaa aca     144
Ile Lys Thr Gly Thr Thr Asp Ile Gly Ser Asn Thr Thr Val Lys Thr
        35                  40                  45 ggt gat tta gtc act tat gat aaa gaa aat ggc atg cac aaa aaa gta     192
Gly Asp Leu Val Thr Tyr Asp Lys Glu Asn Gly Met His Lys Lys Val
    50                  55                  60 ttt tat agt ttt atc gat gat aaa aat cac aat aaa aaa ctg cta gtt     240
Phe Tyr Ser Phe Ile Asp Asp Lys Asn His Asn Lys Lys Leu Leu Val
65                  70                  75                  80 att aga aca aaa ggt acc att gct ggt caa tat aga gtt tat agc gaa     288
Ile Arg Thr Lys Gly Thr Ile Ala Gly Gln Tyr Arg Val Tyr Ser Glu
                85                  90                  95 gaa ggt gct aac aaa agt ggt tta gcc tgg cct tca gcc ttt aag gta     336
Glu Gly Ala Asn Lys Ser Gly Leu Ala Trp Pro Ser Ala Phe Lys Val
            100                 105                 110 cag ttg caa cta cct gat aat gaa gta gct caa ata tct gat tac tat     384
Gln Leu Gln Leu Pro Asp Asn Glu Val Ala Gln Ile Ser Asp Tyr Tyr
        115                 120                 125 cca aga aat tcg att gat aca aaa gag tat atg agt act tta act tat     432
Pro Arg Asn Ser Ile Asp Thr Lys Glu Tyr Met Ser Thr Leu Thr Tyr
    130                 135                 140 gga ttc aac ggt aat gtt act ggt gat gat aca gga aaa att ggc ggc     480
Gly Phe Asn Gly Asn Val Thr Gly Asp Asp Thr Gly Lys Ile Gly Gly
145                 150                 155                 160 ctt att ggt gca aat gtt tcg att ggt cat aca ctg aaa tat gtt caa     528
Leu Ile Gly Ala Asn Val Ser Ile Gly His Thr Leu Lys Tyr Val Gln
                165                 170                 175 cct gat ttc aaa aca att tta gag agc cca act gat aaa aaa gta ggc     576
Pro Asp Phe Lys Thr Ile Leu Glu Ser Pro Thr Asp Lys Lys Val Gly
```

```
            180                 185                 190
tgg aaa gtg ata ttt aac aat atg gtg aat caa aat tgg gga cca tac    624
Trp Lys Val Ile Phe Asn Asn Met Val Asn Gln Asn Trp Gly Pro Tyr
        195                 200                 205 gat cga gat tct tgg aac ccg gta tat ggc aat caa ctt ttc atg aaa    672
Asp Arg Asp Ser Trp Asn Pro Val Tyr Gly Asn Gln Leu Phe Met Lys
210                 215                 220 act aga aat ggt tct atg aaa gca gca gat aac ttc ctt gat cct aac    720
Thr Arg Asn Gly Ser Met Lys Ala Ala Asp Asn Phe Leu Asp Pro Asn
225                 230                 235                 240 aaa gca agt tct cta tta tct tca ggg ttt tca cca gac ttc gct aca    768
Lys Ala Ser Ser Leu Leu Ser Ser Gly Phe Ser Pro Asp Phe Ala Thr
            245                 250                 255 gtt att act atg gat aga aaa gca tcc aaa caa caa aca aat ata gat    816
Val Ile Thr Met Asp Arg Lys Ala Ser Lys Gln Gln Thr Asn Ile Asp
            260                 265                 270 gta ata tac gaa cga gtt cgt gat gat tac caa ttg cat tgg act tca    864
Val Ile Tyr Glu Arg Val Arg Asp Asp Tyr Gln Leu His Trp Thr Ser
            275                 280                 285 aca aat tgg aaa ggt acc aat act aaa gat aaa tgg aca gat cgt tct    912
Thr Asn Trp Lys Gly Thr Asn Thr Lys Asp Lys Trp Thr Asp Arg Ser
        290                 295                 300 tca gaa aga tat aaa atc gat tgg gaa aaa gaa gaa atg aca aat taa    960
Ser Glu Arg Tyr Lys Ile Asp Trp Glu Lys Glu Glu Met Thr Asn
305                 310                 315
```

<210> SEQ ID NO 2
<211> LENGTH: 319
<212> TYPE: PRT
<213> ORGANISM: Staphylococcus aureus

<400> SEQUENCE: 2

```
Met Lys Thr Arg Ile Val Ser Ser Val Thr Thr Thr Leu Leu Leu Gly
1               5                   10                  15

Ser Ile Leu Met Asn Pro Val Ala Asn Ala Ala Asp Ser Asp Ile Asn
                20                  25                  30

Ile Lys Thr Gly Thr Thr Asp Ile Gly Ser Asn Thr Thr Val Lys Thr
            35                  40                  45

Gly Asp Leu Val Thr Tyr Asp Lys Glu Asn Gly Met His Lys Lys Val
        50                  55                  60

Phe Tyr Ser Phe Ile Asp Asp Lys Asn His Asn Lys Lys Leu Leu Val
65                  70                  75                  80

Ile Arg Thr Lys Gly Thr Ile Ala Gly Gln Tyr Arg Val Tyr Ser Glu
                85                  90                  95

Glu Gly Ala Asn Lys Ser Gly Leu Ala Trp Pro Ser Ala Phe Lys Val
            100                 105                 110

Gln Leu Gln Leu Pro Asp Asn Glu Val Ala Gln Ile Ser Asp Tyr Tyr
        115                 120                 125

Pro Arg Asn Ser Ile Asp Thr Lys Glu Tyr Met Ser Thr Leu Thr Tyr
    130                 135                 140

Gly Phe Asn Gly Asn Val Thr Gly Asp Asp Thr Gly Lys Ile Gly Gly
145                 150                 155                 160

Leu Ile Gly Ala Asn Val Ser Ile Gly His Thr Leu Lys Tyr Val Gln
                165                 170                 175

Pro Asp Phe Lys Thr Ile Leu Glu Ser Pro Thr Asp Lys Lys Val Gly
            180                 185                 190

Trp Lys Val Ile Phe Asn Asn Met Val Asn Gln Asn Trp Gly Pro Tyr
```

```
            195                 200                 205
Asp Arg Asp Ser Trp Asn Pro Val Tyr Gly Asn Gln Leu Phe Met Lys
210                 215                 220

Thr Arg Asn Gly Ser Met Lys Ala Ala Asp Asn Phe Leu Asp Pro Asn
225                 230                 235                 240

Lys Ala Ser Ser Leu Leu Ser Ser Gly Phe Ser Pro Asp Phe Ala Thr
                245                 250                 255

Val Ile Thr Met Asp Arg Lys Ala Ser Lys Gln Gln Thr Asn Ile Asp
            260                 265                 270

Val Ile Tyr Glu Arg Val Arg Asp Asp Tyr Gln Leu His Trp Thr Ser
        275                 280                 285

Thr Asn Trp Lys Gly Thr Asn Thr Lys Asp Lys Trp Thr Asp Arg Ser
290                 295                 300

Ser Glu Arg Tyr Lys Ile Asp Trp Glu Lys Glu Met Thr Asn
305                 310                 315

<210> SEQ ID NO 3
<211> LENGTH: 294
<212> TYPE: PRT
<213> ORGANISM: Staphylococcus aureus

<400> SEQUENCE: 3

Met Ala Asp Ser Asp Ile Asn Ile Lys Thr Gly Thr Thr Asp Ile Gly
1               5                   10                  15

Ser Asn Thr Thr Val Lys Thr Gly Asp Leu Val Thr Tyr Asp Lys Glu
            20                  25                  30

Asn Gly Met His Lys Lys Val Phe Tyr Ser Phe Ile Asp Asp Lys Asn
        35                  40                  45

His Asn Lys Lys Leu Leu Val Ile Arg Thr Lys Gly Thr Ile Ala Gly
    50                  55                  60

Gln Tyr Arg Val Tyr Ser Glu Glu Gly Ala Asn Lys Ser Gly Leu Ala
65                  70                  75                  80

Trp Pro Ser Ala Phe Lys Val Gln Leu Gln Leu Pro Asp Asn Glu Val
                85                  90                  95

Ala Gln Ile Ser Asp Tyr Tyr Pro Arg Asn Ser Ile Asp Thr Lys Glu
            100                 105                 110

Tyr Met Ser Thr Leu Thr Tyr Gly Phe Asn Gly Asn Val Thr Gly Asp
        115                 120                 125

Asp Thr Gly Lys Ile Gly Gly Leu Ile Gly Ala Asn Val Ser Ile Gly
    130                 135                 140

His Thr Leu Lys Tyr Val Gln Pro Asp Phe Lys Thr Ile Leu Glu Ser
145                 150                 155                 160

Pro Thr Asp Lys Lys Val Gly Trp Lys Val Ile Phe Asn Asn Met Val
                165                 170                 175

Asn Gln Asn Trp Gly Pro Tyr Asp Arg Asp Ser Trp Asn Pro Val Tyr
            180                 185                 190

Gly Asn Gln Leu Phe Met Lys Thr Arg Asn Gly Ser Met Lys Ala Ala
        195                 200                 205

Asp Asn Phe Leu Asp Pro Asn Lys Ala Ser Ser Leu Leu Ser Ser Gly
    210                 215                 220

Phe Ser Pro Asp Phe Ala Thr Val Ile Thr Met Asp Arg Lys Ala Ser
225                 230                 235                 240

Lys Gln Gln Thr Asn Ile Asp Val Ile Tyr Glu Arg Val Arg Asp Asp
                245                 250                 255
```

-continued

```
Tyr Gln Leu His Trp Thr Ser Thr Asn Trp Lys Gly Thr Asn Thr Lys
            260             265             270

Asp Lys Trp Thr Asp Arg Ser Ser Glu Arg Tyr Lys Ile Asp Trp Glu
        275             280             285

Lys Glu Glu Met Thr Asn
    290
```

The invention claimed is:

1. A device for polymer sequencing comprising:
an array of nanopores,
above the array of nanopores, in fluidic contact with the array of nanopores, an upper fluidic region comprising an upper electrode, the upper fluidic region comprising polymer molecules,
below the array of nanopores, an array of discrete fluidic regions, each discrete fluidic region in fluidic contact with a nanopore of the array of nanopores, and each discrete fluidic region comprising a lower electrode and internal surfaces, wherein there is no direct fluidic contact between the discrete fluidic regions,
a pre-treatment coating of a hydrophobic fluid applied to the internal surfaces of each discrete fluidic region, wherein the hydrophobic fluid does not cover the lower electrode,
an array of layers of amphiphilic molecules, wherein each layer of amphiphilic molecules separates one of the discrete fluidic regions from the upper fluidic region,
wherein each nanopore of the array of nanopores is disposed within one of the layers of amphiphilic molecules, and
an array of electronic circuits below the array of discrete fluidic regions, each electronic circuit comprising an amplifier in electrical contact with the fluidic region above it.

2. The device of claim 1, wherein voltage is applied between the upper electrode and the lower electrode of each discrete fluidic region, resulting in removal of excess hydrophobic fluid covering the lower electrode.

3. The device of claim 1, wherein the polymer molecules comprise nucleic acid molecules.

4. The device of claim 1, wherein the nucleic acid molecules comprise DNA.

5. The device of claim 1, wherein the device comprises a semiconductor substrate in which the array of electronic circuits is formed.

6. The device of claim 1, wherein the array of electronic circuits further comprise analog to digital converters, memory, or clock circuits.

7. The device of claim 1, wherein each discrete fluidic region has two electrodes, one disposed below each discrete fluidic region and one disposed above each discrete fluidic region, wherein the one disposed above each discrete fluidic region acts as a drive electrode, and the one disposed below each discrete fluidic region acts as a measurement electrode.

8. The device of claim 1, wherein the nanopores comprise protein nanopores.

9. The device of claim 8, wherein the protein nanopores comprise alpha-hemolysin proteins.

10. The device of claim 8, wherein the protein nanopores are within biological membranes.

11. The device of claim 1, wherein the device comprises a substrate comprising a semiconductor component bound to an insulator component.

12. The device of claim 1, wherein each layer of amphiphilic molecules has an electrical resistance of at least 100 GO.

13. The device of claim 1, wherein the array of nanopores comprises up to 128 nanopores.

14. The device of claim 7, wherein the electrode disposed above each discrete fluidic region is a single electrode common to all of the discrete fluidic regions.

15. The device of claim 1, wherein each layer of amphiphilic molecules has a diameter of 10 μm to 500 μm.

16. The device of claim 1, further comprising an array of conductive paths extending from the array of discrete fluidic regions to the array of electronic circuits.

17. The device of claim 1, wherein the array of layers of amphiphilic molecules comprise lipids.

18. The device of claim 17, wherein the lipids form a lipid bilayer.

* * * * *